US012780939B2

(12) United States Patent
Scheinberg et al.

(10) Patent No.: US 12,780,939 B2
(45) Date of Patent: Nov. 3, 2026

(54) COMPOSITIONS AND METHODS FOR ADOPTIVE CELL THERAPY FOR CANCER

(71) Applicant: MEMORIAL SLOAN KETTERING CANCER CENTER, New York, NY (US)

(72) Inventors: David A. Scheinberg, New York, NY (US); Thomas Gardner, New York, NY (US); Megan Dacek, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1172 days.

(21) Appl. No.: 17/292,811

(22) PCT Filed: Nov. 12, 2019

(86) PCT No.: PCT/US2019/060995
§ 371 (c)(1),
(2) Date: May 11, 2021

(87) PCT Pub. No.: WO2020/102240
PCT Pub. Date: May 22, 2020

(65) Prior Publication Data

US 2021/0393692 A1 Dec. 23, 2021

Related U.S. Application Data

(60) Provisional application No. 62/760,864, filed on Nov. 13, 2018.

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 16/28*** | (2006.01) |
| ***C07K 16/30*** | (2006.01) |
| ***C12N 5/0783*** | (2010.01) |

(52) U.S. Cl.
CPC .......... *C07K 16/3092* (2013.01); *A61K 40/11* (2025.01); *A61K 40/31* (2025.01); *A61K 40/4204* (2025.01); *A61K 40/4205* (2025.01); *A61K 40/4211* (2025.01); *A61K 40/4243* (2025.01); *A61K 40/4257* (2025.01); *A61P 35/00* (2018.01); *C07K 16/2887* (2013.01); *C07K 16/3053* (2013.01); *C12N 5/0636* (2013.01); *A61K 2239/48* (2023.05); *A61K 2239/59* (2023.05)

(58) Field of Classification Search
CPC ............ C07K 16/3092; C07K 16/2887; C07K 16/3053; C07K 14/70503; C07K 14/7051; C07K 2317/73; C07K 2319/03; C07K 16/2803; A61K 39/4611; A61K 39/4631; A61K 39/464404; A61K 39/464406; A61K 39/464412; A61K 39/464453; A61K 39/46447; A61K 2239/48; A61K 2239/59; A61K 39/3955; A61K 39/39558; A61K 2039/505; A61P 35/00; C12N 5/0636; C12N 2501/2302; C12N 2502/30; C12N 2510/00
See application file for complete search history.

(56) References Cited

U.S. PATENT DOCUMENTS

| | | | | |
|---|---|---|---|---|
| 9,944,911 | B2 * | 4/2018 | Ring | ........................ C12N 9/16 |
| 2015/0329616 | A1 | 11/2015 | Uger et al. | |
| 2016/0045551 | A1 | 2/2016 | Brentjens et al. | |

FOREIGN PATENT DOCUMENTS

| | | | | |
|---|---|---|---|---|
| WO | WO-2016141347 | A2 * | 9/2016 | ........... C12Q 1/6883 |
| WO | WO-2016141357 | A1 * | 9/2016 | ............. A61K 35/14 |
| WO | WO-2017/184553 | A1 | 10/2017 | |
| WO | WO-2018/005775 | A1 | 1/2018 | |

OTHER PUBLICATIONS

Keichiro Mihara et al: "Synergistic and persistent effect of T-cell immunotherapy with anti-CD19 or anti-CD38 chimeric receptor in conjunction with rituximab on B-cell non-Hodgkin lymphoma", British Journal of Haematology, John Wiley, Hoboken, USA, vol. 151, No. 1, Jul. 30, 2010 (Jul. 30, 2010) , pp. 37-46, XP071161485, ISSN: 0007-1048, DOI: 10.IIII/J.1365-2141.2010.08297.X abstract.
International Search Report and Written Opinion on PCT PCT/US2019/060995 dated Apr. 7, 2020 (13 pages).

* cited by examiner

*Primary Examiner* — Jeremy C Flinders
*Assistant Examiner* — Masudur Rahman
(74) *Attorney, Agent, or Firm* — Foley & Lardner LLP

(57) ABSTRACT

Provided herein are compositions and methods for adoptive cell therapy comprising engineered immune cells that express a tumor antigen-targeted chimeric antigen receptor and a SIRPα polypeptide. Also disclosed herein are methods of enhancing the anti-tumor efficacy of an engineered immune cell comprising a tumor antigen-targeted chimeric antigen receptor by combining it with a SIRPα polypeptide.

6 Claims, 21 Drawing Sheets

Specification includes a Sequence Listing.

SEQUENCE LISTING

```
<160> NUMBER OF SEQ ID NOS: 46

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Gly Ser Gly Gly Gly Gly Ser
1               5                   10                  15


<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

ggcggcggcg gatctggagg tggtggctca ggtggcggag gctcc                    45


<210> SEQ ID NO 3
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245


<210> SEQ ID NO 4
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140
```

```
Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg
            260


<210> SEQ ID NO 5
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

gaggtgaagc tgcagcagtc tggggctgag ctggtgaggc ctgggtcctc agtgaagatt     60

tcctgcaagg cttctggcta tgcattcagt agctactgga tgaactgggt gaagcagagg    120

cctggacagg gtcttgagtg gattggacag atttatcctg gagatggtga tactaactac    180

aatggaaagt tcaagggtca agccacactg actgcagaca aatcctccag cacagcctac    240

atgcagctca gcggcctaac atctgaggac tctgcggtct atttctgtgc aagaaagacc    300

attagttcgg tagtagattt ctactttgac tactggggcc aagggaccac ggtcaccgtc    360

tcctcaggtg gaggtggatc aggtggaggt ggatctggtg gaggtggatc tgacattgag    420

ctcacccagt ctccaaaatt catgtccaca tcagtaggag acagggtcag cgtcacctgc    480

aaggccagtc agaatgtggg tactaatgta gcctggtatc aacagaaacc aggacaatct    540

cctaaaccac tgatttactc ggcaacctac cggaacagtg gagtccctga tcgcttcaca    600

ggcagtggat ctgggacaga tttcactctc accatcacta acgtgcagtc taaagacttg    660

gcagactatt tctgtcaaca atataacagg tatccgtaca cgtccggagg ggggaccaag    720

ctggagatca aacgggcggc cgca                                           744


<210> SEQ ID NO 6
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

atggctctcc cagtgactgc cctactgctt cccctagcgc ttctcctgca tgcagaggtg     60

aagctgcagc agtctggggc tgagctggtg aggcctgggt cctcagtgaa gatttcctgc    120

aaggcttctg gctatgcatt cagtagctac tggatgaact gggtgaagca gaggcctgga    180
```

cagggtcttg agtggattgg acagatttat cctggagatg gtgatactaa ctacaatgga 240
aagttcaagg gtcaagccac actgactgca gacaaatcct ccagcacagc ctacatgcag 300
ctcagcggcc taacatctga ggactctgcg gtctatttct gtgcaagaaa gaccattagt 360
tcggtagtag atttctactt tgactactgg ggccaaggga ccacggtcac cgtctcctca 420
ggtggaggtg gatcaggtgg aggtggatct ggtggaggtg gatctgacat tgagctcacc 480
cagtctccaa aattcatgtc cacatcagta ggagacaggg tcagcgtcac ctgcaaggcc 540
agtcagaatg tgggtactaa tgtagcctgg tatcaacaga aaccaggaca atctcctaaa 600
ccactgattt actcggcaac ctaccggaac agtggagtcc ctgatcgctt cacaggcagt 660
ggatctggga cagatttcac tctcaccatc actaacgtgc agtctaaaga cttggcagac 720
tatttctgtc aacaatataa caggtatccg tacacgtccg gagggggggac caagctggag 780 atcaaacgg 789

<210> SEQ ID NO 7
<211> LENGTH: 21
<212> TYPE: PRT
<213> ORGANISM: Unknown
<220> FEATURE:
<223> OTHER INFORMATION: Description of Unknown:
CD8 signal sequence

<400> SEQUENCE: 7

Met Ala Leu Pro Val Thr Ala Leu Leu Leu Pro Leu Ala Leu Leu Leu
1 5 10 15

His Ala Ala Arg Pro
20

<210> SEQ ID NO 8
<211> LENGTH: 63
<212> TYPE: DNA
<213> ORGANISM: Unknown
<220> FEATURE:
<223> OTHER INFORMATION: Description of Unknown:
CD8 signal sequence

<400> SEQUENCE: 8
atggccctgc cagtaacggc tctgctgctg ccacttgctc tgctcctcca tgcagccagg 60
cct 63

<210> SEQ ID NO 9
<211> LENGTH: 18
<212> TYPE: PRT
<213> ORGANISM: Unknown
<220> FEATURE:
<223> OTHER INFORMATION: Description of Unknown:
CD8 signal sequence

<400> SEQUENCE: 9

Met Ala Leu Pro Val Thr Ala Leu Leu Leu Pro Leu Ala Leu Leu Leu
1 5 10 15

His Ala

<210> SEQ ID NO 10
<211> LENGTH: 54
<212> TYPE: DNA
<213> ORGANISM: Unknown
<220> FEATURE:
<223> OTHER INFORMATION: Description of Unknown:
CD8 signal sequence

<400> SEQUENCE: 10
atggctctcc cagtgactgc cctactgctt cccctagcgc ttctcctgca tgca 54

<210> SEQ ID NO 11
<211> LENGTH: 214
<212> TYPE: PRT
<213> ORGANISM: Homo sapiens

<400> SEQUENCE: 11

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Leu Ser Cys Lys Tyr Ser Tyr Asn Leu Phe Ser Arg Glu
35 40 45

Phe Arg Ala Ser Leu His Lys Gly Leu Asp Ser Ala Val Glu Val Cys
50 55 60

Trp Tyr Gly Asn Tyr Ser Gln Gln Leu Gln Val Tyr Ser Lys Thr Gly
65 70 75 80

Phe Asn Cys Asp Gly Lys Leu Gly Asn Glu Ser Val Thr Phe Tyr Leu
85 90 95

Gln Asn Leu Tyr Gln Thr Asp Ile Tyr Phe Cys Lys Ile Glu Val Met
100 105 110

Tyr Pro Pro Pro Tyr Leu Asp Asn Glu Lys Ser Asn Gly Thr Ile Ile
115 120 125

His Val Lys Gly Lys His Leu Cys Pro Ser Pro Leu Phe Pro Gly Pro
130 135 140

Ser Lys Pro Phe Trp Val Leu Val Trp Gly Gly Val Leu Ala Cys Tyr
145 150 155 160

Ser Leu Leu Val Thr Val Ala Phe Ile Ile Phe Trp Val Arg Ser Lys
165 170 175

Arg Ser Arg Leu Leu His Ser Asp Tyr Met Asn Met Thr Pro Arg Arg
180 185 190

Pro Gly Pro Thr Arg Lys His Tyr Gln Pro Tyr Ala Pro Pro Arg Asp
195 200 205

Phe Ala Ala Tyr Arg Ser
210

<210> SEQ ID NO 12
<211> LENGTH: 321
<212> TYPE: DNA
<213> ORGANISM: Homo sapiens

<400> SEQUENCE: 12
attgaagtta tgtatcctcc tccttaccta gacaatgaga agagcaatgg aaccattatc 60
catgtgaaag ggaaacacct ttgtccaagt cccctatttc ccggaccttc taagcccttt 120
tgggtgctgg tggtggttgg tggagtcctg gcttgctata gcttgctagt aacagtggcc 180
tttattattt tctgggtgag gagtaagagg agcaggctcc tgcacagtga ctacatgaac 240
atgactcccc gccgccccgg gcccacccgc aagcattacc agccctatgc cccaccacgc 300
gacttcgcag cctatcgctc c 321

<210> SEQ ID NO 13
<211> LENGTH: 234
<212> TYPE: PRT
<213> ORGANISM: Unknown

<220> FEATURE:
<223> OTHER INFORMATION: Description of Unknown:
CD8 sequence

<400> SEQUENCE: 13

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Trp Lys Ser Gly
    210                 215                 220

Asp Lys Pro Ser Leu Ser Ala Arg Tyr Val
225                 230
```

<210> SEQ ID NO 14
<211> LENGTH: 71
<212> TYPE: PRT
<213> ORGANISM: Unknown
<220> FEATURE:
<223> OTHER INFORMATION: Description of Unknown:
CD8 sequence

<400> SEQUENCE: 14

```
Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp Ile Tyr
        35                  40                  45

Ile Trp Ala Pro Leu Ala Gly Thr Cys Gly Val Leu Leu Leu Ser Leu
    50                  55                  60

Val Ile Thr Leu Tyr Cys Asn
65                  70
```

<210> SEQ ID NO 15

<211> LENGTH: 213
<212> TYPE: DNA
<213> ORGANISM: Unknown
<220> FEATURE:
<223> OTHER INFORMATION: Description of Unknown:
CD8 sequence

<400> SEQUENCE: 15
cccaccacga cgccagcgcc gcgaccacca accccggcgc ccacgatcgc gtcgcagccc 60
ctgtccctgc gcccagaggc gtgccggcca gcggcggggg gcgcagtgca cacgaggggg 120
ctggacttcg cctgtgatat ctacatctgg gcgcccctgg ccgggacttg tggggtcctt 180
ctcctgtcac tggttatcac cctttactgc aac 213

<210> SEQ ID NO 16
<211> LENGTH: 164
<212> TYPE: PRT
<213> ORGANISM: Homo sapiens

<400> SEQUENCE: 16

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Gln Arg Arg Lys Asn Pro Gln Glu Gly Leu Tyr Asn
100 105 110

Glu Leu Gln Lys Asp Lys Met Ala Glu Ala Tyr Ser Glu Ile Gly Met
115 120 125

Lys Gly Glu Arg Arg Arg Gly Lys Gly His Asp Gly Leu Tyr Gln Gly
130 135 140

Leu Ser Thr Ala Thr Lys Asp Thr Tyr Asp Ala Leu His Met Gln Ala
145 150 155 160

Leu Pro Pro Arg

<210> SEQ ID NO 17
<211> LENGTH: 164
<212> TYPE: PRT
<213> ORGANISM: Unknown
<220> FEATURE:
<223> OTHER INFORMATION: Description of Unknown:
CD3-zeta sequence

<400> SEQUENCE: 17

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

```
Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 18
<211> LENGTH: 112
<212> TYPE: PRT
<213> ORGANISM: Unknown
<220> FEATURE:
<223> OTHER INFORMATION: Description of Unknown:
      CD3-zeta sequence

<400> SEQUENCE: 18

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 19
<211> LENGTH: 112
<212> TYPE: PRT
<213> ORGANISM: Unknown
<220> FEATURE:
<223> OTHER INFORMATION: Description of Unknown:
      CD3-zeta sequence

<400> SEQUENCE: 19

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 20
<211> LENGTH: 337
<212> TYPE: DNA
<213> ORGANISM: Unknown
<220> FEATURE:
<223> OTHER INFORMATION: Description of Unknown:
      CD3-zeta sequence

<400> SEQUENCE: 20

agagtgaagt tcagcaggag cgcagagccc cccgcgtacc agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgcg                              337


<210> SEQ ID NO 21
<211> LENGTH: 339
<212> TYPE: DNA
<213> ORGANISM: Unknown
<220> FEATURE:
<223> OTHER INFORMATION: Description of Unknown:
      CD3-zeta sequence

<400> SEQUENCE: 21

agagtgaagt tcagcaggag cgcagacgcc cccgcgtacc agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgctaa                            339


<210> SEQ ID NO 22
<211> LENGTH: 251
<212> TYPE: PRT
<213> ORGANISM: Homo sapiens

<400> SEQUENCE: 22

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
```

```
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Gly Thr Lys Glu Arg Asp Trp Cys Gly Pro Ser Pro Ala
145                 150                 155                 160

Asp Leu Ser Pro Gly Ala Ser Ser Val Thr Pro Pro Ala Pro Ala Arg
                165                 170                 175

Glu Pro Gly His Ser Pro Gln Ile Ile Ser Phe Phe Leu Ala Leu Thr
            180                 185                 190

Ser Thr Ala Leu Leu Phe Leu Leu Phe Phe Leu Thr Leu Arg Phe Ser
        195                 200                 205

Trp Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu
                245                 250
```

<210> SEQ ID NO 23
<211> LENGTH: 42
<212> TYPE: PRT
<213> ORGANISM: Unknown
<220> FEATURE:
<223> OTHER INFORMATION: Description of Unknown:
      4-1BB sequence

<400> SEQUENCE: 23

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 24
<211> LENGTH: 126
<212> TYPE: DNA
<213> ORGANISM: Unknown
<220> FEATURE:
<223> OTHER INFORMATION: Description of Unknown:
      4-1BB sequence

<400> SEQUENCE: 24

```
aaacggggca gaaagaagct cctgtatata ttcaaacaac catttatgag accagtacaa      60

actactcaag aggaagatgg ctgtagctgc cgatttccag aagaagaaga aggaggatgt     120

gaactg                                                                126
```

<210> SEQ ID NO 25
<211> LENGTH: 276
<212> TYPE: PRT
<213> ORGANISM: Homo sapiens

<400> SEQUENCE: 25

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30
```

```
Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Trp Ser Ser Lys Pro Cys
65                  70                  75                  80

Lys Pro Cys Thr Trp Cys Asn Leu Arg Ser Gly Ser Glu Arg Lys Gln
                85                  90                  95

Leu Cys Thr Ala Thr Gln Asp Thr Val Cys Arg Cys Arg Ala Gly Thr
            100                 105                 110

Gln Pro Leu Asp Ser Tyr Lys Pro Gly Val Asp Cys Ala Pro Cys Pro
        115                 120                 125

Pro Gly His Phe Ser Pro Gly Asp Asn Gln Ala Cys Lys Pro Trp Thr
    130                 135                 140

Asn Cys Thr Leu Ala Gly Lys His Thr Leu Gln Pro Ala Ser Asn Ser
145                 150                 155                 160

Ser Asp Ala Ile Cys Glu Asp Arg Asp Pro Pro Ala Thr Gln Pro Gln
                165                 170                 175

Glu Thr Gln Gly Pro Pro Ala Arg Pro Ile Thr Val Gln Pro Thr Glu
            180                 185                 190

Ala Trp Pro Arg Thr Ser Gln Gly Pro Ser Thr Arg Pro Val Glu Val
        195                 200                 205

Pro Gly Gly Arg Ala Val Ala Ala Ile Leu Gly Leu Gly Leu Val Leu
    210                 215                 220

Gly Leu Leu Gly Pro Leu Ala Ile Leu Leu Ala Leu Tyr Leu Leu Arg
225                 230                 235                 240

Arg Asp Gln Arg Leu Pro Pro Asp Ala His Lys Pro Pro Gly Gly Gly
                245                 250                 255

Ser Phe Arg Thr Pro Ile Gln Glu Glu Gln Ala Asp Ala His Ser Thr
            260                 265                 270

Leu Ala Lys Ile
        275


<210> SEQ ID NO 26
<211> LENGTH: 196
<212> TYPE: PRT
<213> ORGANISM: Homo sapiens

<400> SEQUENCE: 26

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
```

```
        115                 120                 125

His Ile Tyr Glu Ser Gln Leu Cys Cys Gln Leu Lys Phe Trp Leu Pro
    130                 135                 140

Ile Gly Cys Ala Ala Phe Val Trp Cys Ile Leu Gly Cys Ile Leu Ile
145                 150                 155                 160

Cys Trp Leu Thr Lys Lys Lys Tyr Ser Ser Ser Val His Asp Pro Asn
                165                 170                 175

Gly Glu Tyr Met Phe Met Arg Ala Thr Ala Lys Lys Ser Arg Leu Thr
            180                 185                 190

Asp Val Thr Leu
        195


<210> SEQ ID NO 27
<211> LENGTH: 220
<212> TYPE: PRT
<213> ORGANISM: Homo sapiens

<400> SEQUENCE: 27

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Trp Leu Ala Ser
        35                  40                  45

Ser Arg Gly Ile Ala Ser Phe Val Cys Glu Tyr Ala Ser Pro Gly Lys
    50                  55                  60

Ala Thr Glu Val Arg Val Thr Val Leu Arg Gln Ala Asp Ser Gln Val
65                  70                  75                  80

Thr Glu Val Cys Ala Ala Thr Tyr Met Met Gly Asn Glu Leu Thr Phe
                85                  90                  95

Leu Asp Asp Ser Ile Cys Thr Gly Thr Ser Ser Gly Asn Gln Leu Thr
            100                 105                 110

Ile Gln Gly Leu Arg Ala Met Asp Thr Gly Leu Tyr Ile Cys Lys Val
        115                 120                 125

Glu Leu Met Tyr Pro Pro Pro Tyr Tyr Leu Gly Ile Gly Asn Gly Thr
    130                 135                 140

Gln Ile Tyr Val Ile Asp Pro Glu Pro Cys Pro Asp Ser Asp Phe Leu
145                 150                 155                 160

Leu Trp Ile Leu Ala Ala Val Ser Ser Gly Leu Phe Phe Tyr Ser Phe
                165                 170                 175

Leu Leu Thr Ala Val Ser Leu Ser Lys Met Leu Lys Lys Arg Ser Pro
            180                 185                 190

Leu Thr Thr Gly Val Tyr Val Lys Met Pro Pro Thr Glu Pro Glu Cys
        195                 200                 205

Glu Lys Gln Phe Gln Pro Tyr Phe Ile Pro Ile Asn
    210                 215                 220


<210> SEQ ID NO 28
<211> LENGTH: 286
<212> TYPE: PRT
<213> ORGANISM: Homo sapiens

<400> SEQUENCE: 28

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
```

```
            20                  25                  30

Asn Pro Pro Thr Phe Ser Pro Ala Leu Leu Trp Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Val Gly Trp Gly Gly Leu Leu
                165                 170                 175

Gly Ser Leu Val Leu Leu Val Trp Val Leu Ala Val Ile Cys Ser Arg
            180                 185                 190

Ala Ala Arg Gly Thr Ile Gly Ala Arg Arg Thr Gly Gln Pro Leu Lys
        195                 200                 205

Glu Asp Pro Ser Ala Val Pro Val Phe Ser Val Asp Tyr Gly Glu Leu
    210                 215                 220

Asp Phe Gln Trp Arg Glu Lys Thr Pro Glu Pro Pro Val Pro Cys Val
225                 230                 235                 240

Pro Glu Gln Thr Glu Tyr Ala Thr Ile Val Phe Pro Ser Gly Met Gly
                245                 250                 255

Thr Ser Ser Pro Ala Arg Arg Gly Ser Ala Asp Gly Pro Arg Ser Ala
            260                 265                 270

Gln Pro Leu Arg Pro Glu Asp Gly His Cys Ser Trp Pro Leu
        275                 280                 285


<210> SEQ ID NO 29
<211> LENGTH: 524
<212> TYPE: PRT
<213> ORGANISM: Homo sapiens

<400> SEQUENCE: 29

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Trp Trp
            20                  25                  30

Ala Gln Glu Gly Ala Pro Ala Gln Leu Pro Cys Ser Pro Thr Ile Pro
        35                  40                  45

Leu Gln Asp Leu Ser Leu Leu Arg Arg Ala Gly Val Thr Trp Gln His
    50                  55                  60

Gln Pro Asp Ser Gly Pro Pro Ala Ala Ala Pro Gly His Pro Leu Ala
65                  70                  75                  80

Pro Gly Pro His Pro Ala Ala Pro Ser Ser Trp Gly Pro Arg Pro Arg
                85                  90                  95

Arg Tyr Thr Val Leu Ser Val Gly Pro Gly Gly Leu Arg Ser Gly Arg
            100                 105                 110
```

-continued

```
Leu Pro Leu Gln Pro Arg Val Gln Leu Asp Glu Arg Gly Arg Gln Arg
        115                 120                 125

Gly Asp Phe Ser Leu Trp Leu Arg Pro Ala Arg Arg Ala Asp Ala Gly
    130                 135                 140

Glu Tyr Arg Ala Ala Val His Leu Arg Asp Arg Ala Leu Ser Cys Arg
145                 150                 155                 160

Leu Arg Leu Arg Leu Gly Gln Ala Ser Met Thr Ala Ser Pro Pro Gly
                165                 170                 175

Ser Leu Arg Ala Ser Asp Trp Val Ile Leu Asn Cys Ser Phe Ser Arg
            180                 185                 190

Pro Asp Arg Pro Ala Ser Val His Trp Phe Arg Asn Arg Gly Gln Gly
        195                 200                 205

Arg Val Pro Val Arg Glu Ser Pro His His His Leu Ala Glu Ser Phe
    210                 215                 220

Leu Phe Leu Pro Gln Val Ser Pro Met Asp Ser Gly Pro Trp Gly Cys
225                 230                 235                 240

Ile Leu Thr Tyr Arg Asp Gly Phe Asn Val Ser Ile Met Tyr Asn Leu
                245                 250                 255

Thr Val Leu Gly Leu Glu Pro Pro Thr Pro Leu Thr Val Tyr Ala Gly
            260                 265                 270

Ala Gly Ser Arg Val Gly Leu Pro Cys Arg Leu Pro Ala Gly Val Gly
        275                 280                 285

Thr Arg Ser Phe Leu Thr Ala Lys Trp Thr Pro Pro Gly Gly Gly Pro
    290                 295                 300

Asp Leu Leu Val Thr Gly Asp Asn Gly Asp Phe Thr Leu Arg Leu Glu
305                 310                 315                 320

Asp Val Ser Gln Ala Gln Ala Gly Thr Tyr Thr Cys His Ile His Leu
                325                 330                 335

Gln Glu Gln Gln Leu Asn Ala Thr Val Thr Leu Ala Ile Ile Thr Val
            340                 345                 350

Thr Pro Lys Ser Phe Gly Ser Pro Gly Ser Leu Gly Lys Leu Leu Cys
        355                 360                 365

Glu Val Thr Pro Val Ser Gly Gln Glu Arg Phe Val Trp Ser Ser Leu
    370                 375                 380

Asp Thr Pro Ser Gln Arg Ser Phe Ser Gly Pro Trp Leu Glu Ala Gln
385                 390                 395                 400

Glu Ala Gln Leu Leu Ser Gln Pro Trp Gln Cys Gln Leu Tyr Gln Gly
                405                 410                 415

Glu Arg Leu Leu Gly Ala Ala Val Tyr Phe Thr Glu Leu Ser Ser Pro
            420                 425                 430

Gly Ala Gln Arg Ser Gly Arg Ala Pro Gly Ala Leu Pro Ala Gly His
        435                 440                 445

Leu Leu Leu Phe Leu Ile Leu Gly Val Leu Ser Leu Leu Leu Leu Val
    450                 455                 460

Thr Gly Ala Phe Gly Phe His Leu Trp Arg Arg Gln Trp Arg Pro Arg
465                 470                 475                 480

Arg Phe Ser Ala Leu Glu Gln Gly Ile His Pro Pro Gln Ala Gln Ser
                485                 490                 495

Lys Ile Glu Glu Leu Glu Gln Glu Pro Glu Pro Glu Pro Glu Pro Glu
            500                 505                 510

Pro Glu Pro Glu Pro Glu Pro Glu Pro Glu Gln Leu
        515                 520
```

```
<210> SEQ ID NO 30
<211> LENGTH: 368
<212> TYPE: PRT
<213> ORGANISM: Homo sapiens

<400> SEQUENCE: 30

Met Leu Gly Gln Trp Thr Leu Ile Leu Leu Leu Leu Leu Lys Val Tyr
1               5                   10                  15

Gln Gly Lys Gly Cys Gln Gly Ser Ala Asp His Trp Ser Ile Ser Gly
            20                  25                  30

Val Pro Leu Gln Leu Gln Pro Asn Ser Ile Gln Thr Lys Val Asp Ser
        35                  40                  45

Ile Ala Trp Lys Lys Leu Leu Pro Ser Gln Asn Gly Phe His His Ile
    50                  55                  60

Leu Lys Trp Glu Asn Gly Ser Leu Pro Ser Asn Thr Ser Asn Asp Arg
65                  70                  75                  80

Phe Ser Phe Ile Val Lys Asn Leu Ser Leu Leu Ile Lys Ala Ala Gln
                85                  90                  95

Gln Gln Asp Ser Gly Leu Tyr Cys Leu Glu Val Thr Ser Ile Ser Gly
            100                 105                 110

Lys Val Gln Thr Ala Thr Phe Gln Val Phe Val Phe Glu Ser Leu Leu
        115                 120                 125

Pro Asp Lys Val Glu Lys Pro Arg Leu Gln Gly Gln Gly Lys Ile Leu
    130                 135                 140

Asp Arg Gly Arg Cys Gln Val Ala Leu Ser Cys Leu Val Ser Arg Asp
145                 150                 155                 160

Gly Asn Val Ser Tyr Ala Trp Tyr Arg Gly Ser Lys Leu Ile Gln Thr
                165                 170                 175

Ala Gly Asn Leu Thr Tyr Leu Asp Glu Glu Val Asp Ile Asn Gly Thr
            180                 185                 190

His Thr Tyr Thr Cys Asn Val Ser Asn Pro Val Ser Trp Glu Ser His
        195                 200                 205

Thr Leu Asn Leu Thr Gln Asp Cys Gln Asn Ala His Gln Glu Phe Arg
    210                 215                 220

Phe Trp Pro Phe Leu Val Ile Ile Val Ile Leu Ser Ala Leu Phe Leu
225                 230                 235                 240

Gly Thr Leu Ala Cys Phe Cys Val Trp Arg Arg Lys Arg Lys Glu Lys
                245                 250                 255

Gln Ser Glu Thr Ser Pro Lys Glu Phe Leu Thr Ile Tyr Glu Asp Val
            260                 265                 270

Lys Asp Leu Lys Thr Arg Arg Asn His Glu Gln Glu Gln Thr Phe Pro
        275                 280                 285

Gly Gly Gly Ser Thr Ile Tyr Ser Met Ile Gln Ser Gln Ser Ser Ala
    290                 295                 300

Pro Thr Ser Gln Glu Pro Ala Tyr Thr Leu Tyr Ser Leu Ile Gln Pro
305                 310                 315                 320

Ser Arg Lys Ser Gly Ser Arg Lys Arg Asn His Ser Pro Ser Phe Asn
                325                 330                 335

Ser Thr Ile Tyr Glu Val Ile Gly Lys Ser Gln Pro Lys Ala Gln Asn
            340                 345                 350

Pro Ala Arg Leu Ser Arg Lys Glu Leu Glu Asn Phe Asp Val Tyr Ser
        355                 360                 365


<210> SEQ ID NO 31
<211> LENGTH: 289
```

<212> TYPE: PRT
<213> ORGANISM: Homo sapiens

<400> SEQUENCE: 31

Met Lys Thr Leu Pro Ala Met Leu Gly Thr Gly Lys Leu Phe Trp Val
1 5 10 15

Phe Phe Leu Ile Pro Tyr Leu Asp Ile Trp Asn Ile His Gly Lys Glu
20 25 30

Ser Cys Asp Val Gln Leu Tyr Ile Lys Arg Gln Ser Glu His Ser Ile
35 40 45

Leu Ala Gly Asp Pro Phe Glu Leu Glu Cys Pro Val Lys Tyr Cys Ala
50 55 60

Asn Arg Pro His Val Thr Trp Cys Lys Leu Asn Gly Thr Thr Cys Val
65 70 75 80

Lys Leu Glu Asp Arg Gln Thr Ser Trp Lys Glu Glu Lys Asn Ile Ser
85 90 95

Phe Phe Ile Leu His Phe Glu Pro Val Leu Pro Asn Asp Asn Gly Ser
100 105 110

Tyr Arg Cys Ser Ala Asn Phe Gln Ser Asn Leu Ile Glu Ser His Ser
115 120 125

Thr Thr Leu Tyr Val Thr Asp Val Lys Ser Ala Ser Glu Arg Pro Ser
130 135 140

Lys Asp Glu Met Ala Ser Arg Pro Trp Leu Leu Tyr Arg Leu Leu Pro
145 150 155 160

Leu Gly Gly Leu Pro Leu Leu Ile Thr Thr Cys Phe Cys Leu Phe Cys
165 170 175

Cys Leu Arg Arg His Gln Gly Lys Gln Asn Glu Leu Ser Asp Thr Ala
180 185 190

Gly Arg Glu Ile Asn Leu Val Asp Ala His Leu Lys Ser Glu Gln Thr
195 200 205

Glu Ala Ser Thr Arg Gln Asn Ser Gln Val Leu Leu Ser Glu Thr Gly
210 215 220

Ile Tyr Asp Asn Asp Pro Asp Leu Cys Phe Arg Met Gln Glu Gly Ser
225 230 235 240

Glu Val Tyr Ser Asn Pro Cys Leu Glu Glu Asn Lys Pro Gly Ile Val
245 250 255

Tyr Ala Ser Leu Asn His Ser Val Ile Gly Pro Asn Ser Arg Leu Ala
260 265 270

Arg Asn Val Lys Glu Ala Pro Thr Glu Tyr Ala Ser Ile Cys Val Arg
275 280 285

Ser

<210> SEQ ID NO 32
<211> LENGTH: 10
<212> TYPE: PRT
<213> ORGANISM: Unknown
<220> FEATURE:
<223> OTHER INFORMATION: Description of Unknown:
PRAME sequence

<400> SEQUENCE: 32

Ala Leu Tyr Val Asp Ser Leu Phe Phe Leu
1 5 10

<210> SEQ ID NO 33
<211> LENGTH: 504
<212> TYPE: PRT

<213> ORGANISM: Homo sapiens

<400> SEQUENCE: 33

Met Glu Pro Ala Gly Pro Ala Pro Gly Arg Leu Gly Pro Leu Leu Cys
1 5 10 15

Leu Leu Leu Ala Ala Ser Cys Ala Trp Ser Gly Val Ala Gly Glu Glu
20 25 30

Glu Leu Gln Val Ile Gln Pro Asp Lys Ser Val Leu Val Ala Ala Gly
35 40 45

Glu Thr Ala Thr Leu Arg Cys Thr Ala Thr Ser Leu Ile Pro Val Gly
50 55 60

Pro Ile Gln Trp Phe Arg Gly Ala Gly Pro Gly Arg Glu Leu Ile Tyr
65 70 75 80

Asn Gln Lys Glu Gly His Phe Pro Arg Val Thr Thr Val Ser Asp Leu
85 90 95

Thr Lys Arg Asn Asn Met Asp Phe Ser Ile Arg Ile Gly Asn Ile Thr
100 105 110

Pro Ala Asp Ala Gly Thr Tyr Tyr Cys Val Lys Phe Arg Lys Gly Ser
115 120 125

Pro Asp Asp Val Glu Phe Lys Ser Gly Ala Gly Thr Glu Leu Ser Val
130 135 140

Arg Ala Lys Pro Ser Ala Pro Val Val Ser Gly Pro Ala Ala Arg Ala
145 150 155 160

Thr Pro Gln His Thr Val Ser Phe Thr Cys Glu Ser His Gly Phe Ser
165 170 175

Pro Arg Asp Ile Thr Leu Lys Trp Phe Lys Asn Gly Asn Glu Leu Ser
180 185 190

Asp Phe Gln Thr Asn Val Asp Pro Val Gly Glu Ser Val Ser Tyr Ser
195 200 205

Ile His Ser Thr Ala Lys Val Val Leu Thr Arg Glu Asp Val His Ser
210 215 220

Gln Val Ile Cys Glu Val Ala His Val Thr Leu Gln Gly Asp Pro Leu
225 230 235 240

Arg Gly Thr Ala Asn Leu Ser Glu Thr Ile Arg Val Pro Pro Thr Leu
245 250 255

Glu Val Thr Gln Gln Pro Val Arg Ala Glu Asn Gln Val Asn Val Thr
260 265 270

Cys Gln Val Arg Lys Phe Tyr Pro Gln Arg Leu Gln Leu Thr Trp Leu
275 280 285

Glu Asn Gly Asn Val Ser Arg Thr Glu Thr Ala Ser Thr Val Thr Glu
290 295 300

Asn Lys Asp Gly Thr Tyr Asn Trp Met Ser Trp Leu Leu Val Asn Val
305 310 315 320

Ser Ala His Arg Asp Asp Val Lys Leu Thr Cys Gln Val Glu His Asp
325 330 335

Gly Gln Pro Ala Val Ser Lys Ser His Asp Leu Lys Val Ser Ala His
340 345 350

Pro Lys Glu Gln Gly Ser Asn Thr Ala Ala Glu Asn Thr Gly Ser Asn
355 360 365

Glu Arg Asn Ile Tyr Ile Val Val Gly Val Val Cys Thr Leu Leu Val
370 375 380

Ala Leu Leu Met Ala Ala Leu Tyr Leu Val Arg Ile Arg Gln Lys Lys
385 390 395 400

```
Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500


<210> SEQ ID NO 34
<211> LENGTH: 118
<212> TYPE: PRT
<213> ORGANISM: Homo sapiens

<400> SEQUENCE: 34

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115


<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80
```

```
Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115


<210> SEQ ID NO 36
<211> LENGTH: 34
<212> TYPE: PRT
<213> ORGANISM: Unknown
<220> FEATURE:
<223> OTHER INFORMATION: Description of Unknown:
      SIRP-alpha signal sequence

<400> SEQUENCE: 36

Met Gly Ser Thr Met Glu Pro Ala Gly Pro Ala Pro Gly Arg Leu Gly
1               5                   10                  15

Pro Leu Leu Cys Leu Leu Leu Ala Ala Ser Cys Ala Trp Ser Gly Val
            20                  25                  30

Ala Gly


<210> SEQ ID NO 37
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ser Gly Ala Thr Asn Phe Ser Leu Leu Lys Gln Ala Gly Asp Val
1               5                   10                  15

Glu Glu Asn Pro Gly Pro Met Gly Ser Thr Met Glu Pro Ala Gly Pro
            20                  25                  30

Ala Pro Gly Arg Leu Gly Pro Leu Leu Cys Leu Leu Leu Ala Ala Ser
        35                  40                  45

Cys Ala Trp Ser Gly Val Ala Gly Glu Glu Glu Leu Gln Ile Ile Gln
    50                  55                  60

Pro Asp Lys Ser Val Leu Val Ala Ala Gly Glu Thr Ala Thr Leu Arg
65                  70                  75                  80

Cys Thr Ile Thr Ser Leu Phe Pro Val Gly Pro Ile Gln Trp Phe Arg
                85                  90                  95

Gly Ala Gly Pro Gly Arg Val Leu Ile Tyr Asn Gln Arg Gln Gly Pro
            100                 105                 110

Phe Pro Arg Val Thr Thr Val Ser Asp Thr Thr Lys Arg Asn Asn Met
        115                 120                 125

Asp Phe Ser Ile Arg Ile Gly Asn Ile Thr Pro Ala Asp Ala Gly Thr
    130                 135                 140

Tyr Tyr Cys Ile Lys Phe Arg Lys Gly Ser Pro Asp Asp Val Glu Phe
145                 150                 155                 160

Lys Ser Gly Ala Gly Thr Glu Leu Ser Val Arg Ala Lys Pro Ser Tyr
                165                 170                 175

Pro Tyr Asp Val Pro Asp Tyr Ala
            180


<210> SEQ ID NO 38
<211> LENGTH: 566
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 38

```
ggaagcggag ctactaactt cagcctgctg aagcaggctg gagacgtgga ggagaaccct     60

ggacctatgg gatccaccat ggaacctgct ggtcccgctc cgggccgcct gggaccactc    120

ctttgccttc tcttggctgc atcttgtgcc tggagtggag tcgcaggaga ggaagagctc    180

cagatcatac agcccgataa gtccgttctt gtagcggctg gcgagactgc cactctcaga    240

tgcactatca caagcctttt tcccgtgggg cctattcagt ggtttcgcgg ggcaggcccg    300

ggcagggtac ttatctacaa tcagcgacag ggcccattcc cccgagtaac cacagtgagc    360

gataccacca aacggaacaa tatggacttt agtattcgga tcggtaacat aaccccccgca    420

gacgcaggca cgtactattg tatcaaattc cgcaagggaa gccccgacga tgtggagttt    480

aaatctggtg ctggcactga actgtccgtt cgagcgaagc catcataccc ctacgacgtt    540

cctgattacg cctagtagga attcac                                          566
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Ser Lys Asp Thr Ser Lys Asn Gln
65                  70                  75                  80

Val Phe Leu Lys Ile Ala Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Ser Val Thr Val Ser Ser
        115                 120
```

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30
```

```
Asn Gly Asn Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110
```

<210> SEQ ID NO 41
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Ser Lys Asp Thr Ser Lys Asn Gln
65                  70                  75                  80

Val Phe Leu Lys Ile Ala Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Ser Val Thr Val Ser Ser Gly Gly Gly Gly Ser
        115                 120                 125

Gly Gly Gly Gly Ser Gly Gly Gly Gly Ser Asp Ile Val Met Thr Gln
    130                 135                 140

Ala Ala Pro Ser Val Pro Val Thr Pro Gly Glu Ser Val Ser Ile Ser
145                 150                 155                 160

Cys Arg Ser Ser Lys Ser Leu Leu His Ser Asn Gly Asn Thr Tyr Leu
                165                 170                 175

Tyr Trp Phe Leu Gln Arg Pro Gly Gln Ser Pro Gln Arg Leu Ile Tyr
            180                 185                 190

Tyr Met Ser Asn Leu Ala Ser Gly Val Pro Asp Arg Phe Ser Gly Arg
        195                 200                 205

Gly Ser Gly Thr Asp Phe Thr Leu Arg Ile Ser Arg Val Glu Ala Glu
    210                 215                 220

Asp Val Gly Val Tyr Tyr Cys Met Gln Ser Leu Glu Tyr Pro Leu Thr
225                 230                 235                 240

Phe Gly Gly Gly Thr Lys Leu Glu Ile Lys
                245                 250
```

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Val Lys Leu Gln Glu Ser Gly Gly Gly Phe Val Lys Pro Gly Gly Ser
1 5 10 15

Leu Lys Val Ser Cys Ala Ala Ser Gly Phe Thr Phe Ser Ser Tyr Ala
20 25 30

Met Ser Trp Val Arg Leu Ser Pro Glu Met Arg Leu Glu Trp Val Ala
35 40 45

Thr Ile Ser Ser Ala Gly Gly Tyr Ile Phe Tyr Ser Asp Ser Val Gln
50 55 60

Gly Arg Phe Thr Ile Ser Arg Asp Asn Ala Lys Asn Thr Leu His Leu
65 70 75 80

Gln Met Gly Ser Leu Arg Ser Gly Asp Thr Ala Met Tyr Tyr Cys Ala
85 90 95

Arg Gln Gly Phe Gly Asn Tyr Gly Asp Tyr Tyr Ala Met Asp Tyr Trp
100 105 110

Gly Gln Gly Thr Thr Val Thr Val Ser Ser
115 120

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Asp Ile Glu Leu Thr Gln Ser Pro Ser Ser Leu Ala Val Ser Ala Gly
1 5 10 15

Glu Lys Val Thr Met Ser Cys Lys Ser Ser Gln Ser Leu Leu Asn Ser
20 25 30

Arg Thr Arg Lys Asn Gln Leu Ala Trp Tyr Gln Gln Lys Pro Gly Gln
35 40 45

Ser Pro Glu Leu Leu Ile Tyr Trp Ala Ser Thr Arg Gln Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Gln
85 90 95

Ser Tyr Asn Leu Leu Thr Phe Gly Pro Gly Thr Lys Leu Glu Val Lys
100 105 110

Arg

<210> SEQ ID NO 44
<211> LENGTH: 250
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Val Lys Leu Gln Glu Ser Gly Gly Gly Phe Val Lys Pro Gly Gly Ser
1 5 10 15

Leu Lys Val Ser Cys Ala Ala Ser Gly Phe Thr Phe Ser Ser Tyr Ala

-continued

```
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Pro Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Val Lys Arg
                245                 250


<210> SEQ ID NO 45
<211> LENGTH: 4
<212> TYPE: PRT
<213> ORGANISM: Homo sapiens

<400> SEQUENCE: 45

Tyr Val Lys Met
1


<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5
```

COMPOSITIONS AND METHODS FOR ADOPTIVE CELL THERAPY FOR CANCER

CROSS REFERENCE TO RELATED APPLICATIONS

This application is a U.S. National Stage Application under 35 U.S.C. § 371 of International Application Serial No. PCT/US2019/060995, filed on Nov. 12, 2019, which claims the benefit under 35 U.S.C. § 119(e) of U.S. Provisional Application Ser. No. 62/760,864, filed Nov. 13, 2018, the contents of each of which are incorporated by reference herein in their entirety including all figures and tables.

STATEMENT OF GOVERNMENT SUPPORT

This invention was made with government support under CA023766 and CA055349 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 3, 2019, is named 115872-0496_SL.txt and is 62,211 bytes in size.

BACKGROUND OF THE INVENTION

Chimeric antigen receptor (CAR) T cell therapy redirects T cells to activate in the presence of, and subsequently kill, an antigen-expressing cell. This is achieved by coupling an antigen-specific single-chain variable fragment (scFv) to endogenous T cell activation signaling domains. CAR therapy has shown promise for treating hematopoietic malignancies, however, relapse of antigen-negative tumors remains a significant complication for these patients. Further, little success has been seen in treating solid tumors, which is largely attributed to immunosuppressive tumor microenvironments.

Combination therapy with CAR T cells and checkpoint blockade is a popular approach to combat these issues. Checkpoint blockade therapy antagonizes the signaling pathways that act as the 'brakes' on the immune system. Current combinations focus on altering T cell-tumor interactions, but recent studies show promise also in abrogating innate immune checkpoints, specifically the CD47-SIRPα signaling axis. This pathway, commonly referred to as the "do not eat me" signal, prevents macrophage phagocytosis and cross priming of T cells by dendritic cells, and is thus involved in both innate and adaptive immune processes. However, early stage clinical trials of anti-CD47 agents show severe toxicities.

Thus, there is a need for new methods to increase the efficacy of CAR T cell therapy in solid tumors and to prevent antigen loss relapse in hematologic tumors and to reduce potential toxicities relating to immune checkpoint blockade.

SUMMARY OF THE INVENTION

Provided herein, in certain embodiments, are compositions and methods for adoptive cell therapy comprising engineered immune cells that express a SIRPα polypeptide and a receptor that binds to a target antigen. In some embodiments, the receptor is a T cell receptor. In some embodiments, the receptor is a native receptor (e.g. a native T cell receptor). In some embodiments, the receptor is a non-native receptor (e.g. a non-native T cell receptor), for example, an engineered receptor, such as a chimeric antigen receptor (CAR). In some embodiments, the receptor is a non-native receptor such as a truncated receptor, a genetically modified receptor, a TCR mimic receptor, an antibody, or other ligand capable of interacting with a target cell. In some embodiments, the engineered immune cells comprise a soluble SIRPα polypeptide and/or a nucleic acid encoding the soluble SIRPα polypeptide. In some embodiments, the engineered immune cells comprise a membrane-bound SIRPα polypeptide and/or a nucleic acid encoding the membrane-bound SIRPα polypeptide. In some embodiments, the engineered immune cells comprise a chimeric antigen receptor and/or nucleic acid encoding the chimeric antigen receptor. In some embodiments, the nucleic acid encoding the SIRPα polypeptide comprises a signal peptide for secretion of the SIRPα polypeptide. In some embodiments, the SIRPα polypeptide comprises a transmembrane domain for insertion of the SIRPα polypeptide into the plasma membrane. In some embodiments, the SIRPα polypeptide is wild-type SIRPα or a fragment thereof. In some embodiments, the SIRPα polypeptide is CV1. In some embodiments, the nucleic acid encoding a SIRPα polypeptide is operably linked to a promoter. In some embodiments, the promoter is a constitutive promoter. In some embodiments, the promoter is a conditional promoter. In some embodiments, the conditional promoter is inducible by binding of the receptor (e.g., a CAR) to an antigen, such as a tumor antigen. In some embodiments, the chimeric antigen receptor comprises (i) an extracellular antigen binding domain; (ii) a transmembrane domain; and (iii) an intracellular domain. In some embodiments, the extracellular antigen binding domain binds to an antigen expressed on normal healthy cells. In some embodiments, the extracellular antigen binding domain binds to an extracellular antigen. In some embodiments, the extracellular antigen binding domain binds to a tumor antigen. In some embodiments, the tumor antigen is selected from among BCMA, CD19, mesothelin, MUC16, PSCA, WT1, and PRAME. In some embodiments, the extracellular antigen binding domain comprises a single chain variable fragment (scFv). In some embodiments, the extracellular antigen binding domain comprises a human scFv. In some embodiments, the extracellular antigen binding domain comprises a CD19 scFv of SEQ ID NO: 3. In some embodiments, the extracellular antigen binding domain comprises a CD19 scFv having at least 80%, 85%, 90%, 95%, 96%, 97%, 98%, or 99% sequence identity to SEQ ID NO: 3. In some embodiments, the extracellular antigen binding domain comprises a MUC16 scFv of SEQ ID NO: 41 or 44. In some embodiments, the extracellular antigen binding domain comprises a MUC16 scFv having at least 80%, 85%, 90%, 95%, 96%, 97%, 98%, or 99% sequence identity to SEQ ID NO: 41 or 44. In some embodiments, the extracellular antigen binding domain comprises a signal peptide that is covalently joined to the N-terminus of the extracellular antigen-binding domain. In some embodiments, the transmembrane domain comprises a CD8 transmembrane domain. In some embodiments, the intracellular domain comprises a costimulatory domain. In some embodiments, the one or more costimulatory domains are selected from a CD28 costimulatory domain, a CD3ζ-chain, a 4-1BBL costimulatory domain, or any combination thereof. In some embodiments, the immune cell is a lymphocyte. In some embodiments, the lymphocyte is a T-cell, a B cell or a natural killer (NK) cell. In some embodiments, the T cell is a CD4+ T cell or a CD8+ T cell. In some embodiments, the immune cell is a tumor infiltrating lymphocyte. In some embodiments, the immune cell is derived from an autologous donor or an allogenic donor.

Also provided are polypeptides comprising a SIRPα polypeptide and a chimeric antigen receptor. In some embodiments, the SIRPα polypeptide is a soluble SIRPα polypeptide. In some embodiments, the SIRPα polypeptide is a membrane-bound SIRPα polypeptide. In some embodiments, the polypeptides further comprise a self-cleaving peptide located between the SIRPα polypeptide and the chimeric antigen receptor. In some embodiments, the self-cleaving peptide is a P2A self-cleaving peptide. In some embodiments, the SIRPα polypeptide comprises a signal peptide for secretion of the SIRPα polypeptide. In some embodiments, the SIRPα polypeptide comprises a transmembrane domain for insertion of the SIRPα polypeptide into the plasma membrane. In some embodiments, the SIRPα polypeptide is wild-type SIRPα or a fragment thereof. In some embodiments, the SIRPα polypeptide is CV1. In some embodiments, the chimeric antigen receptor comprises (i) an antigen binding domain; (ii) a transmembrane domain; and (iii) an intracellular domain. In some embodiments, the extracellular antigen binding domain binds to an antigen expressed on normal healthy cells. In some embodiments, the extracellular antigen binding domain binds to an extracellular antigen. In some embodiments, the antigen binding domain binds to a tumor antigen. In some embodiments, the tumor antigen is selected from among from among BCMA, CD19, mesothelin, MUC16, PSCA, WT1, and PRAME. In some embodiments, the antigen binding domain comprises a single chain variable fragment (scFv). In some embodiments, the extracellular antigen binding domain comprises a CD19 scFv of SEQ ID NO: 3. In some embodiments, the extracellular antigen binding domain comprises a CD19 scFv having at least 80%, 85%, 90%, 95%, 96%, 97%, 98%, or 99% sequence identity to SEQ ID NO: 3. In some embodiments, the extracellular antigen binding domain comprises a MUC16 scFv of SEQ ID NO: 41 or 44. In some embodiments, the extracellular antigen binding domain comprises a MUC16 scFv having at least 80%, 85%, 90%, 95%, 96%, 97%, 98%, or 99% sequence identity to SEQ ID NO: 41 or 44. In some embodiments, the transmembrane domain comprises a CD8 transmembrane domain. In some embodiments, the intracellular domain comprises a one or more costimulatory domains. In some embodiments, the one or more costimulatory domains are selected from a CD28 costimulatory domain, a CD3ζ-chain, a 4-1BBL costimulatory domain, or any combination thereof.

Also provided are nucleic acids encoding any of polypeptides disclosed herein. In some embodiments, the nucleic acid encoding the polypeptide is operable linked to a promoter. In some embodiments, the promoter is a constitutive promoter. In some embodiments, the promoter is a conditional promoter. In some embodiments, the conditional promoter is inducible by the CAR binding to an antigen.

Also provided are vectors comprising any of nucleic acids disclosed herein. In some embodiments, the vector is a viral vector or a plasmid. In some embodiments, the vector is a retroviral vector.

Also provided are host cells comprising a polypeptide, a nucleic acid, or a vector disclosed herein.

Also provided are methods for treating cancer in a subject in need thereof comprising administering an effective amount of any of the engineered immune cells provided herein. In some embodiments, the methods further comprise administering to the subject a monoclonal antibody. Also provided herein are methods for treating of inhibiting tumor growth or metastasis in a subject comprising contacting a tumor cell with an effective amount of any of the engineered immune cells provided herein. In some embodiments, the methods further comprise administering to the subject a monoclonal antibody. In some embodiments, the antibody is administered subsequent to administration of the engineered immune cells. Alternatively, the monoclonal antibody may be administered prior to the administration of the engineered immune cells. In another alternative, the monoclonal antibody may be administered simultaneously with the administration of the engineered immune cells. In some embodiments, the engineered immune cells are administered are administered intravenously, intraperitoneally, subcutaneously, intramuscularly, or intratumorally. In some embodiments, the cancer or tumor is a carcinoma, sarcoma, a melanoma, or a hematopoietic cancer. In some embodiments, the cancer or tumor is selected from among adrenal cancers, bladder cancers, blood cancers, bone cancers, brain cancers, breast cancers, carcinoma, cervical cancers, colon cancers, colorectal cancers, corpus uterine cancers, ear, nose and throat (ENT) cancers, endometrial cancers, esophageal cancers, gastrointestinal cancers, head and neck cancers, Hodgkin's disease, intestinal cancers, kidney cancers, larynx cancers, leukemias, liver cancers, lymph node cancers, lymphomas, lung cancers, melanomas, mesothelioma, myelomas, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof. In some embodiments, the methods further comprise administering an additional cancer therapy. In some embodiments, the additional cancer therapy is selected from among chemotherapy, radiation therapy, immunotherapy, monoclonal antibodies, anti-cancer nucleic acids or proteins, anti-cancer viruses or microorganisms, and any combinations thereof. In some embodiments, the methods further comprise administering a cytokine to the subject. In some embodiments, the cytokine is administered prior to, during, or subsequent to administration of the one or more engineered immune cells. In some embodiments, the cytokine is selected from a group consisting of interferon α, interferon 3, interferon 7, complement C5a, IL-2, TNFalpha, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2.

Also provided are methods for preparing immune cells for cancer therapy, comprising isolating immune cells from a donor subject, transducing the immune cells (e.g., T cells) with (a) a nucleic acid encoding a SIRPα polypeptide, (b) a nucleic acid provided herein, or (c) a vector provided herein. In some embodiments, the SIRPα polypeptide is a soluble SIRPα polypeptide. In some embodiments, the SIRPα polypeptide is a membrane-bound SIRPα polypeptide. In some embodiments, the immune cells isolated from the donor subject comprise one or more lymphocytes. In some embodiments, the lymphocytes comprise a T-cell, a B cell, and/or a natural killer (NK) cell. In some embodiments, the T cell is a CD4+ T cell or a CD8+ T cell. In some embodiments, the immune cells isolated from the donor subject comprise tumor infiltrating lymphocytes (TILs).

Also provided are methods for treatment comprising isolating immune cells from a donor subject, transducing the immune cells with a nucleic acid encoding a SIRPα polypeptide and optionally, a nucleic acid encoding an antigen-targeted receptor or a vector comprising a nucleic acid encoding a SIRPα polypeptide and optionally, a nucleic acid encoding an antigen-targeted receptor, and administering the transduced immune cells to a recipient subject. In some embodiments, the SIRPα polypeptide is a soluble SIRPα polypeptide. In some embodiments, the SIRPα polypeptide is a membrane-bound SIRPα polypeptide. In some embodiments, the donor subject and the recipient subject are the same (i.e., autologous). In some embodiments, the donor subject and the recipient subject are different (i.e., allogenic). In some embodiments, the immune cells isolated from the donor subject comprise one or more lymphocytes. In some embodiments, the lymphocytes comprise a T-cell, a B cell, and/or a natural killer (NK) cell. In some embodiments, the T cell is a CD4+ T cell or a CD8+ T cell. In some embodiments, the immune cells isolated from the donor subject comprise tumor infiltrating lymphocytes (TILs).

Also provided are uses of any of the engineered immune cells provided herein for treating a cancer.

Also provided are uses of any of the engineered immune cells provided herein the preparation of a medicament for the treatment of a cancer.

BRIEF DESCRIPTION OF THE DRAWINGS

FIG. 2A shows raw bioluminescent images on a standardized scale taken on Days 6, 15, 23, and 30. Tumor burden was quantified on Day 30 and FIG. 2B shows that HEK-secreted CV1 is functional and can potentiate mAb therapy. $p<0.01$, **$p<0.0001$.

FIG. 6A shows the schematic for the sandwich ELISA. Secreted CV1 was quantified by absorbance at 450 nm using TMB substrate and sulfuric acid to quench the reaction and the results are shown in FIG. 6B. Concentration of CV1 was analyzed by interpolation of a standard curve, made using recombinant CV1-HA. The results are shown in FIG. 6C. FIG. 6D shows that antigen stimulation of the CAR leads to a 10-fold increase in OrexiCAR-secreted CV1.

FIG. 11A shows a comparison between the untreated control and the rituximab treatment groups, FIG. 11B shows a comparison between the CD19

OrexiCAR and CD19 CAR treatment groups, and FIG. 11C shows a comparison between CD19 OrexiCAR+rituximab and CD19 CAR+rituximab.

DETAILED DESCRIPTION OF THE INVENTION

Figure 1:
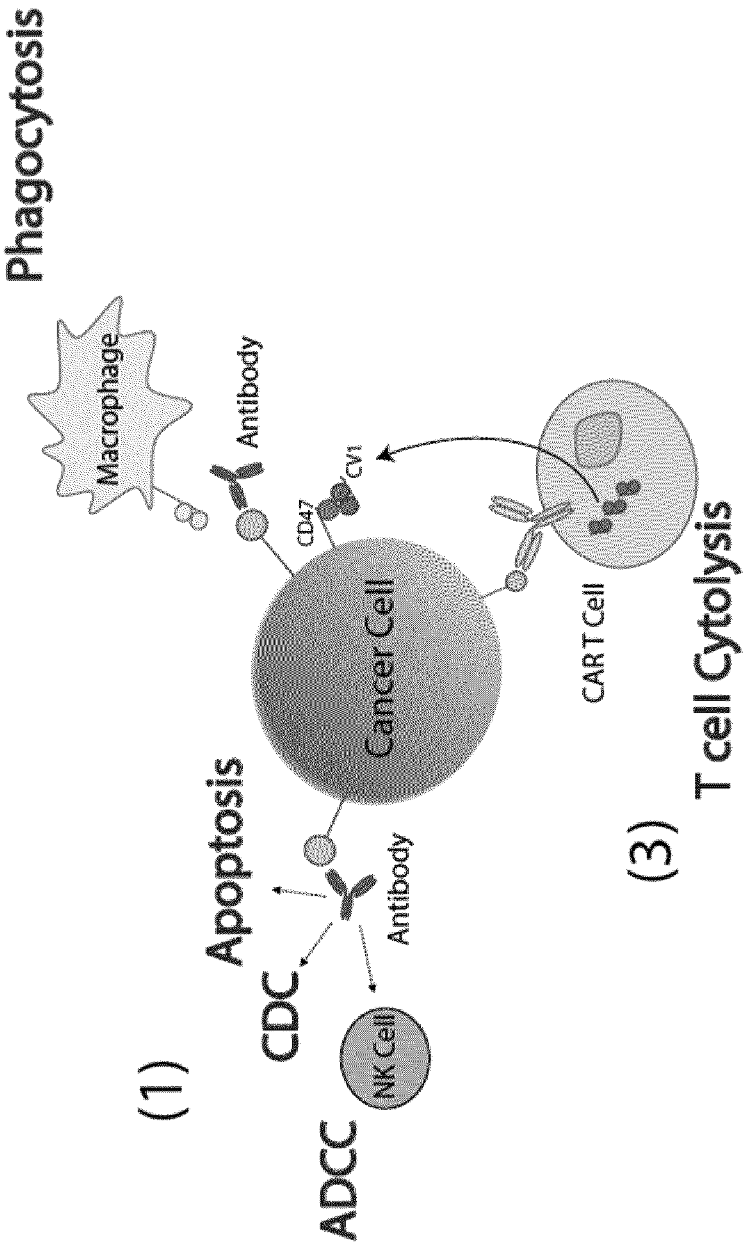
FIG. 1 provides an overview of the killing mechanisms of OrexiCAR therapy. OrexiCAR therapy can kill a tumor through three different arms: 1) Antibody-mediated mechanisms including ADCC, CDC apoptosis, 2) SIRPα polypeptide-enhancement of antibody dependent cellular phagocytosis (ADCP), and 3) CAR T cell-mediated cytolysis.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a" "an" and "the" are intended to include the plural forms as well, unless the context clearly indicates otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "administration" of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells, at least about 10,000 cells, at least about 100,000 cells, at least about $1\times10^6$ cells, at least about $1\times10^7$ cells, at least about $1\times10^8$ cells, at least about $1\times10^9$ cells, at least about $1\times10^{10}$ cells, at least about $1\times10^{11}$ cells, at least about $1\times10^{12}$ cells, or more cells expressing similar or different phenotypes.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form, and a second plurality of amino acids are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight, and tolerance to drugs. It can also depend on the degree, severity, and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein the term "immune cell" refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

As used herein, the term "native immune cell" refers to an immune cell that naturally occurs in the immune system.

As used herein, the term "engineered immune cell" refers to an immune cell that is genetically modified.

The term "lymphocyte" refers to all immature, mature, undifferentiated, and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells, and anergic AN1/T3 cell populations.

As used herein, the term "T-cell" includes naïve T cells, CD4+ T cells, CD8+ T cells, memory T cells, activated T cells, anergic T cells, tolerant T cells, chimeric B cells, and antigen-specific T cells.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e. heterologous T-cell receptor) modified lymphocytes and CAR (i.e. chimeric antigen receptor) modified lymphocytes. In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells.

As used herein "tumor-infiltrating lymphocytes" or TILs refer to white blood cells that have left the bloodstream and migrated into a tumor.

As used herein, the term “antibody” means not only intact antibody molecules, but also fragments of antibody molecules that retain immunogen-binding ability. Such fragments are also well known in the art and are regularly employed both in vitro and in vivo. Accordingly, as used herein, the term “antibody” means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the invention comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nanobodies and single domain camelid antibodies), VNAR fragments, Bi-specific T-cell engager (BiTE) antibodies, minibodies, disulfide-linked Fvs (sdFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA, and IgY), class (e.g., IgG1, IgG2, IgG3, IgG4, IgA1, and IgA2), or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CHI, CH2, and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Cl q) of the classical complement system. As used herein interchangeably, the terms “antigen-binding portion”, “antigen-binding fragment”, or “antigen-binding region” of an antibody, refer to the region or portion of an antibody that binds to the antigen and which confers antigen specificity to the antibody; fragments of antigen-binding proteins, for example, antibodies include one or more fragments of an antibody that retain the ability to specifically bind to an antigen (e.g., a peptide/HLA complex). It has been shown that the antigen-binding function of an antibody can be performed by fragments of a full-length antibody. Examples of antigen-binding portions encompassed within the term “antibody fragments” of an antibody include a Fab fragment, a monovalent fragment consisting of the $V_L$, $V_H$, $C_L$ and CHI domains; a $F(ab)_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., *Nature* 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, and urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., *Science* 242:423-426 (1988); and Huston et al., *Proc. Natl. Acad. Sci.* 85: 5879-5883 (1988). These antibody fragments are obtained using conventional techniques known to those of ordinary skill in the art, and the fragments are screened for utility in the same manner as are intact antibodies.

An “isolated antibody” or “isolated antigen-binding protein” is one which has been identified and separated and/or recovered from a component of its natural environment. “Synthetic antibodies” or “recombinant antibodies” are generally generated using recombinant technology or using peptide synthetic techniques known to those of skill in the art.

As used herein, the term “single-chain variable fragment” or “scFv” is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. In certain embodiments, the linker comprises amino acids having the sequence set forth in SE ID NO: 1 as provided below.

(SEQ ID NO: 1)

GGGGSGGGGSGGGGS

In certain embodiments, the nucleic acid sequence encoding the amino acid sequence of SEQ ID NO: 1 is set forth in SEQ ID NO: 2, which is provided below: ggcggcggcggatctggaggtggtggctcaggtggcggaggctcc (SEQ ID NO: 2).

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (*Proc. Nat. Acad. Sci. USA,* 85:5879-5883 (1988)). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hybridoma* (Larchmt) 27(6):455-51 (2008); Peter et al., *J Cachexia*

*Sarcopenia Muscle* (2012); Shieh et al., *J Imunol* 183(4): 2277-85 (2009); Giomarelli et al., *Thromb Haemost* 97(6): 955-63 (2007); Fife eta., *J Clin Invst* 116(8):2252-61 (2006); Brocks et al., *Immunotechnology* 3(3): 173-84 (1997); Moosmayer et al., *Ther Immunol* 2(10):31-40 (1995) Agonistic scFvs having stimulatory activity have been described (see, e.g., Peter et al., *J Biol Chem* 25278(38):36740-7 (2003); Xie et al., *Nat Biotech* 15(8):768-71 (1997); Ledbetter et al., *Crit Rev Immunol* 17(5-6):427-55 (1997); Ho et al., *Bio Chim Biophys Acta* 1638(3):257-66 (2003)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "$F(ab')_2$" refers to an antibody fragment generated by pepsin digestion of whole IgG antibodies, wherein this fragment has two antigen binding (ab') (bivalent) regions, wherein each ($ab^1$) region comprises two separate amino acid chains, a part of a H chain and a light (L) chain linked by an S—S bond for binding an antigen and where the remaining H chain portions are linked together. A "$F(ab')_2$" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. Sequences of Proteins of Immunological Interest, Fifth Edition, U.S. Department of Health and Human Services, NIH Publication No. 91-3242(1991)).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, *Methods Enzymol.* 152:399 (1987); Kimmel, A. R. *Methods Enzymol.* 152:507 (1987)).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% w/v formamide, and more preferably at least about 50% w/v formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% w/v SDS. In certain embodiments, hybridization will occur at 37° C. in 500 mM NaCl, 50 mM trisodium citrate, 1% w/v SDS, 35% w/v formamide, and 100 μg/ml denatured salmon sperm DNA (ssDNA). In certain embodiments, hybridization will occur at 42° C. in 250 mM NaCl, 25 mM trisodium citrate, 1% w/v SDS, 50% w/v formamide, and 200 μg ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In certain embodiments, wash steps will occur at 25° C. in 30 mM NaCl, 3 mM trisodium citrate, and 0.1% w/v SDS. In certain embodiments, wash steps will occur at 42° C. in 15 mM NaCl, 1.5 mM trisodium citrate, and 0.1% w/v SDS. In certain embodiments, wash steps will occur at 68° C. in 15 mM NaCl, 1.5 mM trisodium citrate, and 0.1% w/v SDS. Additional variations on these conditions will be readily apparent to those skilled in the art. Hybridization techniques are well known to those skilled in the art and are described, for example, in Benton and Davis (*Science* 196: 180 (1977)); Grunstein and Rogness (*Proc. Natl. Acad. Sci., USA* 72:3961 (1975)); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $^{e-100}$ indicating a closely related sequence.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (*Comput. Appl. Biosci.,* 4:1 1-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (*J. Mol. Biol.* 48:444-453 (1970)) algorithm which has been incorporated into the GAP program in the GCG software package (available at world wide web.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally, or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) *J. Mol. Biol.* 215: 403-10. BLAST protein searches can be performed with the XBLAST program, score=50, wordlength=3 to obtain amino acid sequences homologous to the specified sequences disclosed herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions, and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine; negatively-charged amino acids include aspartic acid and glutamic acid; and neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

As used herein, the term "ligand" refers to a molecule that binds to a receptor. In particular, the ligand binds a receptor on another cell, allowing for cell-to-cell recognition and/or interaction.

As used herein, the term, "co-stimulatory signaling domain," or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD28 and 4-1BB, other costimulatory domains are contemplated for use with the CARs described herein. The inclusion of one or more co-stimulatory signaling domains can enhance the efficacy and expansion of T cells expressing CAR receptors. The intracellular signaling and co-stimulatory signaling domains can be linked in any order in tandem to the carboxyl terminus of the transmembrane domain.

As used herein, the term "chimeric co-stimulatory receptor" or "CCR" refers to a chimeric receptor that binds to an antigen and provides co-stimulatory signals, but does not provide a T-cell activation signal.

As used herein, regulatory region of a nucleic acid molecule means a cis-acting nucleotide sequence that influences expression, positively or negatively, of an operatively linked gene. Regulatory regions include sequences of nucleotides that confer inducible (i.e., require a substance or stimulus for increased transcription) expression of a gene. When an inducer is present or at increased concentration, gene expression can be increased. Regulatory regions also include sequences that confer repression of gene expression (i.e., a substance or stimulus decreases transcription). When a repressor is present or at increased concentration gene expression can be decreased. Regulatory regions are known to influence, modulate or control many in vivo biological activities including cell proliferation, cell growth and death, cell differentiation and immune modulation. Regulatory regions typically bind to one or more trans-acting proteins, which results in either increased or decreased transcription of the gene.

Particular examples of gene regulatory regions are promoters and enhancers. Promoters are sequences located around the transcription or translation start site, typically positioned 5' of the translation start site. Promoters usually are located within 1 Kb of the translation start site, but can be located further away, for example, 2 Kb, 3 Kb, 4 Kb, 5 Kb or more, up to and including 10 Kb. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, but are not limited to, in addition to promoter regions, sequences that facilitate translation, splicing signals for introns, maintenance of the correct reading frame of the gene to permit in-frame translation of mRNA and, stop codons, leader sequences and fusion partner sequences, internal ribosome binding site (IRES) elements for the creation of multigene, or polycistronic, messages, polyadenylation signals to provide proper polyadenylation of the transcript of a gene of interest and stop codons, and can be optionally included in an expression vector.

As used herein, "operably linked" with reference to nucleic acid sequences, regions, elements or domains means that the nucleic acid regions are functionally related to each other. For example, nucleic acid encoding a leader peptide can be operably linked to nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods. As used herein, production by recombinant means by using recombinant DNA methods means the use of the well-known methods of molecular biology for expressing proteins encoded by cloned DNA.

As used herein, a "host cell" is a cell that is used in to receive, maintain, reproduce and amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, a vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, the term "disease" refers to any condition or disorder that damages or interferes with the normal function of a cell, tissue, or organ. Examples of diseases include neoplasia or pathogen infection of cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasia), or otherwise reduce the pathological consequences of the disease (e.g., a neoplasia). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the engineered immune cells administered.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell. Small molecules, such as drugs, can also be secreted by diffusion through the membrane to the outside of cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which includes or expresses a tumor antigen.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

Overview

CAR T cell therapy has gained momentum after several promising clinical trials for the treatment of B-cell neoplasms and the FDA approval of a CD19 targeted CAR T cell for treatment of B cell acute lymphoid leukemia (Sadelain et al., *Nature* 545:423-431 (2017); Yu et al., *J Hematol Oncol.* 10:78 (2017); Kakarla and Gottschalk, *Cancer J.* 20:151-155 (2014); Wang et al., *J Hematol Oncol.* 10:53 (2017)). CAR T cell therapy involves isolating a patient's own T cells, engineering them to express a CAR, and reinfusing the engineered T cells back into the patient. The CAR consists of an extracellular single-chain variable fragment (scFv), transmembrane domain, and an intracellular signaling domain. Surface expression of a tumor-targeted scFv on the T cell results in tumor antigen-directed T cell activation and specific tumor killing via its signaling domain. However, many patients with hematologic cancers treated with CAR T cell therapy relapse with antigen loss variants as a result of tumor editing (Wang et al., *J Hematol Oncol.* 10:53 (2017)). Furthermore, translation of CAR T cell therapy to solid tumors has been difficult due to the immunosuppressive tumor environment (TME) (Yu et al., *J*

*Hematol Oncol.* 10:78 (2017); Kakarla and Gottschalk, *Cancer J.* 20:151-155 (2014)).

The TME consists of physical barriers, such as surrounding fibroblasts and extracellular matrix proteins, which make tumors less accessible to the T cells. Beyond this dense stromal network, T cell can encounter a number of inhibitory immune cells such as regulatory T cells, myeloid suppressor cells and tumor associated macrophages, as well an upregulation of immune checkpoint molecules, rendering the cytotoxic T cells inactive (Newick et al., *Annu Rev Med.* 1-14 (2016)). These immune checkpoints normally play a role in self recognition to prevent autoimmune responses, but are upregulated by many cancers to suppress immune cells (Topalian et al., Cancer Cell 27:451-461 (2015) and Postow et al., *J Clin Oncol.* 33:1974-1982 (2015)).

One approach to overcome the TME is to combine CAR T cell therapy with immune checkpoint blockade, which has proven to be a powerful treatment against a variety of cancers, including lung cancer, melanoma and gastric cancer (Topalian et al., *Cancer Cell* 27:451-461 (2015)). Currently, there are six approved checkpoint blockade therapies, all of which leverage two signaling pathways, the cytotoxic T lymphocyte-associated antigen 4 (CTLA-4) and programmed cell death protein 1 (PD-1) pathways. When the CTLA-4 and PD-1 receptors are expressed on the T cell surface, they function through distinct mechanisms to down-regulate T cell activity to prevent autoimmunity and maintain immunological homeostasis (Postow et al., *J Clin Oncol.* 33:1974-1982 (2015)). Although these therapies have been successful in treating patients with various cancers, patient response rate is variable (Matlung et al., *Immunol Rev.* 276:145-164 (2017); Rizvi et al., *Science* 348:124-128 (2015); Chao et al., *Cell* 24:225-232 (2011)).

Another immune checkpoint pathway is the Cluster of Differentiation 47 (CD47)-Signal Regulatory Protein α (SIRPα) pathway. SIRPα is a transmembrane glycoprotein found predominately on myeloid cells, including macrophages, monocytes and dendritic cells. The extracellular domain consists of three IgG superfamily domains, including an N-terminal CD47-binding domain, and is associated with two immunoreceptor tyrosine-based inhibitory motifs (ITIMs), which serve as docking sites for tyrosine phosphatases (Matlung et al., *Immunol Rev.* 276:145-164 (2017); Chao et al., *Cell* 24:225-232 (2011); Brown and Frazier, *Trends Cell Biol.* 11:130-135 (2001)). CD47 is expressed ubiquitously at low levels as a self-recognition signal (Matlung et al., *Immunol Rev.* 276:145-164 (2017)). CD47 binding to SIRPα on macrophages causes ITIM activation, resulting in induction of the docked tyrosine phosphatase, Src homology region 2 domain containing phosphatase-1 (SHP-1). SHP-1 then initiates a dephosphorylation cascade, causing dephosphorylation of myosin at the phagocytic synapse, preventing phagocytosis.

Many cancers exploit this mechanism and upregulate CD47 to send this "do not eat me" signal to macrophages (Matlung et al., *Immunol Rev.* 276:145-164 (2017); Chao et al., *Cell* 24:225-232 (2011)). Antagonizing this pathway with monoclonal antibodies (mAbs) and small molecules has been shown to activate phagocytosis in vitro and leads to tumor elimination in mice with a variety of cancers (Matlung et al., *Immunol Rev.* 276:145-164 (2017)). CV1, a peptide antagonist of the CD47-SIRPα pathway, potently synergizes with a multitude of mAbs, leading to decreased tumor burden and, in some cases, remissions in mice (Weiskopf et al., *Science* 341:1-13 (2014); Mathias et al., *Leukemia* 31(10):2254-2257 (2017)). CV1 is a truncated SIRPα variant with point mutations that increase its affinity for CD47, such that it outcompetes endogenous SIRPα (Weiskopf et al., *Science* 341:1-13 (2014)). It has little activity alone, but greatly enhances ADCP and potentially some other SIRPα mediated mechanisms, like antigen presentation by dendritic cells (Chao et al., *Cell* 24:225-232 (2011); Weiskopf et al., *Science* 341:1-13 (2014); Mathias et al., *Leukemia* 31(10):2254-2257 (2017); Xu et al., *Immunity* 47:363-373.e5 (2017); Liu et al., *Nat Med.* 21:1209-1215 (2015)). Although CV1 has yet to enter human trials, other anti-CD47 agents in trials have shown toxicities including anemia, due to the ubiquitous expression of CD47 (Matlung et al., *Immunol Rev.* 276:145-164 (2017); Weiskopf et al., *Science* 341:1-13 (2014); Liu et al. *PLoS One* 10:1-23 (2015)). Thus there is a need for new methods to increase the efficacy of CAR T cell therapy in solid tumors and to prevent antigen loss relapse in hematologic tumors and to reduce potential toxicities relating to CD47 blockade. Provided herein are engineered immune cells, including compositions comprising engineered immune cells and methods of use thereof, that address these issues.

As described herein, immune cells can be engineered to constitutively or conditionally express a soluble or membrane-bound SIRPα polypeptide that binds to CD47 in the tumor microenvironment. In some embodiments, the SIRPα polypeptides of the invention have an increased affinity for CD47 compared to endogenous SIRPα, such that they outcompete endogenous SIRPα for binding to CD47. Local secretion of a soluble SIRPα polypeptide at the tumor mitigates toxicities associated with systemic CD47 blockade. Localization of the SIRPα polypeptide on the cell surface also mitigates toxicities associated with systemic CD47 blockade. In some embodiments, the engineered immune cells additionally express a chimeric antigen receptor for delivering the immune cell to the target site. These engineered immune cells are interchangeably called herein orexigenic CAR T cells or OrexiCARs. OrexiCARs locally secrete a soluble SIRPα polypeptide or locally express a membrane-bound SIRPα polypeptide. Without wishing to be bound by theory, this combination reduces antigen-negative relapse, better eradicates an immunosuppressive solid tumor, and in some embodiments, enhances mAb-mediated killing, leading to a more complete tumor response.

The local secretion or local membrane-bound expression of a SIRPα polypeptide overcomes tumor resistance by providing a larger killing radius of unengaged and antigen-negative cancer cells and activating macrophage phagocytosis alone and stimulating their ability to kill tumor cells via ADCP, the major mechanism of antibody-mediated killing in vivo (FIG. 1). Accordingly, in some embodiments, the SIRPα polypeptide synergistically improves the potency of an anti-tumor monoclonal antibody. Engagement of the T cell receptor on the CAR leads to activation and expansion of the OrexiCARs, resulting in increased secretion of the SIRPα polypeptide and direct killing of tumor mass through intrinsic cytotoxic action of the CAR T cells and possible epitope spreading. The present technology allows the engineering of CAR T cells to better target solid tumors, in addition to other cancers. CAR T cells rely on their intrinsic T cell effector functions to kill, which may be defeated by the TME, antigen loss, or lack of target engagement. OrexiCARs secrete a polypeptide that operates through orthogonal mechanisms to effectively kill the cancer cells. Further, use of a secretable or membrane-bound polypeptide allows bystander killing of a target cancer cell that is either not engaged by the CAR T cell or is an antigen loss variant for the CAR T cell. In addition, use of continuous in situ secretion or membrane-bound expression can overcome the short half-life of a SIRPα polypeptide.

The methods provided herein allow for modular use of a wide range of CAR and tumor-reactive antibody combinations depending on the desired application. The tumor-reactive antibodies can synergize with the enhanced macrophage-mediated ADCP of cancer cells and/or with direct immune-based cytotoxic effects of the engineered immune cells, e.g., orexigenic CAR T cells. In some embodiments, the CAR and the tumor specific antibody target distinct tumor antigens. Without wishing to be bound by theory, this will decrease the risk of antigen-negative relapse by increasing the likelihood of killing multiple tumor populations to yield a more complete antitumor response. Accordingly, in one aspect, the disclosure provides methods to prevent escape of CAR target antigen-negative cells by use of an orthogonal antibody to a different antigen. The engineered immune cells described herein can be employed in combination with a wide variety of anti-tumor monoclonal antibodies. Tumor-reactive antibodies are known in art. Exemplary tumor-reactive antibodies include, but are not limited to, antibodies targeted to Her2, EGFR, PSMA, CD20, CD33, CD38, or WT1. In some embodiments, the tumor specific antibody is trastuzumab, cetuximab, ESK1, rituximab, daratumumab, or lintuzumab.

In some embodiments, the engineered immune cells provided herein express a T-cell receptor (TCR) or other cell-surface ligand that binds to a target antigen, such as a tumor antigen and a SIRPα polypeptide. In some embodiments, the T cell receptor is a wild-type, or native, T-cell receptor. In some embodiments, the T cell receptor is a chimeric T-cell receptor (CAR).

In exemplary embodiments provided herein, the engineered immune cells provided herein express a T-cell receptor (TCR) (e.g., a CAR) or other cell-surface ligand that binds to a CD19 tumor antigen. In some embodiments, the engineered immune cells provided herein express a T-cell receptor (TCR) (e.g., a CAR) or other cell-surface ligand that binds to a CD19 tumor antigen presented in the context of an MHC molecule. In some embodiments, the CD19 tumor antigen is presented in the context of an HLA-A2 molecule. CD19 is a B cell lineage specific antigen that has been the target of many of the most effective CAR T cells in human trials. CD19 is a model antigen due to its well-characterized activity, pharmacology and toxicity.

In exemplary embodiments provided herein, the engineered immune cells provided herein express an engineered T-cell receptor (TCR) (e.g., a CAR of a TCR mimic) or other cell-surface ligand that binds to a "preferentially expressed antigen in melanoma" (PRAME) tumor antigen. In some embodiments, the engineered immune cells provided herein express a T-cell receptor (TCR) (e.g., a CAR) or other cell-surface ligand that binds to a PRAME tumor antigen presented in the context of an MHC molecule. In some embodiments, the PRAME tumor antigen is presented in the context of an HLA-A2 molecule. The PRAME protein is a currently undruggable, retinoic acid receptor binding protein involved in differentiation, proliferation arrest, and apoptosis. PRAME is a cancer-testis antigen that has limited expression in healthy adult tissue restricted to the testes, ovaries, and endometrium. However, PRAME is over-expressed in multiple cancers including breast cancer, colon cancer, acute leukemias (50%), melanomas (90%), lymphomas, sarcomas among others, making it a highly attractive therapeutic target. After proteasomal processing the PRAME$^{300-309}$ peptide (ALYVDSLFFL) (SEQ ID NO: 32) is presented on the cell surface in the context of an HLA-I haplotype HLA*A02:01 (HLA-A2).

In exemplary embodiments provided herein, the engineered immune cells provided herein express a T-cell receptor (TCR) (e.g., a CAR) or other cell-surface ligand that binds to a Wilm's tumor protein 1 (WT1) tumor antigen. In some embodiments, the engineered immune cells provided herein express a T-cell receptor (TCR) (e.g., a CAR) or other cell-surface ligand that binds to a WT1 tumor antigen presented in the context of an MHC molecule. In some embodiments, the WT1 tumor antigen is presented in the context of an HLA-A2 molecule. WT1 is an important, validated, and NCI-top ranked, cancer target antigen. WT1 is a zinc finger transcription factor essential to the embryonal development of the urogenital system. WT1 is highly expressed in most leukemias including AML, CML, ALL and MDS as well as in myeloma and several solid tumors, particularly ovarian carcinoma and mesothelioma. WT1 vaccines have advanced into clinical trials for patients with a variety of cancers. WT1 is distinguished by its importance to the survival of clonogenic leukemic cells, and the ability to treat tumors with T-cells specific for WT1 peptides in xenografted NOD/SCID mice, without adversely affecting normal hematopoiesis. WT1 peptide vaccination has been associated with complete or partial remissions of disease and prolonged survival.

In exemplary embodiments provided herein, the engineered immune cells provided herein express a T-cell receptor (TCR) (e.g., a CAR) or other cell-surface ligand that binds to a mesothelin tumor antigen. In some embodiments, the engineered immune cells provided herein express a T-cell receptor (TCR) (e.g., a CAR) or other cell-surface ligand that binds to a mesothelin tumor antigen presented in the context of an MHC molecule. In some embodiments, the mesothelin tumor antigen is presented in the context of an HLA-A2 molecule. Mesothelin is a cell-surface glycoprotein that is highly expressed in many cancers, such as malignant mesothelioma, pancreatic cancer, ovarian cancer, lung cancer, endometrial cancer, biliary cancer, gastric cancer, and pediatric acute myeloid leukemia (Hassan et al., *J Clin Oncol.* 34(34):4171-4179 (2016). Preclinical studies and results from initial clinical trials have validated mesothelin as an attractive target for cancer therapy with antibody-based approaches as well as tumor vaccines (Pastan et al., *Cancer Res.* 74:2907-2912 (2014)).

In exemplary embodiments provided herein, the engineered immune cells provided herein express a T-cell receptor (TCR) (e.g., a CAR) or other cell-surface ligand that binds to a MUC16 tumor antigen. In some embodiments, the engineered immune cells provided herein express a T-cell receptor (TCR) (e.g., a CAR) or other cell-surface ligand that binds to a MUC16 tumor antigen presented in the context of an MHC molecule. In some embodiments, the MUC16 tumor antigen is presented in the context of an HLA-A2 molecule. MUC16 is a high molecular weight, heavily glycosylated mucin involved in various physiological processes related to both normal as well as malignant conditions. MUC16 is overexpressed in ovarian cancer and CA125, the extracellular domain of MUC16, is a well-established biomarker for ovarian cancer. MUC16 has also been associated with pancreatic cancer, breast cancer, colorectal cancer, lung cancer, bladder cancer, and oral squamous cell carcinoma (Suh et al., Chemo Open Access 6:235 (2017). In some embodiments, an engineered immune cell provided herein binds to the extracellular retained fraction of MUC16 (MUC16$^{ecto}$) (Chemasova et al., *Clin Cancer Res.* 16(14):3594-3606 (2010).

In exemplary embodiments provided herein, the engineered immune cells provided herein express a T-cell receptor (TCR) (e.g., a CAR) or other cell-surface ligand that binds to a prostate stem cell antigen (PSCA) tumor antigen. In some embodiments, the engineered immune cells provided herein express a T-cell receptor (TCR) (e.g., a CAR) or other cell-surface ligand that binds to a PSCA tumor antigen presented in the context of an MHC molecule. In some embodiments, the PSCA tumor antigen is presented in the context of an HLA-A2 molecule. PSCA is up-regulated in cancers such as prostate cancer, bladder cancer, breast cancer and pancreatic cancer (Link et al., *Oncotarget* 8(33): 54592-54603 (2017)).

In exemplary embodiments provided herein, the engineered immune cells provided herein express a T-cell receptor (TCR) (e.g., a CAR) or other cell-surface ligand that binds to a B cell maturation antigen (BCMA) tumor antigen. In some embodiments, the engineered immune cells provided herein express a T-cell receptor (TCR) (e.g., a CAR) or other cell-surface ligand that binds to a BCMA tumor antigen presented in the context of an MHC molecule. In some embodiments, the BCMA tumor antigen is presented in the context of an HLA-A2 molecule. BCMA is a type III transmembrane protein containing cysteine-rich extracellular domains and is widely expressed on malignant plasma cells at elevated levels in multiple myeloma. BCMA is an appealing target for mAb-based and CAR-based immunotherapies (Tai and Anderson, *Immunotherapy* 7(11):1187-1199 (2015)).

The engineered immune cells (e.g., CAR T cells) provided herein that express an antigen receptor, e.g., a chimeric antigen receptor, in combination with a SIRPα polypeptide provide numerous advantages over the existing CAR T cell technology and CD47-blocking therapies. A non-exhaustive list of these advantages includes, for example: 1) Combining CAR T cells with CD47-SIRPα blockade engages both innate and adaptive immune pathways, and is thus more potent than other combinations. 2) The ability of the engineered immune cells (e.g., CAR T cells) to locally synthesize and secrete soluble or express membrane-bound SIRPα polypeptide at the tumor site, thus avoiding toxicity associated with systemic CD47-blocking therapies. 3) The ability of the engineered cells (e.g., CAR T cells) to increase the quantity of SIRPα polypeptide locally at the tumor site. This is because the engineered immune cells contain nucleic acid(s) encoding the SIRPα polypeptide for expression of numerous copies of SIRPα polypeptide by the cell. In addition, the engineered immune cells will proliferate extensively (e.g., 100 times or more) when it encounters the tumor specific antigen at the tumor site, thus significantly increasing production of the SIRPα polypeptide. 4) The engineered immune cells (e.g., CAR T cells) can be easily generated by in vitro transduction of immune cells with nucleic acid encoding the chimeric antigen and the SIRPα polypeptide. 5) The engineered immune cells (e.g., CAR T cells) can also have additive or synergistic anti-tumor activity of its own. Further, the activity of the engineered immune cells (e.g., CAR T cells) can be adjusted by selection of co-stimulatory molecules include in the chimeric antigen receptor. 6) Gated conditional expression of the SIRPα polypeptide can be employed to allow better control of toxicity. 7) If the SIRPα polypeptide-mediated cancer killing only is needed and/or CAR T mediated killing is not desired, the engineered immune cells (e.g., CAR T cells) can be further modified to engineer out the T cell-mediated inflammatory responses (e.g., cytokine release), which are responsible for much of the toxicity seen in humans. 8) Use of continuous in situ secretion or membrane-bound expression can overcome the short half-life of a SIRPα polypeptide.

SIRPα Polypeptides

The engineered immune cells (e.g., CAR T cells) provided herein express at least one SIRPα polypeptide that binds to CD47. SIRPα is a transmembrane glycoprotein found predominately on myeloid cells, including macrophages, monocytes and dendritic cells. The extracellular domain consists of three IgG superfamily domains, including an N-terminal CD47-binding domain, and is associated with two immunoreceptor tyrosine-based inhibitory motifs (ITIMs), which serve as docking sites for tyrosine phosphatases (Matlung et al., *Immunol Rev.* 276:145-164 (2017); Chao et al., *Cell* 24:225-232 (2011); Brown and Frazier, *Trends Cell Biol.* 11:130-135 (2001)). The wild-type SIRPα protein sequence has a NCBI Reference No: NP_542970.1 (SEQ ID NO: 33). The amino acid sequence of SEQ ID NO: 33 is shown below:

```
                                        (SEQ ID NO: 33)
MEPAGPAPGRLGPLLCLLLAASCAWSGVAGEEELQVIQPDKSVLVAAGET
ATLRCTATSLIPVGPIQWFRGAGPGRELIYNQKEGHFPRVTTVSDLTKRN
NMDFSIRIGNITPADAGTYYCVKFRKGSPDDVEFKSGAGTELSVRAKPSA
PVVSGPAARATPQHTVSFTCESHGFSPRDITLKWFKNGNELSDFQTNVDP
VGESVSYSIHSTAKVVLTREDVHSQVICEVAHVTLQGDPLRGTANLSETI
RVPPTLEVTQQPVRAENQVNVTCQVRKFYPQRLQLTWLENGNVSRTETAS
TVTENKDGTYNWMSWLLVNVSAHRDDVKLTCQVEHDGQPAVSKSHDLKVS
AHPKEQGSNTAAENTGSNERNIYIVVGVVCTLLVALLMAALYLVRIRQKK
AQGSTSSTRLHEPEKNAREITQDTNDITYADLNLPKGKKPAPQAAEPNNH
TEYASIQTSPQPASEDTLTYADLDMVHLNRTPKQPAPKPEPSFSEYASVQ
VPRK.
```

In some embodiments, the SIRPα polypeptides of the invention have an increased affinity for CD47 compared to endogenous SIRPα, such that they outcompete endogenous SIRPα for binding to CD47. In some embodiments, the SIRPα polypeptides of the invention are soluble and/or truncated. In some embodiments, the SIRPα polypeptides of the invention are membrane-bound. In some embodiments, the SIRPα polypeptides of the invention comprise one or more amino acid modifications relative to the wild-type SIRPα protein. In some embodiments, a SIRPα polypeptide of the invention has an increased affinity of at least 10-fold, at least 20-fold, at least 50-fold, at least 100-fold, at least 500-fold, at least 1000-fold, or more compared to wild-type SIRPα. In some embodiments, the SIRPα polypeptides lack the SIRPα transmembrane domain and/or are soluble. In some embodiments, the SIRPα polypeptides are membrane-bound. In some embodiments, the SIRPα polypeptides comprise at least one mutation relative to the wild-type SIRPα protein.

In some embodiments, the SIRPα polypeptide expressed by the engineered immune cell is the wild-type SIRPα polypeptide. In some embodiments, the SIRPα polypeptide expressed by the engineered immune cell has an amino acid sequence that is at least about 85%, about 90%, about 95%, about 96%, about 97%, about 98%, about 99% homologous to SEQ ID NO: 33, or is a fragment thereof, or a naturally occurring allelic variant thereof, and/or may optionally comprise up to one or up to two or up to three conservative amino acid substitutions. In some embodiments, the soluble SIRPα polypeptides comprise at least one mutation relative to the wild-type SIRPα protein or corresponding fragment thereof. The mutations include, e.g., substitutions, deletions, insertions, etc. of one or more amino acids. Amino acid substitutions or insertions include substitutions or insertions with either a naturally occurring amino acid or a non-naturally occurring amino acid. Amino acid changes may be made in at least 1, 2, 3, 4, 5, 6, 7, 8, 9, 10, or more amino acid residues relative to a wild-type SIRPα polypeptide.

The native signal peptide of SIRPα spans residues 1-30 of SEQ ID NO: 33 and the extracellular domain of wild-type SIRPα spans residues 31-373 of SEQ ID NO: 33 and residues 1-30. The dl domain of wild-type SIRPα corresponds to residues 31-149 of SEQ ID NO: 33 and is set forth in SEQ ID NO: 34. In certain embodiments, the SIRPα polypeptide can have an amino acid sequence that is a consecutive portion of SEQ ID NO: 33 which is at least 20, or at least 30, or at least 40, or at least 50, at least 100, at least 110, at least 120, at least 150, at least 200, and up to the full-length of the extracellular domain of wild-type SIRPα. The amino acid sequence of SEQ ID NO: 34 is shown below:

```
                                  (SEQ ID NO: 34)
EEELQVIQPDKSVSVAAGESAILHCTVTSLIPVGPIQWFRGAGPARELIY

NQKEGHFPRVTTVSESTKRENIVIDFSISISNITPADAGTYYCVKFRKGS

PDTEFKSGAGTELSVRAKPS
```

In certain embodiments, a soluble SIRPα polypeptide comprises all of the dl domain, which corresponds to residues 31 to 149 of SEQ ID NO: 33, set forth in SEQ ID NO: 34. In some embodiments, a soluble SIRPα polypeptide comprises a portion of the dl domain. Accordingly, a soluble SIRPα polypeptide can have an amino acid sequence that is at least about 85%, about 90%, about 95%, about 96%, about 97%, about 98%, about 99% or about 100% identical to SEQ ID NO: 34 or a fragment thereof. Alternatively, a soluble SIRPα polypeptide can have an amino acid sequence that is a consecutive portion of SEQ ID NO: 34 which is at least 20, or at least 30, or at least 40, or at least 50, at least 60, at least 70, at least 80, at least 90, at least 100, at least 110, amino acids of SEQ ID NO: 34.

Amino acid substitutions in the N-terminal dl domain of SIRPα (residues 31-149 of the wild-type SIRPα protein) increase affinity for CD47. Accordingly, in some embodiments, the SIRPα polypeptides of the invention comprise the dl domain of SIRPα and optionally, comprise at least one amino acid change relative to the wild-type sequence within the dl domain. In some embodiments, a soluble SIRPα polypeptide has 1, 2, 3, 4, 5, 6, 7, 8, 9, 10, or more amino acid substitutions compared to the wild-type polypeptide. In some embodiments, the SIRPα polypeptide is secreted by the engineered immune cell. In some embodiments, the SIRPα polypeptide is membrane-bound in the plasma membrane of the engineered immune cell. The SIRPα polypeptide can be any SIRPα polypeptide which is capable of binding CD47 with a higher affinity than the native SIRPα protein and which is not normally expressed in a cell (e.g., a mammalian cell, such as a human cell) or released into the circulation.

In some embodiments, amino acid changes are made in the dl domain at one or more of the amino acids within the set of hydrophobic core residues of SIRPα, which include, L4, V6, V27, I36, F39, L48, 149, Y50, F57, V60, M72, F74, I76, V92, F94 and F103 (the numbering is according to dl domain shown in SEQ ID NO: 34). In some embodiments, amino acid changes are made at one or more residues that contact CD47, which include, A29, L30, 131, P32, V33, G34, P35, Q52, K53, E54, S66, T67, K68, R69, F74, K93, K96, G97, S98, and D100 (the numbering is according to dl domain shown in SEQ ID NO: 34). In some embodiments, a soluble SIRPα polypeptide comprises mutations at one or more (or two or more of, three or more of, four or more of, etc.) of L4, V6, A21, V27, I31, E47, K53, E54, H56, S66, V63, K68, V92, F94, F103 or a combination thereof. Exemplary SIRPα polypeptides and methods of generating such are described in, e.g., U.S. Pat. No. 9,944,911, which is incorporated by reference in its entirety herein.

In some embodiments, the SIRPα polypeptides of the invention have a dissociation constant ($K_D$) of at least about $1\times10^{-8}$, at least about $1\times10^{-9}$, at least about $1\times10^{-10}$, at least about $1\times10^{-11}$, or at least about $1\times10^{-12}$, for CD47.

In some embodiments, a SIRPα polypeptide of the invention is a fusion protein having at least a portion of a SIRPα polypeptide fused in frame to a heterologous domain. Such heterologous domains may include, but are not limited to, polyhistidine, Glu-Glu, glutathione S transferase (GST), thioredoxin, protein A, protein G, an immunoglobulin heavy chain constant region (e.g., an Fc), maltose binding protein (MBP), various fluorescent proteins (e.g., GFP), epitope tags (e.g., FLAG, influenza virus hemagglutinin (HA), and c-myc tags), or human serum albumin domains. A fusion domain may be selected so as to confer a desired property (e.g. a fusion domain may be useful for isolating the fusion protein, a fusion domain may facilitate detection of the fusion protein, a fusion domain may be useful for dimerizing or multimerizing, or a fusion domain may be useful for increasing the serum half-life of the fusion protein, etc.). In some embodiments, the SIRPα polypeptide is fused to an immunoglobulin Fc domain or a portion thereof. As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In some embodiments, the immunoglobulin Fc region may comprise at least an immunoglobulin hinge region a CH2 domain and a CH3 domain, and lack the CH1 domain. In some embodiments, a SIRPα polypeptide may comprise only a domain of an immunoglobulin, such as a CH1 domain, a CH2 domain or a CH3 domain. Fusions with the Fc portion of an immunoglobulin are known to confer desirable pharmacokinetic properties on a wide range of proteins. Likewise, fusions to human serum albumin can confer desirable properties.

Altered polypeptides can be made by standard recombinant DNA techniques, e.g., by cloning the polypeptide, determining its gene sequence and altering the gene sequence by methods such as site-directed mutagenesis. For expression of the secreted SIRPα polypeptide, eukaryotic based expression systems (e.g., plasmid or viral-based systems, such as retroviral transduction) are employed. For secretion, a signal peptide is included at the N-terminus of the polypeptide. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the N-terminus of the SIRPα polypeptide and is the native SIRPα signal peptide (residues 1-30 of SEQ ID NO: 33). In certain embodiments, the soluble SIRPα polypeptide is consensus variant 1 (CV1) described in Weiskopf et al., *Science* 341:1-13 (2014). The amino acid sequence of CV1 is set forth in SEQ ID NO: 35 below:

(SEQ ID NO: 35)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPS.

In certain embodiments, the signal peptide comprises the native SIRPα signal polypeptide comprising amino acids having the sequence set forth in SEQ ID NO: 36 as provided below:

(SEQ ID NO: 36)
MGSTMEPAGPAPGRLGPLLCLLLAASCAWSGVAG.

An exemplary construct for expression of a soluble SIRPα polypeptide in an engineered immune cell comprises: a P2A self-cleaving peptide, the native SIRPα signal peptide, CV1, and a HA tag and comprises the amino acid sequence set forth in SEQ ID NO: 37 as provided below:

(SEQ ID NO: 37)
GSGATNFSLLKQAGDVEENPGPMGSTMEPAGPAPGRLGPLLCLLLAASCA

WSGVAGEEELQIIQPDKSVLVAAGETATLRCTITSLFPVGPIQWFRGAGP

GRVLIYNQRQGPFPRVTTVSDTTKRNNMDFSIRIGNITPADAGTYYCIKF

RKGSPDDVEFKSGAGTELSVRAKPSYPYDVPDYA.

The signal peptide is underlined and the secreted polypeptide, CV1, is in bold.

The nucleotide sequence encoding the amino acid sequence of SEQ ID NO: 37 is set forth in SEQ ID NO: 38 as provided below:

(SEQ ID NO: 38)
GGAAGCGGAGCTACTAACTTCAGCCTGCTGAAGCAGGCTGGAGACGTGGA

GGAGAACCCTGGACCTATGGGATCCACCATGGAACCTGCTGGTCCCGCTC

CGGGCCGCCTGGGACCACTCCTTTGCCTTCTCTTGGCTGCATCTTGTGCC

TGGAGTGGAGTCGCAGGAGAGGAAGAGCTCCAGATCATACAGCCCGATAA

GTCCGTTCTTGTAGCGGCTGGCGAGACTGCCACTCTCAGATGCACTATCA

CAAGCCTTTTTCCCGTGGGGCCTATTCAGTGGTTTCGCGGGGCAGGCCCG

GGCAGGGTACTTATCTACAATCAGCGACAGGGCCCATTCCCCCGAGTAAC

CACAGTGAGCGATACCACCAAACGGAACAATATGGACTTTAGTATTCGGA

TCGGTAACATAACCCCCGCAGACGCAGGCACGTACTATTGTATCAAATTC

CGCAAGGGAAGCCCCGACGATGTGGAGTTTAAATCTGGTGCTGGCACTGA

ACTGTCCGTTCGAGCGAAGCCATCATACCCCTACGACGTTCCTGATTACG

CCTAGTAGGAATTCAC.

Targeting Ligands and Target Antigens

In some embodiments, the engineered immune cells provided herein express a T-cell receptor (TCR) or other cell-surface ligand that binds to a target antigen, such as a tumor antigen. The cell-surface ligand can be any molecule that directs an immune cell to a target site (e.g., a tumor site). Exemplary cell surface ligands include, for example, endogenous receptors, engineered receptors, or other specific ligands, to achieve targeting of the immune cell to a target site. In some embodiments, the receptor is a T cell receptor. In some embodiments, the T cell receptor is a wild-type, or native, T-cell receptor that binds to a target antigen. In some embodiments, the receptor, e.g. a T cell receptor, is non-native receptor (e.g., not endogenous to the immune cells). In some embodiments, the non-native receptor is a truncated receptor, a genetically modified receptor, a TCR mimic receptor, an antibody, or other ligand capable of interacting with a target cell. In some embodiments, the receptor is a chimeric antigen receptor (CAR), for example, a T cell CAR that binds to a target antigen, or an antibody that mimics TCR function (a TCR mimic).

In some embodiments, the target antigen is expressed on normal healthy cells. In some embodiments, the target antigen is an extracellular antigen. In some embodiments, the target antigen is expressed by a tumor cell. In some embodiments, the target antigen is expressed on the surface of a tumor cell. In some embodiments, the target antigen is a cell surface receptor. In some embodiments, the target antigen is a cell surface glycoprotein. In some embodiments, the target antigen is secreted by a tumor cell. In some embodiments, the target antigen is localized to the tumor microenvironment. In some embodiments, the target antigen is localized to the extracellular matrix or stroma of the tumor microenvironment. In some embodiments, the target antigen is expressed by one or more cells located within the extracellular matrix or stroma of the tumor microenvironment.

In some embodiments, the target antigen is a tumor antigen selected from among 5T4, alpha 501-integrin, 707-AP, A33, AFP, ART-4, B7H4, BAGE, Bcl-2, β-catenin, BCMA, Bcr-abl, MN/C IX antibody, CA125, CA19-9, CAMEL, CAP-1, CASP-8, CD4, CD5, CD19, CD20, CD21, CD22, CD25, CDC27/m, CD33, CD37, CD45, CD52, CD56, CD80, CD123, CDK4/m, CEA, c-Met, CS-1, CT, Cyp-B, cyclin B1, DAGE, DAM, EBNA, EGFR, ErbB3, ELF2M, EMMPRIN, EpCam, ephrinB2, estrogen receptor, ETV6-AML1, FAP, ferritin, folate-binding protein, GAGE, G250, GD-2, GM2, GnT-V, gp75, gp100 (Pmel 17), HAGE, HER-2/neu, HLA-A*0201-R170I, HPV E6, HPV E7, Ki-67, HSP70-2M, HST-2, hTERT (or hTRT), iCE, IGF-1R, IL-2R, IL-5, KIAA0205, LAGE, LDLR/FUT, LRP, MAGE, MART, MART-1/melan-A, MART-2/Ski, MC1R, mesothelin, MUC, MUC16, MUM-1-B, myc, MUM-2, MUM-3, NA88-A, NYESO-1, NY-Eso-B, p53, proteinase-3, p190 minor ber-abl, Pml/RARα, PRAME, progesterone receptor, PSA, PSCA, PSM, PSMA, ras, RAGE, RU1 or RU2, RORI, SART-1 or SART-3, survivin, TEL/AML1, TGFβ, TPI/m, TRP-1, TRP-2, TRP-2/INT2, tenascin, TSTA tyrosinase, VEGF, and WT1. In certain embodiments, the target antigen is a tumor antigen selected from among BCMA, CD19, mesothelin, MUC16, PSCA, WT1, and PRAME.

Without limiting the foregoing, exemplary cancers that can be treated by targeting the associated provided antigens include: leukemia/lymphoma (CD19, CD20, CD22, ROR1, CD33); acute myeloid leukemia (WT1, PRAME); multiple myeloma (B-cell maturation antigen (BCMA)); prostate cancer (PSMA, WT1, Prostate Stem Cell antigen (PSCA), SV40 T); breast cancer (Her2, ERBB2); stem cell cancer (CD133); ovarian cancer (L1-CAM, mesothelin, extracellular domain of MUC16 (MUC-CD), folate binding protein (folate receptor), Lewis Y); renal cell carcinoma (carboxyanhydrase-IX (CAIX); melanoma (GD2); and pancreatic cancer (mesothelin, CEA, CD24); non-small cell lung cancer (mesothelin); esophageal cancer (mesothelin); gastric cancer (mesothelin); colorectal cancer (mesothelin); triple negative breast cancer (mesothelin, MUC16).

Typical therapeutic anti-cancer mAbs, like those that bind to CD19, recognize cell surface proteins, which constitute only a tiny fraction of the cellular protein content. Most mutated or oncogenic tumor associated proteins are typically nuclear or cytoplasmic. In certain instances, these intracellular proteins can be degraded in the proteasome, processed and presented on the cell surface by MHC class I molecules as T cell epitopes that are recognized by T cell receptors (TCRs). The development of mAbs that mimic TCR function, "TCR mimic (TCRm)" or "TCR-like"; (i.e., that recognize peptide antigens of key intracellular proteins in the context of MHC on the cell surface) greatly extends the potential repertoire of tumor targets addressable by potent mAbs. TCRm Fab, or scFv, and mouse IgG specific for the melanoma Ags, NY-ESO-1, hTERT, MART 1, gp100, and PR1, among others, have been developed. The antigen binding portions of such antibodies can be incorporated into the CARs provided herein. HLA-A2 is the most common HLA haplotype in the USA and EU (about 40% of the population). Therefore, potent TCRm mAb and native TCRs against tumor antigens presented in the context of HLA-A2 are useful in the treatment of a large population.

Accordingly, in some embodiments, the target antigen is a tumor antigen presented in the context of an MHC molecule. In some embodiments, the MHC protein is a MHC class I protein. In some embodiments, the MHC Class I protein is an HLA-A, HLA-B, or HLA-C molecule. In some embodiments, the target antigen is a tumor antigen presented in the context of an HLA-A2 molecule. mAbs for intracellular WT1 and PRAME antigens presented in the context of surface HLA-A2 molecules have previously been developed. IgG1, afucosylated Fc forms, bispecific, BiTE, and CAR T cell formats have been made that exhibit potent therapeutic activity in multiple preclinical animal models. Such antibodies or an antigen-binding portion thereof can be employed as described herein for the recognition of target antigens present on the surface of a target cell (e.g., a tumor cell) in the context of an MHC molecule.

Chimeric Antigen Receptors

In some embodiments, the engineered immune cells provided herein express at least one chimeric antigen receptor (CAR). CARs are engineered receptors, which graft or confer a specificity of interest onto an immune effector cell. For example, CARs can be used to graft the specificity of a monoclonal antibody onto an immune cell, such as a T cell. In some embodiments, transfer of the coding sequence of the CAR is facilitated by a nucleic acid vector, such as a retroviral vector.

There are currently three generations of CARs. In some embodiments, the engineered immune cells provided herein express a "first generation" CAR. "First generation" CARs are typically composed of an extracellular antigen binding domain (e.g., a single-chain variable fragment (scFv)) fused to a transmembrane domain fused to cytoplasmic/intracellular domain of the T cell receptor (TCR) chain. "First generation" CARs typically have the intracellular domain from the CD3ζ chain, which is the primary transmitter of signals from endogenous TCRs. "First generation" CARs can provide de novo antigen recognition and cause activation of both $CD4^+$ and $CD8^+$ T cells through their CD3ζ chain signaling domain in a single fusion molecule, independent of HLA-mediated antigen presentation.

In some embodiments, the engineered immune cells provided herein express a "second generation" CAR. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (e.g., CD3ζ). Preclinical studies have indicated that "Second Generation" CARs can improve the antitumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL).

In some embodiments, the engineered immune cells provided herein express a "third generation" CAR. "Third generation" CARs comprise those that provide multiple co-stimulation (e.g., CD28 and 4-1BB) and activation (e.g., CD3ζ).

In accordance with the presently disclosed subject matter, the CARs of the engineered immune cells provided herein comprise an extracellular antigen-binding domain, a transmembrane domain and an intracellular domain.

Extracellular Antigen-Binding Domain of a CAR

In some embodiments, the target antigen is expressed on normal healthy cells. In some embodiments, the target antigen is an extracellular antigen. In certain embodiments, the extracellular antigen-binding domain of a CAR specifically binds a tumor antigen. In certain embodiments, the extracellular antigen-binding domain is derived from a monoclonal antibody (mAb) that binds to a tumor antigen. In some embodiments, the extracellular antigen-binding domain comprises an scFv. In some embodiments, the extracellular antigen-binding domain comprises a Fab, which is optionally crosslinked. In some embodiments, the extracellular binding domain comprises a $F(ab)_2$. In some embodiments, any of the foregoing molecules are comprised in a fusion protein with a heterologous sequence to form the extracellular antigen-binding domain. In certain embodiments, the extracellular antigen-binding domain comprises a human scFv that binds specifically to a tumor antigen. In certain embodiments, the scFv is identified by screening scFv phage library with tumor antigen-Fc fusion protein.

In certain embodiments, the extracellular antigen-binding domain of a presently disclosed CAR has a high binding specificity and high binding affinity to a tumor antigen (e.g., a mammalian tumor antigen, such as a human tumor antigen). For example, in some embodiments, the extracellular antigen-binding domain of the CAR (embodied, for example, in a human scFv or an analog thereof) binds to a particular tumor antigen with a dissociation constant ($K_d$) of about $1\times10^{-5}$ M or less. In certain embodiments, the $K_d$ is about $5\times10^{-6}$ M or less, about $1\times10^{-6}$ M or less, about $5\times10^{-7}$ M or less, about $1\times10^{-7}$ M or less, about $5\times10^{-8}$ M or less, about $1\times10^{-8}$ M or less, about $5\times10^{-9}$ or less, about $4\times10^{-9}$ or less, about $3\times10^{-9}$ or less, about $2\times10^{-9}$ or less, or about $1\times10^{-9}$ M or less. In certain non-limiting embodiments, the $K_d$ is from about $3\times10^{-9}$ M or less. In certain non-limiting embodiments, the $K_d$ is from about $3\times10^{-9}$ to about $2\times10^{-7}$.

Binding of the extracellular antigen-binding domain (embodiment, for example, in a human scFv or an analog thereof) of a presently disclosed tumor antigen-targeted CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the tumor antigen-targeted CAR is labeled with a fluorescent marker. Non-limiting examples of fluorescent markers include green fluorescent protein (GFP), blue fluorescent protein (e.g., EBFP, EBFP2, Azurite, and mKalamal), cyan fluorescent protein (e.g., ECFP, Cerulean, and CyPet), and yellow fluorescent protein (e.g., YFP, Citrine, Venus, and YPet). In certain embodiments, the human scFv of a presently disclosed tumor antigen-targeted CAR is labeled with GFP.

In some embodiments, the extracellular antigen-binding domain of the expressed CAR binds to tumor antigen that is expressed by a tumor cell. In some embodiments, the extracellular antigen-binding domain of the expressed CAR binds to tumor antigen that is expressed on the surface of a tumor cell. In some embodiments, the extracellular antigen-binding domain of the expressed CAR binds to tumor antigen that is expressed on the surface of a tumor cell in combination with an MHC protein. In some embodiments, the MHC protein is a MHC class I protein. In some embodiments, the MHC Class I protein is an HLA-A, HLA-B, or HLA-C molecule. In some embodiments, the extracellular antigen-binding domain of the expressed CAR binds to tumor antigen that is expressed on the surface of a tumor cell not in combination with an MHC protein.

In some embodiments, the extracellular antigen-binding domain of the expressed CAR binds to tumor antigen selected from among 5T4, alpha 5β1-integrin, 707-AP, A33, AFP, ART-4, B7H4, BAGE, Bcl-2, β-catenin, BCMA, Bcr-abl, MN/C IX antibody, CA125, CA19-9, CAMEL, CAP-1, CASP-8, CD4, CD5, CD19, CD20, CD21, CD22, CD25, CDC27/m, CD33, CD37, CD45, CD52, CD56, CD80, CD123, CDK4/m, CEA, c-Met, CS-1, CT, Cyp-B, cyclin B1, DAGE, DAM, EBNA, EGFR, ErbB3, ELF2M, EMMPRIN, EpCam, ephrinB2, estrogen receptor, ETV6-AML1, FAP, ferritin, folate-binding protein, GAGE, G250, GD-2, GM2, GnT-V, gp75, gp100 (Pmel 17), HAGE, HER-2/neu, HLA-A*0201-R170I, HPV E6, HPV E7, Ki-67, HSP70-2M, HST-2, hTERT (or hTRT), iCE, IGF-1R, IL-2R, IL-5, KIAA0205, LAGE, LDLR/FUT, LRP, MAGE, MART, MART-1/melan-A, MART-2/Ski, MC1R, mesothelin, MUC, MUC16, MUM-1-B, myc, MUM-2, MUM-3, NA88-A, NYESO-1, NY-Eso-B, p53, proteinase-3, p190 minor bcr-abl, Pml/RARα, PRAME, progesterone receptor, PSA, PSCA, PSM, PSMA, ras, RAGE, RU1 or RU2, RORI, SART-1 or SART-3, survivin, TEL/AML1, TGFβ, TPI/m, TRP-1, TRP-2, TRP-2/INT2, tenascin, TSTA tyrosinase, VEGF, and WT1. In certain embodiments, the extracellular antigen-binding domain of the expressed CAR binds to tumor antigen selected from among BCMA, CD19, mesothelin, MUC16, PSCA, WT1, and PRAME. Exemplary extracellular antigen-binding domains and methods of generating such domains and associated CARs are described in, e.g., WO2016/191246, WO2017/023859, WO2015/188141, WO2015/070061, WO2012/135854, WO2014/055668, which are incorporated by reference in their entirety, including the sequence listings provided therein.

In some embodiments, the extracellular antigen-binding domain of the expressed CAR binds to a CD19 tumor antigen. In some embodiments, the extracellular antigen-binding domain of the expressed CAR binds to a CD19 tumor antigen presented in the context of an MHC molecule. In some embodiments, the extracellular antigen-binding domain of the expressed CAR binds to a CD19 tumor antigen presented in the context of an HLA-A2 molecule.

In some embodiments, the extracellular antigen-binding domain of the expressed CAR binds to a "preferentially expressed antigen in melanoma" (PRAME) tumor antigen. In some embodiments, the extracellular antigen-binding domain of the expressed CAR binds to a PRAME tumor antigen presented in the context of an MHC molecule. In some embodiments, the extracellular antigen-binding domain of the expressed CAR binds to a PRAME tumor antigen presented in the context of an HLA-A2 molecule.

In some embodiments, extracellular antigen-binding domain of the expressed CAR binds to a WT1 (Wilm's tumor protein 1) tumor antigen. In some embodiments, the extracellular antigen-binding domain of the expressed CAR binds to a WT1 tumor antigen presented in the context of an MHC molecule. In some embodiments, the extracellular antigen-binding domain binds to a WT1 tumor antigen presented in the context of an HLA-A2 molecule.

In some embodiments, extracellular antigen-binding domain of the expressed CAR binds to a MUC16 tumor antigen. In some embodiments, the extracellular antigen-binding domain of the expressed CAR binds to a MUC16 tumor antigen presented in the context of an MHC molecule. In some embodiments, the extracellular antigen-binding domain binds to a MUC16 tumor antigen presented in the context of an HLA-A2 molecule.

In some embodiments, extracellular antigen-binding domain of the expressed CAR binds to a mesothelin tumor antigen. In some embodiments, the extracellular antigen-binding domain of the expressed CAR binds to a mesothelin tumor antigen presented in the context of an MHC molecule. In some embodiments, the extracellular antigen-binding domain binds to a mesothelin tumor antigen presented in the context of an HLA-A2 molecule.

In some embodiments, extracellular antigen-binding domain of the expressed CAR binds to a BCMA (B-cell maturation antigen) tumor antigen. In some embodiments, the extracellular antigen-binding domain of the expressed CAR binds to a BCMA tumor antigen presented in the context of an MHC molecule. In some embodiments, the extracellular antigen-binding domain binds to a BCMA tumor antigen presented in the context of an HLA-A2 molecule.

In some embodiments, extracellular antigen-binding domain of the expressed CAR binds to a PSCA (prostate stem cell antigen) tumor antigen. In some embodiments, the extracellular antigen-binding domain of the expressed CAR binds to a BCMA tumor antigen presented in the context of an MHC molecule. In some embodiments, the extracellular antigen-binding domain binds to a BCMA tumor antigen presented in the context of an HLA-A2 molecule.

In certain embodiments, the extracellular antigen-binding domain (e.g., human scFv) comprises a heavy chain variable region and a light chain variable region, optionally linked with a linker sequence, for example a linker peptide (e.g., SEQ NO: 1), between the heavy chain variable region and the light chain variable region. In certain embodiments, the extracellular antigen-binding domain is a human scFv-Fc fusion protein or full length human IgG with $V_H$ and $V_L$ regions.

In certain embodiments, the extracellular antigen-binding domain comprises a human scFv that binds to a CD19 antigen. In some embodiments, the scFv comprises a polypeptide having an amino acid sequence of SEQ ID NO: 3.

(SEQ ID NO: 3)
EVKLQQSGAELVRPGSSVKISCKASGYAFSSYWMNWVKQRPGQGLEWIGQ

IYPGDGDTNYNGKFKGQATLTADKSSSTAYMQLSGLTSEDSAVYFCARKT

ISSVVDFYFDYWGQGTTVTVSSGGGGSGGGGSGGGGSDIELTQSPKFMST

SVGDRVSVTCKASQNVGTNVAWYQQKPGQSPKPLIYSATYRNSGVPDRFT

GSGSGTDFTLTITNVQSKDLADYFCQQYNRYPYTSGGGTKLEIKR.

In some embodiments, the scFv comprises a polypeptide having an amino acid sequence of SEQ ID NO: 4, which includes a signal sequence.

(SEQ ID NO: 4)
MALPVTALLLPLALLLHAEVKLQQSGAELVRPGSSVKISCKASGYAFSSY

WMNWVKQRPGQGLEWIGQIYPGDGDTNYNGKFKGQATLTADKSSSTAYMQ

LSGLTSEDSAVYFCARKTISSVVDFYFDYWGQGTTVTVSSGGGGSGGGGS

GGGGSDIELTQSPKFMSTSVGDRVSVTCKASQNVGTNVAWYQQKPGQSPK

PLIYSATYRNSGVPDRFTGSGSGTDFTLTITNVQSKDLADYFCQQYNRYP

YTSGGGTKLEIKR.

In some embodiments, the scFv comprises a polypeptide having an amino acid sequence that is at least 80%, at least 85%, at least 90%, or at least 95% identical to SEQ ID NO: 3 or SEQ ID NO: 4. For example, the scFv comprises a polypeptide having an amino acid sequence that is about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or SEQ ID NO: 4.

In some embodiments, the scFv is encoded by a nucleic acid having a nucleic acid sequence of SEQ ID NO: 5.

(SEQ ID NO: 5)
GAGGTGAAGCTGCAGCAGTCTGGGGCTGAGCTGGTGAGGCCTGGGTCCTC

AGTGAAGATTTCCTGCAAGGCTTCTGGCTATGCATTCAGTAGCTACTGGA

TGAACTGGGTGAAGCAGAGGCCTGGACAGGGTCTTGAGTGGATTGGACAG

ATTTATCCTGGAGATGGTGATACTAACTACAATGGAAAGTTCAAGGGTCA

AGCCACACTGACTGCAGACAAATCCTCCAGCACAGCCTACATGCAGCTCA

GCGGCCTAACATCTGAGGACTCTGCGGTCTATTTCTGTGCAAGAAAGACC

ATTAGTTCGGTAGTAGATTTCTACTTTGACTACTGGGGCCAAGGGACCAC

GGTCACCGTCTCCTCAGGTGGAGGTGGATCAGGTGGAGGTGGATCTGGTG

GAGGTGGATCTGACATTGAGCTCACCCAGTCTCCAAAATTCATGTCCACA

TCAGTAGGAGACAGGGTCAGCGTCACCTGCAAGGCCAGTCAGAATGTGGG

TACTAATGTAGCCTGGTATCAACAGAAACCAGGACAATCTCCTAAACCAC

TGATTTACTCGGCAACCTACCGGAACAGTGGAGTCCCTGATCGCTTCACA

GGCAGTGGATCTGGGACAGATTTCACTCTCACCATCACTAACGTGCAGTC

TAAAGACTTGGCAGACTATTTCTGTCAACAATATAACAGGTATCCGTACA

CGTCCGGAGGGGGGACCAAGCTGGAGATCAAACGGGCGGCCGCA.

In some embodiments, the scFv is encoded by a nucleic acid having a nucleic acid sequence of SEQ ID NO: 6:

(SEQ ID NO: 6)
ATGGCTCTCCCAGTGACTGCCCTACTGCTTCCCCTAGCGCTTCTCCTGCA

TGCAGAGGTGAAGCTGCAGCAGTCTGGGGCTGAGCTGGTGAGGCCTGGGT

CCTCAGTGAAGATTTCCTGCAAGGCTTCTGGCTATGCATTCAGTAGCTAC

TGGATGAACTGGGTGAAGCAGAGGCCTGGACAGGGTCTTGAGTGGATTGG

ACAGATTTATCCTGGAGATGGTGATACTAACTACAATGGAAAGTTCAAGG

GTCAAGCCACACTGACTGCAGACAAATCCTCCAGCACAGCCTACATGCAG

CTCAGCGGCCTAACATCTGAGGACTCTGCGGTCTATTTCTGTGCAAGAAA

GACCATTAGTTCGGTAGTAGATTTCTACTTTGACTACTGGGGCCAAGGGA

CCACGGTCACCGTCTCCTCAGGTGGAGGTGGATCAGGTGGAGGTGGATCT

GGTGGAGGTGGATCTGACATTGAGCTCACCCAGTCTCCAAAATTCATGTC

CACATCAGTAGGAGACAGGGTCAGCGTCACCTGCAAGGCCAGTCAGAATG

TGGGTACTAATGTAGCCTGGTATCAACAGAAACCAGGACAATCTCCTAAA

CCACTGATTTACTCGGCAACCTACCGGAACAGTGGAGTCCCTGATCGCTT

CACAGGCAGTGGATCTGGGACAGATTTCACTCTCACCATCACTAACGTGC

AGTCTAAAGACTTGGCAGACTATTTCTGTCAACAATATAACAGGTATCCG

TACACGTCCGGAGGGGGGACCAAGCTGGAGATCAAACGG.

In some embodiments, the scFv is encoded by a nucleic acid having a nucleic acid sequence that is at least 80%, at least 85%, at least 90%, or at least 95% identical to SEQ ID NO: 5 or SEQ ID NO: 6. In some embodiments, the scFv is encoded by a nucleic acid having a nucleic acid sequence of SEQ ID NO: 5 or SEQ ID NO: 6. In some embodiments, the scFv is encoded by a nucleic acid having a nucleic acid sequence that is about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5 or SEQ ID NO: 6.

In certain embodiments, the extracellular antigen-binding domain comprises a human scFv that binds to a MUC16 antigen. In some embodiments, the scFv comprises a polypeptide having an amino acid sequence of SEQ ID NO: 41.

(SEQ ID NO: 41)
QVTLKESGPGILQPSQTLSLTCSFSGFSLSTVGMGVGWSRQPSGKGLEWL

AHIWWDDEDKYYNPALKSRLTISKDTSKNQVFLKIANVDTADTATYYCTR

IGTAQATDALDYWGQGTSVTVSSGGGGSGGGGSGGGGSDIVMTQAAPSVP

VTPGESVSISCRSSKSLLHSNGNTYLYWFLQRPGQSPQRLIYYMSNLASG

VPDRFSGRGSGTDFTLRISRVEAEDVGVYYCMQSLEYPLTFGGGTKLEIK.

In some embodiments, the scFv comprises a $V_H$ domain sequence having an amino acid sequence of SEQ ID NO: 39.

(SEQ ID NO: 39)
QVTLKESGPGILQPSQTLSLTCSFSGFSLSTVGMGVGWSRQPSGKGLEWL

AHIWWDDEDKYYNPALKSRLTISKDTSKNQVFLKIANVDTADTATYYCTR

IGTAQATDALDYWGQGTSVTVSS.

In some embodiments, the scFv comprises a $V_L$ domain sequence having an amino acid sequence of SEQ ID NO: 40.

(SEQ ID NO: 40)
DIVMTQAAPSVPVTPGESVSISCRSSKSLLHSNGNTYLYAVFLQRPGQSP

QRLIYYMSNLASGVPDRFSGRGSGTDFTLRISRVEAEDVGVYYCMQSLEY

PLTFGGGTKLEIK.

In some embodiments, the scFv comprises a polypeptide having an amino acid sequence of SEQ ID NO: 44.

(SEQ ID NO: 44)
VKLQESGGGFVKPGGSLKVSCAASGFTFSSYAMSWVRLSPEMRLEWVATI

SSAGGYIFYSDSVQGRFTISRDNAKNTLHLQMGSLRSGDTAMYYCARQGF

GNYGDYYAMDYWGQGTTVTVSSGGGGSGGGGSGGGGSDIELTQSPSSLAV

SAGEKVTMSCKSSQSLLNSRTRKNQLAWYQQKPGQSPELLIYWASTRQSG

VPDRFTGSGSGTDFTLTISSVQAEDLAVYYCQQSYNLLTFGPGTKLEVKR.

In some embodiments, the scFv comprises a $V_H$ domain sequence having an amino acid sequence of SEQ ID NO: 42.

(SEQ ID NO: 42)
VKLQESGGGFVKPGGSLKVSCAASGFTFSSYAMSWVRLSPEMRLEWVATI

SSAGGYIFYSDSVQGRFTISRDNAKNTLHLQMGSLRSGDTAMYYCARQGF

GNYGDYYAMDYWGQGTTVTVSS.

In some embodiments, the scFv comprises a $V_L$ domain sequence having an amino acid sequence of SEQ ID NO: 43.

(SEQ ID NO: 43)
DIELTQSPSSLAVSAGEKVTMSCKSSQSLLNSRTRKNQLAWYQQKPGQSP

ELLIYWASTRQSGVPDRFTGSGSGTDFTLTISSVQAEDLAVYYCQQSYNL

LTFGPGTKLEVKR.

In some embodiments, the scFv comprises a polypeptide having an amino acid sequence that is at least 80%, at least 85%, at least 90%, or at least 95% identical to SEQ ID NO: 41 or SEQ ID NO: 44. For example, the scFv comprises a polypeptide having an amino acid sequence that is about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 41 or SEQ ID NO: 44.

In some embodiments, the scFv comprises an scFv of an anti-MUC16 antibody disclosed in WO2011/119979 or WO2016/149368. In some embodiments, the anti-MUC16 scFv comprises a heavy chain variable region and a light chain variable region of an anti-MUC16 antibody disclosed in WO2011/119979 or WO2016/149368. In some embodiments, the anti-MUC16 scFv comprises a heavy chain variable region and a light chain variable region of an anti-MUC16 antibody selected from among 4H11, 18C6, 4A5, 9B11, 10A2, 2F4, 23D3, 30B1, 31B2, 13H1, 29G9, 9C9, 28F8, 23G12, 9C7, 11B6, 25G4, 5C2, 4C7, 26B2, 4A2, 25H3, 28F7, 31A3, 19D1, 10F6, 22E10, 22F1, 3H8, 22F11, 4D7, 24G12, 19G4, 9A5, 4C2, 31C8, 27G4, 6H2, 24B3, 23D4, 4F12, 6H6, 25C2, 6E8, 2A3, 2G4, 4C8, 2A6, 15D5, 6E2, 7E6, 7G11, 20C3, 9A3, 15B6, 19D3, 5H8, 24A12, 2D10, 5B2, 8B6, 5A11, 7D11, 9F10, 15D10, 18D2, 13A11, 1A9, 3B2, 24F6, 5A1, 7B9, 22F4, 10C6, 7B12, 19C11, 16C5, 12B10 disclosed in WO2011/119979 or WO2016/149368.

In certain non-limiting embodiments, an extracellular antigen-binding domain of the presently disclosed CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence set forth in SEQ ID NO: 1. In certain embodiments, the nucleotide sequence encoding the amino acid sequence of SEQ ID NO: 1 is set forth in SEQ ID NO: 2.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway.

In certain embodiments, the signal peptide is covalently joined to the N-terminus of the extracellular antigen-binding domain. In certain embodiments, the signal peptide comprises a CD8 signal polypeptide comprising amino acids having the sequence set forth in SEQ ID NO: 7 as provided below:

(SEQ ID NO: 7)
MALPVTALLLPLALLLHAARP.

The nucleotide sequence encoding the amino acid sequence of SEQ ID NO: 7 is set forth in SEQ ID NO: 8, which is provided below: atggccctgccagtaacggctctgctgctgccacttgctctgctcctccatgcagccaggcct (SEQ ID NO: 8).

In certain embodiments, the signal peptide comprises a CD8 signal polypeptide comprising amino acids having the sequence set forth in SEQ ID NO: 9 as provided below:

(SEQ ID NO: 9)
MALPVTALLLPLALLLHA.

The nucleotide sequence encoding the amino acid sequence of SEQ ID NO: 9 is set forth in SEQ ID NO: 10, which is provided below:

(SEQ ID NO: 10)
ATGGCTCTCCCAGTGACTGCCCTACTGCTTCCCCTAGCGCTTCTCCTGCA

TGCA.

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (e.g., a transmembrane peptide not based on a protein associated with the immune response), or a combination thereof.

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: PI0747 or NP006130 (SEQ ID NO: 11), or fragments thereof, and/or may optionally comprise up to one or up to two or up to three conservative amino acid substitutions. In certain embodiments, the CD28 polypeptide can have an amino acid sequence that is a consecutive portion of SEQ ID NO: 11 which is at least 20, or at least 30, or at least 40, or at least 50, and up to 220 amino acids in length. Alternatively, or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO: 11. In certain embodiments, the CAR of the presently disclosed comprises a transmembrane domain comprising a CD28 polypeptide, and an intracellular domain comprising a co-stimulatory signaling region that comprises a CD28 polypeptide. In certain embodiments, the CD28 polypeptide comprised in the transmembrane domain and the intracellular domain has an amino acid sequence of amino acids 114 to 220 of SEQ ID NO: 11.

SEQ ID NO: 11 is provided below:

(SEQ ID NO: 11)
MLRLLLALNLFPSIQVTGNKILVKQSPMLVAYDNALSCKYSYNLFSREFR

ASLHKGLDSAVEVCWYGNYSQQLQVYSKTGFNCDGKLGNESVTFYLQNLY

QTDIYFCKIEVMYPPPYLDNEKSNGTIIHVKGKHLCPSPLFPGPSKPFWV

LVWGGVLACYSLLVTVAFIIFWVRSKRSRLLHSDYMNMTPRRPGPTRKHY

QPYAPPRDFAAYRS

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide comprised in the transmembrane domain and the intracellular domain (e.g., the co-stimulatory signaling region) of the presently disclosed CAR (amino acids 114 to 220 of SEQ ID NO: 11) comprises nucleic acids having the sequence set forth in SEQ ID NO: 12 as provided below.

(SEQ ID NO: 12)
attgaagttatgtatcctcctccttacctagacaatgagaagagcaatg gaaccattatccatgtgaaagggaaacacctttgtccaagtcccctatt tcccggaccttctaagcccttttgggtgctggtggtggttggtggagtc ctggcttgctatagcttgctagtaacagtggcctttattattttctggg tgaggagtaagaggagcaggctectgcacagtgactacatgaacatgac tccccgccgccccgggcccacccgcaagcattaccagccctatgcccca ccacgcgacttcgcagcctatcgctcc In certain embodiments, the transmembrane domain comprises a CD8 polypeptide. The CD8 polypeptide can have an amino acid sequence that is at least about 85%, about 90%, about 95%, about 96%, about 97%, about 98%, about 99% or about 100%) homologous to SEQ ID NO: 13 (homology herein may be determined using standard software such as BLAST or FASTA) as provided below, or fragments thereof, and/or may optionally comprise up to one or up to two or up to three conservative amino acid substitutions. In certain embodiments, the CD8 polypeptide can have an amino acid sequence that is a consecutive portion of SEQ ID NO: 13 which is at least 20, or at least 30, or at least 40, or at least 50, and up to 235 amino acids in length. Alternatively, or additionally, in various embodiments, the CD8 polypeptide has an amino acid sequence of amino acids 1 to 235, 1 to 50, 50 to 100, 100 to 150, 150 to 200, or 200 to 235 of SEQ ID NO: 13.

(SEQ ID NO: 13)
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAVHTRGLDFACDIYIWAPLAGTCGVLLLSL

VITLYCNHRNRRRVCKCPRPWKSGDKPSLSARYV

In certain embodiments, the transmembrane domain comprises a CD8 polypeptide comprising amino acids having the sequence set forth in SEQ ID NO: 14 as provided below:

(SEQ ID NO: 14)
PTTTPAPRPPTPAPTIASQPLSLRPEACRPAAGGAVHTRGLDFACDIYIW

APLAGTCGVLLLSLVITLYCN

In accordance with the presently disclosed subject matter, a "CD8 nucleic acid molecule" refers to a polynucleotide encoding a CD8 polypeptide. In certain embodiments, the CD8 nucleic acid molecule encoding the CD8 polypeptide comprised in the transmembrane domain of the presently disclosed CAR (SEQ ID NO: 14) comprises nucleic acids having the sequence set forth in SEQ ID NO: 15 as provided below.

(SEQ ID NO: 15)
CCCACCACGACGCCAGCGCCGCGACCACCAACCCCGGCGCCCACGATCGC

GTCGCAGCCCCTGTCCCTGCGCCCAGAGGCGTGCCGGCCAGCGGCGGGGG

GCGCAGTGCACACGAGGGGGCTGGACTTCGCCTGTGATATCTACATCTGG

GCGCCCCTGGCCGGGACTTGTGGGGTCCTTCTCCTGTCACTGGTTATCAC

CCTTTACTGCAAC

In certain non-limiting embodiments, a CAR can also comprise a spacer region that links the extracellular antigen-binding domain to the transmembrane domain. The spacer region can be flexible enough to allow the antigen-binding domain to orient in different directions to facilitate antigen recognition while preserving the activating activity of the CAR. In certain non-limiting embodiments, the spacer region can be the hinge region from IgGl, the $CH_2CH_3$ region of immunoglobulin and portions of CD3, a portion of a CD28 polypeptide (e.g., SEQ ID NO: 11), a portion of a CD8 polypeptide (e.g., SEQ ID NO: 13), a variation of any of the foregoing which is at least about 80%, at least about 85%>, at least about 90%, or at least about 95% homologous thereto, or a synthetic spacer sequence. In certain non-limiting embodiments, the spacer region may have a length between about 1-50 (e.g., 5-25, 10-30, or 30-50) amino acids.

Intracellular Domain of a CAR

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence having a NCBI Reference No: NP_932170 (SEQ ID No: 16), or fragments thereof, and/or may optionally comprise up to one or up to two or up to three conservative amino acid substitutions. In certain embodiments, the CD3ζ polypeptide can have an amino acid sequence that is a consecutive portion of SEQ ID NO: 17 which is at least 20, or at least 30, or at least 40, or at least 50, and up to 164 amino acids in length. Alternatively, or additionally, in various embodiments, the CD3ζ polypeptide has an amino acid sequence of amino acids 1 to 164, 1 to 50, 50 to 100, 100 to 150, or 150 to 164 of SEQ ID NO: 17. In certain embodiments, the CD3ζ polypeptide has an amino acid sequence of amino acids 52 to 164 of SEQ ID NO: 17.

SEQ ID NO: 17 is provided below:

```
                                         (SEQ ID NO: 17)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR
```

In certain embodiments, the CD3ζ polypeptide has the amino acid sequence set forth in SEQ ID NO: 18, which is provided below:

```
                                         (SEQ ID NO: 18)
RVKFSRSAEPPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
```

In certain embodiments, the CD3ζ polypeptide has the amino acid sequence set forth in SEQ ID NO: 19, which is provided below:

```
                                         (SEQ ID NO: 19)
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTAT

KDTYDALHMQALPPR
```

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide (SEQ ID NO: 18) comprised in the intracellular domain of the presently disclosed CAR comprises a nucleotide sequence as set forth in SEQ ID NO: 20 as provided below.

```
                                         (SEQ ID NO: 20)
agagtgaagttcagcaggagcgcagagcccccccgcgtaccagcagggcc

agaaccagctctataacgagctcaatctaggacgaagagaggagtacga
```

-continued

```
tgttttggacaagagacgtggccgggaccctgagatgggggggaaagccg

agaaggaagaaccctcaggaaggcctgtacaatgaactgcagaaagata

agatggcggaggcctacagtgagattgggatgaaaggcgagcgccggag

gggcaaggggcacgatggcctttaccagggtctcagtacagccaccaag

gacacctacgacgccettcacatgcaggccctgccccctcgcg
```

In certain embodiments, the CD3ζ nucleic acid molecule encoding the CD3ζ polypeptide (SEQ ID NO: 19) comprised in the intracellular domain of the presently disclosed CAR comprises a nucleotide sequence as set forth in SEQ ID NO: 21 as provided below.

```
                                         (SEQ ID NO: 21)
AGAGTGAAGTTCAGCAGGAGCGCAGACGCCCCCGCGTACCAGCAGGG

CCAGAACCAGCTCTATAACGAGCTCAATCTAGGACGAAGAGAGGAGTAC

GATGTTTTGGACAAGAGACGTGGCCGGGACCCTGAGATGGGGGGAAAGC

CGAGAAGGAAGAACCCTCAGGAAGGCCTGTACAATGAACTGCAGAAAGA

TAAGATGGCGGAGGCCTACAGTGAGATTGGGATGAAAGGCGAGCGCCGG

AGGGGCAAGGGGCACGATGGCCTTTACCAGGGTCTCAGTACAGCCACCA

AGGACACCTACGACGCCCTTCACATGCAGGCCCTGCCCCCTCGCTAA
```

In certain non-limiting embodiments, an intracellular domain of the CAR further comprises at least one signaling region. The at least one signaling region can include a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region.

In certain embodiments, the co-stimulatory signaling region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD 137") for providing an intracellular signal that in combination with a CAR signal induces an effector cell function of the $CAR^+$ T cell. CARs comprising an intracellular domain that comprises a co-stimulatory signaling region comprising 4-1BB, ICOS or DAP-10 are disclosed in U.S. Pat. No. 7,446,190, which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules: CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO: 22) or fragments thereof, and/or may optionally comprise up to one or up to two or up to three conservative amino acid substitutions.

SEQ ID NO: 22 is provided below:

```
                                          (SEQ ID NO: 22)
MGNSCYNIVATLLLVLNFERTRSLQDPCSNCPAGTFCDNNRNQICSPCP

PNSFSSAGGQRTCDICRQCKGVFRTRKECSSTSNAECDCTPGFHCLGAG

CSMCEQDCKQGQELTKKGCKDCCFGTFNDQKRGICRPWTNCSLDGKSVL

GTKERDWCGPSPADLSPGASSVTPPAPAREPGHSPQIISFFLALTSTAL

LFLLFFLTLRFSWKRGRKKLLYIFKQPFMRPVQTTQEEDGCSCRFPEEE

EGGCEL.
```

In certain embodiments, the 4-1BB co-stimulatory domain has the amino acid sequence set forth in SEQ ID NO: 23, which is provided below:

```
                                          (SEQ ID NO: 23)
  KRGRKKLLYIFKQPFMRPVQTTQEEDGCSCRFPEEEEGGCEL
```

In accordance with the presently disclosed subject matter, a "4-1BB nucleic acid molecule" refers to a polynucleotide encoding a 4-1BB polypeptide. In certain embodiments, the 4-1BB nucleic acid molecule encoding the 4-1BB polypeptide (SEQ ID NO: 23) comprised in the intracellular domain of the presently disclosed CAR comprises a nucleotide sequence as set forth in SEQ ID NO: 24 as provided below.

```
                                          (SEQ ID NO: 24)
AAACGGGGCAGAAAGAAGCTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG.
```

An OX40 polypeptide can have an amino acid sequence that is at least about 85%, about 90%, about 95%, about 96%, about 97%, about 98%, about 99% or 100% homologous to the sequence having a NCBI Reference No: P43489 or NP 003318 (SEQ ID NO: 25), or fragments thereof, and/or may optionally comprise up to one or up to two or up to three conservative amino acid substitutions.

SEQ ID NO: 25 is provided below:

```
                                          (SEQ ID NO: 25)
MCVGARRLGRGPCAALLLLGLGLSTVTGLHCVGDTYPSNDRCCHECRPG

NGMVSRCSRSQNTVCRPCGPGFYNDWSSKPCKPCTWCNLRSGSERKQLC

TATQDTVCRCRAGTQPLDSYKPGVDCAPCPPGHFSPGDNQACKPWTNCT

LAGKHTLQPASNSSDAICEDRDPPATQPQETQGPPARPITVQPTEAWPR

TSQGPSTRPVEVPGGRAVAAILGLGLVLGLLGPLAILLALYLLRRDQRL

PPDAHKPPGGGSFRTPIQEEQADAHSTLAKI.
```

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP_036224 (SEQ ID NO: 26) or fragments thereof, and/or may optionally comprise up to one or up to two or up to three conservative amino acid substitutions.

SEQ ID NO: 26 is provided below:

```
                                          (SEQ ID NO: 26)
MKSGLWYFFLFCLRIKVLTGEINGSANYEMFIFHNGGVQILCKYPDIVQ

QFKMQLLKGGQILCDLTKTKGSGNTVSIKSLKFCHSQLSNNSVSFFLYN

LDHSHANYYFCNLSIFDPPPFKVTLTGGYLHIYESQLCCQLKFWLPIGC

AAFVWCILGCILICWLTKKKYSSSVHDPNGEYMFMRATAKKSRLTDVTL
```

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif (SEQ ID NO: 45) able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 27) (homology herein may be determined using standard software such as BLAST or FASTA) or fragments thereof, and/or may optionally comprise up to one or up to two or up to three conservative amino acid substitutions.

SEQ ID NO: 27 is provided below:

```
                                          (SEQ ID NO: 27)
MACLGFQRHKAQLNLATRTWPCTLLFFLLFIPVFCKAMHVAQPAWLASS

RGIASFVCEYASPGKATEVRVTVLRQADSQVTEVCAATYMMGNELTFLD

DSICTGTSSGNQLTIQGLRAMDTGLYICKVELMYPPPYYLGIGNGTQIY

VIDPEPCPDSDFLLWILAAVSSGLFFYSFLLTAVSLSKMLKKRSPLTTG

VYVKMPPTEPECEKQFQPYFIPIN.
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system. In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP_005009.2 (SEQ ID NO: 28) or fragments thereof, and/or may optionally comprise up to one or up to two or up to three conservative amino acid substitutions.

SEQ ID NO: 28 is provided below:

```
                                        (SEQ ID NO: 28)
MQIPQAPWPVVWAVLQLGWRPGWFLDSPDRPWNPPTFSPALLWTEGDNA

TFTCSFSNTSESFVLNWYRMSPSNQTDKLAAFPEDRSQPGQDCRFRVTQ

LPNGRDFHMSVVRARRNDSGTYLCGAISLAPKAQIKESLRAELRVTERR

AEVPTAHPSPSPRPAGQFQTLVVGWGGLLGSLVLLVWVLAVICSRAARG

TIGARRTGQPLKEDPSAVPVFSVDYGELDFQWREKTPEPPVPCVPEQTE

YATIVFPSGMGTSSPARRGSADGPRSAQPLRPEDGHCSWPL.
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 29) or fragments thereof, and/or may optionally comprise up to one or up to two or up to three conservative amino acid substitutions.

SEQ ID NO: 29 is provided below:

```
                                                 (SEQ ID NO: 29)
MWEAQFLGLLFLQPLWVAPVKPLQPGAEVPVVWAQEGAPAQLPCSPTIPL

QDLSLLRRAGVTWQHQPDSGPPAAAPGHPLAPGPHPAAPSSWGPRPRRY

TVLSVGPGGLRSGRLPLQPRVQLDERGRQRGDFSLWLRPARRADAGEYR

AAVHLRDRALSCRLRLRLGQASMTASPPGSLRASDWVILNCSFSRPDRP

ASVHWFRNRGQGRVPVRESPHHHLAESFLFLPQVSPMDSGPWGCILTYR

DGFNVSIIVIYNLTVLGLEPPTPLTVYAGAGSRVGLPCRLPAGVGTRSF

LTAKWTPPGGGPDLLVTGDNGDFTLRLEDVSQAQAGTYTCHIHLQEQQL

NATVTLAIITVTPKSFGSPGSLGKLLCEVTPVSGQERFVWSSLDTPSQR

SFSGPWLEAQEAQLLSQPWQCQLYQGERLLGAAVYFTELSSPGAQRSGR

APGALPAGHLLLFLILGVLSLLLLVTGAFGFHLWRRQWRPRRFSALEQG

IHPPQAQSKIEELEQEPEPEPEPEPEPEPEPEPEQL.
```

In accordance with the presently disclosed subject matter, a "LAG-3 nucleic acid molecule" refers to a polynucleotide encoding a LAG-3 polypeptide. Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref No.: Q9BZW8.2 (SEQ ID NO: 30) or fragments thereof, and/or may optionally comprise up to one or up to two or up to three conservative amino acid substitutions.

SEQ ID NO: 30 is provided below:

```
                                                 (SEQ ID NO: 30)
MLGQWTLILLLLLKVYQGKGCQGSADHWSISGVPLQLQPNSIQTKVDSI

AWKKLLPSQNGFHHILKWENGSLPSNTSNDRFSFIVKNLSLLIKAAQQQ

DSGLYCLEVTSISGKVQTATFQVFVFESLLPDKVEKPRLQGQGKILDRG

RCQVALSCLVSRDGNVSYAWYRGSKLIQTAGNLTYLDEEVDINGTHTYT

CNVSNPVSWESHTLNLTQDCQNAHQEFRFWPFLVIIVILSALFLGTLAC

FCVWRRKRKEKQSETSPKEFLTIYEDVKDLKTRRNHEQEQTFPGGGSTI

YSMIQSQSSAPTSQEPAYTLYSLIQPSRKSGSRKRNHSPSENSTIYEVI

GKSQPKAQNPARLSRKELENFDVYS.
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human $CD8^+$ cancer-specific T cells. BTLA has also been designated as CD272 (cluster of differentiation 272).

In accordance with the presently disclosed subject matter, a BTLA polypeptide can have an amino acid sequence that is at least about 85%>, about 90%, about 95%, about 96%, about 97%, about 98%, about 99% or about 100% homologous to UniProtKB/Swiss-Prot Ref. No.: Q7Z6A9.3 (SEQ ID NO: 31) or fragments thereof, and/or may optionally comprise up to one or up to two or up to three conservative amino acid substitutions.

SEQ ID NO: 31 is provided below:

```
                                        (SEQ ID NO: 31)
MKTLPAMLGTGKLFWVFFLIPYLDIWNIHGKESCDVQLYIKRQSEHSIL

AGDPFELECPVKYCANRPHVTWCKLNGTTCVKLEDRQTSWKEEKNISFF

ILHFEPVLPNDNGSYRCSANFQSNLIESHSTTLYVTDVKSASERPSKDE

MASRPWLLYRLLPLGGLPLLITTCFCLFCCLRRHQGKQNELSDTAGREI

NLVDAHLKSEQTEASTRQNSQVLLSETGIYDNDPDLCFRMQEGSEVYSN

PCLEENKPGIVYASLNHSVIGPNSRLARNVKEAPTEYASICVRS.
```

In accordance with the presently disclosed subject matter, a "BTLA nucleic acid molecule" refers to a polynucleotide encoding a BTLA polypeptide.

Exemplary CAR and SIRPα Polypeptide Constructs

In certain embodiments, the CAR and SIRPα polypeptide are expressed as single polypeptide linked by a self-cleaving linker, such as a P2A linker. In certain embodiments, the CAR and SIRPα polypeptide are expressed as two separate polypeptides.

Figure 3:
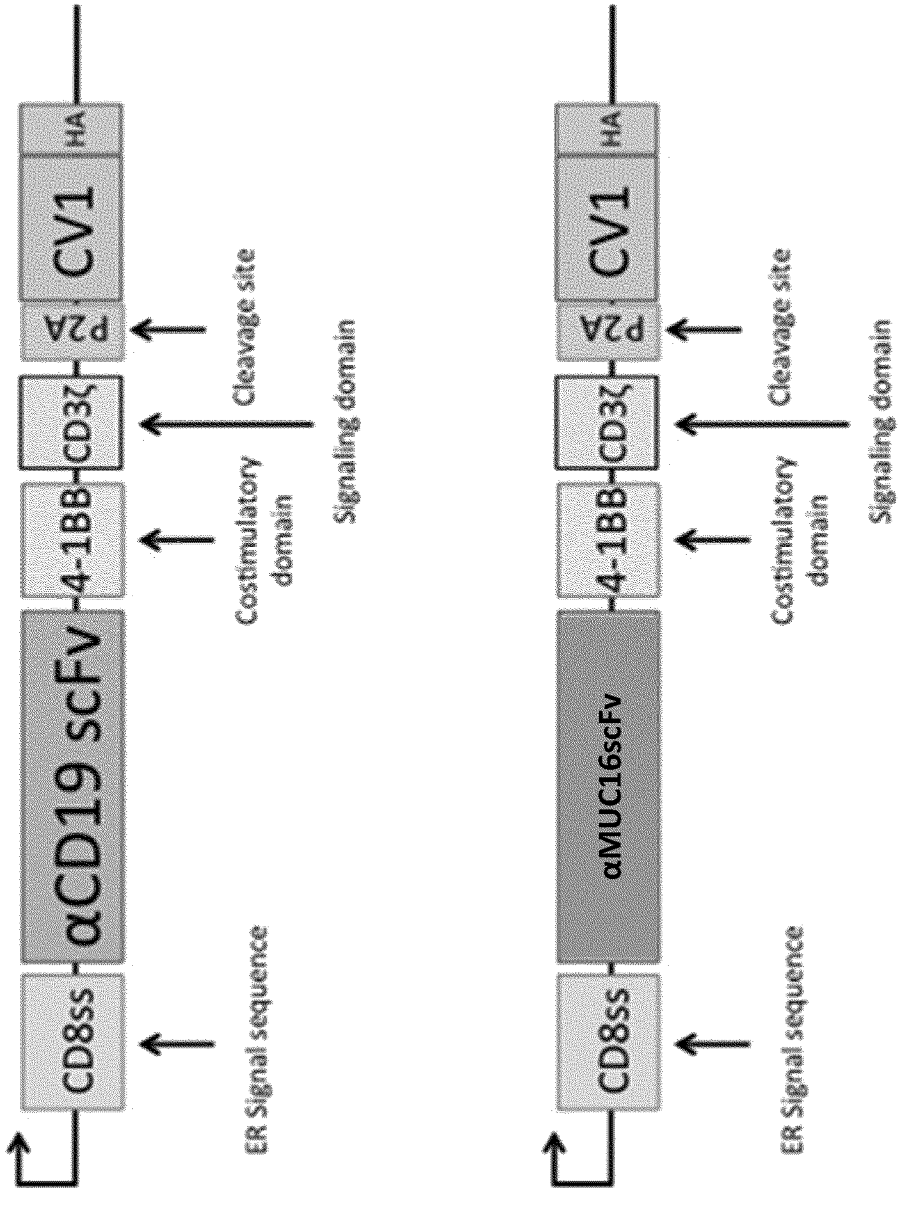
FIG. 3 shows a schematic of exemplary OrexiCAR gene constructs. CD8 leader sequence drives aCD19 or αMUC16 scFv into the ER for surface expression. The CD3ζ chain signals for T cell activation and proliferation upon antigen recognition, which is improved by the 4-1BB costimulatory domain. Self-cleaving peptide, P2A, releases CV1, with HA tag for detection, from the rest of the construct.

In certain embodiments, the CAR comprises an extracellular antigen-binding region that comprises a human scFv that specifically binds to a human tumor antigen, a transmembrane domain comprising a CD28 polypeptide and/or a CD8 polypeptide, and an intracellular domain comprising a CD3ζ polypeptide and a co-stimulatory signaling region that comprises a 4-1BB polypeptide, as shown in FIG. 3. As shown in FIG. 3, the CAR also comprises a signal peptide or a leader covalently joined to the N-terminus of the extracellular antigen-binding domain. The signal peptide comprises amino acids having the sequence set forth in SEQ ID NO: 7 or SEQ ID NO: 9. In certain embodiments, the human scFv is selected from the group consisting of an anti-BCMA scFv, an anti-CD19 scFv, an anti-mesothelin scFv, an anti-MUC16 scFv, an anti-PSCA scFv, an anti-WT1 scFv, and an anti-PRAME scFv. In some embodiments, the CD3ζ polypeptide comprises amino acids having the sequence set forth in SEQ ID NO: 19.

In some embodiments, the nucleic acid encoding the CAR and the SIRPα polypeptide (e.g., CV1) is operably linked to an inducible promoter. In some embodiments, the nucleic acid encoding the CAR and the SIRPα polypeptide (e.g., wild-type SIRPα or a fragment thereof, or a variant SIRPα (e.g., CV1) is operably linked to a constitutive promoter. In some embodiments, the nucleic acid encoding the CAR and the nucleic acid encoding SIRPα polypeptide (e.g., wild-type SIRPα or a fragment thereof, or a variant SIRPα (e.g., CV1) are operably linked to two separate promoters. In some embodiments, the nucleic acid encoding the CAR is operably linked to a constitutive promoter and the SIRPα polypeptide (e.g., wild-type SIRPα or a fragment thereof, or a variant SIRPα (e.g., CV1) is operably linked to a constitutive promoter. In some embodiments, the nucleic acid encoding the CAR is operably linked to a constitutive promoter and the SIRPα polypeptide (e.g., wild-type SIRPα or a fragment thereof, or a variant SIRPα or a fragment thereof (e.g., CV1) is operably linked to an inducible promoter.

In some embodiments, the inducible promoter is a synthetic Notch promoter that is activatable in a CAR T cell, where the intracellular domain of the CAR contains a transcriptional regulator that is released from the membrane when engagement of the CAR with the tumor antigen induces intramembrane proteolysis (see, e.g. Morsut et al., *Cell* 164(4): 780-791 (2016). Accordingly, transcription of the SIRPα polypeptide is induced upon binding of the engineered immune cell with the tumor antigen.

The presently disclosed subject matter also provides isolated nucleic acid molecules encoding the CAR/SIRPα polypeptide constructs described herein or a functional portion thereof. In certain embodiments, the isolated nucleic acid molecule encodes an anti-CD19-targeted CAR comprising a human scFv that specifically binds to a human CD19 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1 (see, e.g., FIG. 3).

In certain embodiments, the isolated nucleic acid molecule encodes an anti-CD19-targeted CAR comprising a human scFv that specifically binds to a human CD19 polypeptide fused to a synthetic Notch transmembrane domain and an intracellular cleavable transcription factor. In certain embodiments, the isolated nucleic acid molecule encodes a SIRPα polypeptide inducible by release of the transcription factor of a synthetic Notch system.

In certain embodiments, the isolated nucleic acid molecule encodes an anti-MUC16-targeted CAR comprising a human scFv that specifically binds to a human MUC16 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1 (see, e.g., FIG. 3). In some embodiments, the isolated nucleic acid molecule encodes an anti-MUC16-targeted CAR comprising a human scFv that specifically binds to a human MUC16 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a wild-type SIRPα or a fragment thereof or a variant SIRPα or a fragment thereof.

In certain embodiments, the isolated nucleic acid molecule encodes an anti-mesothelin-targeted CAR comprising a human scFv that specifically binds to a human mesothelin polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1. In some embodiments, the isolated nucleic acid molecule encodes an anti-mesothelin-targeted CAR comprising a human scFv that specifically binds to a human mesothelin polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a wild-type SIRPα or a fragment thereof or a variant SIRPα or a fragment thereof.

In certain embodiments, the isolated nucleic acid molecule encodes an anti-WT1-targeted CAR comprising a human scFv that specifically binds to a human WT1 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1. In some embodiments, the isolated nucleic acid molecule encodes an anti-WT-1-targeted CAR comprising a human scFv that specifically binds to a human WT-1 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a wild-type SIRPα or a fragment thereof or a variant SIRPα or a fragment thereof.

In certain embodiments, the isolated nucleic acid molecule encodes an anti-PSCA-targeted CAR comprising a human scFv that specifically binds to a human PSCA polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1. In some embodiments, the isolated nucleic acid molecule encodes an anti-PSCA-targeted CAR comprising a human scFv that specifically binds to a human PSCA polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a wild-type SIRPα or a fragment thereof or a variant SIRPα or a fragment thereof.

In certain embodiments, the isolated nucleic acid molecule encodes an anti-BCMA-targeted CAR comprising a human scFv that specifically binds to a human BCMA polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and CV1. In some embodiments, the isolated nucleic acid molecule encodes an anti-BCMA-targeted CAR comprising a human scFv that specifically binds to a human BCMA polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a wild-type SIRPα or a fragment thereof or a variant SIRPα or a fragment thereof.

In certain embodiments, the isolated nucleic acid molecule encodes a functional portion of a presently disclosed CAR constructs. As used herein, the term "functional portion" refers to any portion, part or fragment of a CAR, which portion, part or fragment retains the biological activity of the targeted CAR (the parent CAR). For example, functional portions encompass the portions, parts or fragments of a tumor antigen-targeted CAR that retains the ability to recognize a target cell, to treat a disease, e.g., solid tumor, to a similar, same, or even a higher extent as the parent CAR. In certain embodiments, an isolated nucleic acid molecule encoding a functional portion of a tumor antigen-targeted CAR can encode a protein comprising, e.g., about 10%, about 20%, about 25%, about 30%, about 35%, about 40%, about 45%, about 50%, about 55%, about 60%, about 65%, about 70%, about 75%, about 80%, about 85%, about 90%, and about 95%, or more of the parent CAR.

Immune Cells

The presently disclosed subject matter provides engineered immune cells expressing a SIRPα polypeptide and a T-cell receptor (e.g., a CAR) or other ligand that comprises an extracellular antigen-binding domain, a transmembrane domain and an intracellular domain, where the extracellular antigen-binding domain specifically binds tumor antigen, including a tumor receptor or ligand, as described above. In certain embodiments immune cells can be transduced with a presently disclosed CAR/SIRPα polypeptide construct such that the cells express the CAR and the SIRPα polypeptide. The presently disclosed subject matter also provides methods of using such cells for the treatment of a tumor. The engineered immune cells of the presently disclosed subject matter can be cells of the lymphoid lineage or myeloid lineage. Non-limiting examples of immune cells of the myeloid lineage include neutrophils, monocytes, macrophages, eosinophils, erythrocytes, megakaryocytes, and platelets. The lymphoid lineage, comprising B, T, and natural killer (NK) cells, provides for the production of antibodies, regulation of the cellular immune system, detection of foreign agents in the blood, detection of cells foreign to the host, and the like. Non-limiting examples of immune cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and TEMRA cells, Regulatory T cells (also known as suppressor T cells), Natural killer T cells, Mucosal associated invariant T cells, and T6 T cells. Cytotoxic T cells (CTL or killer T cells) are a subset of T lymphocytes capable of inducing the death of infected somatic or tumor cells. In certain embodiments, the CAR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

The engineered immune cells of the presently disclosed subject matter may be white blood cells (e.g., T cells, B cells, neutrophils, NK cells, etc.)

The engineered immune cells of the presently disclosed subject matter can express an extracellular antigen-binding domain (e.g., a human scFv, a Fab that is optionally cross-linked, or a $F(ab)_2$) that specifically binds to a tumor antigen, for the treatment of cancer, e.g., for treatment of solid tumor. Such engineered immune cells can be administered to a subject (e.g., a human subject) in need thereof for the treatment of cancer. In some embodiments, the immune cell is a lymphocyte, such as a T cell, a B cell or a natural killer (NK) cell. In certain embodiments, the engineered immune cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

Presently disclosed engineered immune cells can further include at least one recombinant or exogenous co-stimulatory ligand. For example, presently disclosed engineered immune cells can be further transduced with at least one co-stimulatory ligand, such that the engineered immune cells co-expresses or is induced to co-express the tumor antigen-targeted CAR and the at least one co-stimulatory ligand. The interaction between the tumor antigen-targeted CAR and at least one co-stimulatory ligand provides a non-antigen-specific signal important for full activation of an immune cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD 154, CD137L/4-1BBL, TNF-α, CD134L/OX40L/CD252, CD27L/CD70, Fas ligand (FasL), CD30L/CD153, tumor necrosis factor beta (TNFP)/lymphotoxin-alpha (LTa), lymphotoxin-beta O-TO), CD257/B cell-activating factor (B AFF)/Bly s/THANK/Tall-1, glucocorticoid-induced TNF Receptor ligand (GITRL), and T F-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the engineered immune cell comprises one recombinant co-stimulatory ligand that is 4-1BBL. In certain embodiments, the engineered immune cell comprises two recombinant co-stimulatory ligands that are 4-1BBL and CD80. CARs comprising at least one co-stimulatory ligand are described in U.S. Pat. No. 8,389,282, which is incorporated by reference in its entirety.

Furthermore, a presently disclosed engineered immune cells can further comprise at least one exogenous cytokine. For example, a presently disclosed engineered immune cell can be further transduced with at least one cytokine, such that the engineered immune cells secrete the at least one cytokine as well as expresses the tumor antigen-targeted CAR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The engineered immune cells can be generated from peripheral donor lymphocytes, e.g., those disclosed in Sadelain, M., et al., *Nat Rev Cancer* 3:35-45 (2003) (disclosing peripheral donor lymphocytes genetically modified to express CARs), in Morgan, R. A. et al., *Science* 314: 126-129 (2006) (disclosing peripheral donor lymphocytes genetically modified to express a full-length tumor antigen-recognizing T cell receptor complex comprising the α and β heterodimer), in Panelli et al. *J Immunol* 164:495-504 (2000); Panelli et al. *J Immunol* 164:4382-4392 (2000) (disclosing lymphocyte cultures derived from tumor infiltrating lymphocytes (TILs) in tumor biopsies), and in Dupont et al. *Cancer Res* 65:5417-5427 (2005); Papanicolaou et al. *Blood* 102:2498-2505 (2003) (disclosing selectively in v/Yro-expanded antigen-specific peripheral blood leukocytes employing artificial antigen-presenting cells (AAPCs) or pulsed dendritic cells). The engineered immune cells (e.g., T cells) can be autologous, non-autologous (e.g., allogeneic), or derived in vitro from engineered progenitor or stem cells.

In certain embodiments, presently disclosed engineered immune cells (e.g., T cells) expresses from about 1 to about 5, from about 1 to about 4, from about 2 to about 5, from about 2 to about 4, from about 3 to about 5, from about 3 to about 4, from about 4 to about 5, from about 1 to about 2, from about 2 to about 3, from about 3 to about 4, or from about 4 to about 5 vector copy numbers per cell of a presently disclosed tumor antigen-targeted CAR and/or SIRPα polypeptide.

For example, the higher the CAR expression level in an engineered immune cell, the greater cytotoxicity and cytokine production the engineered immune cell exhibits. An engineered immune cell (e.g., T cell) having a high tumor antigen-targeted CAR expression level can induce antigen-specific cytokine production or secretion and/or exhibit cytotoxicity to a tissue or a cell having a low expression level of tumor antigen-targeted CAR, e.g., about 2,000 or less, about 1,000 or less, about 900 or less, about 800 or less, about 700 or less, about 600 or less, about 500 or less, about 400 or less, about 300 or less, about 200 or less, about 100 or less of tumor antigen binding sites/cell. Additionally, or alternatively, the cytotoxicity and cytokine production of a presently disclosed engineered immune cell (e.g., T cell) are proportional to the expression level of tumor antigen in a target tissue or a target cell. For example, the higher the expression level of human tumor antigen in the target, the greater cytotoxicity and cytokine production the engineered immune cell exhibits.

As described herein, the co-expression of the SIRPα polypeptide increases the cytotoxic effect in the CAR T cells bystander killing of a target cancer cell that is either not engaged by the CAR T cell or is an antigen loss variant of the CAR. In certain embodiments, an engineered immune cells of the present disclosure exhibits a cytotoxic effect against tumor antigen-expressing cells that is at least about 2-times, about 3-times, about 4-times, about 5-times, about 6-times, about 7-times, about 8-times, about 9-times, about 10-times, about 20-times, about 30-times, about 40-times, about 50-times, about 60-times, about 70-times, about 80-times, about 90-times, or about 100-times, the cytotoxic effect in the absence of the SIRPα polypeptide.

The unpurified source of immune cells may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-immune cell initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography;

cytotoxic agents joined to or used in conjunction with a mAb, including, but not limited to, complement and cytotoxins; and panning with antibody attached to a solid matrix, e.g., plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

In some embodiments, the engineered immune cells comprise one or more additional modifications. For example, in some embodiments, the engineered immune cells comprise and express (is transduced to express) an antigen recognizing receptor that binds to a second antigen that is different than selected tumor antigen. The inclusion of an antigen recognizing receptor in addition to a presently disclosed CAR on the engineered immune cell can increase the avidity of the CAR or the engineered immune cell comprising thereof on a targeted cell, especially, the CAR is one that has a low binding affinity to a particular tumor antigen, e.g., a $K_d$ of about $2\times10^{-8}$ M or more, about $5\times10^{-8}$ M or more, about $8\times10^{-8}$ M or more, about $9\times10^{-8}$ M or more, about $1\times10^{-7}$ M or more, about $2\times10^{-7}$ M or more, or about $5\times10^{-7}$ M or more.

In certain embodiments, the antigen recognizing receptor is a chimeric co-stimulatory receptor (CCR). CCR is described in Krause, et al., *J. Exp. Med.* 188(4):619-626 (1998), and US20020018783, the contents of which are incorporated by reference in their entireties. CCRs mimic co-stimulatory signals, but unlike, CARs, do not provide a T-cell activation signal, e.g., CCRs lack a CD3ζ polypeptide. CCRs provide co-stimulation, e.g., a CD28-like signal, in the absence of the natural co-stimulatory ligand on the antigen-presenting cell. A combinatorial antigen recognition, i.e., use of a CCR in combination with a CAR, can augment T-cell reactivity against the dual-antigen expressing T cells, thereby improving selective tumor targeting. Kloss et al., describe a strategy that integrates combinatorial antigen recognition, split signaling, and, critically, balanced strength of T-cell activation and costimulation to generate T cells that eliminate target cells that express a combination of antigens while sparing cells that express each antigen individually (Kloss et al., *Nature Biotechnology* 31(1):71-75 (2013)). With this approach, T-cell activation requires CAR-mediated recognition of one antigen, whereas costimulation is independently mediated by a CCR specific for a second antigen. To achieve tumor selectivity, the combinatorial antigen recognition approach diminishes the efficiency of T-cell activation to a level where it is ineffective without rescue provided by simultaneous CCR recognition of the second antigen. In certain embodiments, the CCR comprises an extracellular antigen-binding domain that binds to an antigen different than selected tumor antigen, a transmembrane domain, and a co-stimulatory signaling region that comprises at least one co-stimulatory molecule, including, but not limited to, CD28, 4-1BB, OX40, ICOS, PD-1, CTLA-4, LAG-3, 2B4, and BTLA. In certain embodiments, the co-stimulatory signaling region of the CCR comprises one co-stimulatory signaling molecule. In certain embodiments, the one co-stimulatory signaling molecule is CD28. In certain embodiments, the one co-stimulatory signaling molecule is 4-1BB. In certain embodiments, the co-stimulatory signaling region of the CCR comprises two co-stimulatory signaling molecules. In certain embodiments, the two co-stimulatory signaling molecules are CD28 and 4-1BB. A second antigen is selected so that expression of both selected tumor antigen and the second antigen is restricted to the targeted cells (e.g., cancerous tissue or cancerous cells). Similar to a CAR, the extracellular antigen-binding domain can be a scFv, a Fab, a $F(ab)_2$; or a fusion protein with a heterologous sequence to form the extracellular antigen-binding domain. In certain embodiments, the CCR comprises a scFv that binds to CD138, transmembrane domain comprising a CD28 polypeptide, and a co-stimulatory signaling region comprising two co-stimulatory signaling molecules that are CD28 and 4-1BB.

In certain embodiments, the antigen recognizing receptor is a truncated CAR. A "truncated CAR" is different from a CAR by lacking an intracellular signaling domain. For example, a truncated CAR comprises an extracellular antigen-binding domain and a transmembrane domain, and lacks an intracellular signaling domain. In accordance with the presently disclosed subject matter, the truncated CAR has a high binding affinity to the second antigen expressed on the targeted cells, e.g., myeloma cells. The truncated CAR functions as an adhesion molecule that enhances the avidity of a presently disclosed CAR, especially, one that has a low binding affinity to tumor antigen, thereby improving the efficacy of the presently disclosed CAR or engineered immune cell (e.g., T cell) comprising thereof. In certain embodiments, the truncated CAR comprises an extracellular antigen-binding domain that binds to CD138, a transmembrane domain comprising a CD8 polypeptide. A presently disclosed T cell comprises or is transduced to express a presently disclosed CAR targeting tumor antigen and a truncated CAR targeting CD138. In certain embodiments, the targeted cells are solid tumor cells. In some embodiments, the engineered immune cells are further modified to suppress expression of one or more genes. In some embodiments, the engineered immune cells are further modified via genome editing. Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983 and 20130177960, the disclosures of which are incorporated by reference in their entireties. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. In some embodiments, the engineered immune cells are modified to disrupt or reduce expression of an endogenous T-cell receptor gene (see, e.g. WO 2014153470, which is incorporated by reference in its entirety). In some embodiments, the engineered immune cells are modified to result in disruption or inhibition of PD1, PDL-1 or CTLA-4 (see, e.g. U.S. Patent Publication 20140120622), or other immunosuppressive factors known in the art (Wu et al. (2015) *Oncoimmunology* 4(7): e1016700, Mahoney et al. (2015) *Nature Reviews Drug Discovery* 14, 561-584).

Vectors

Many expression vectors are available and known to those of skill in the art and can be used for expression of polypeptides provided herein. The choice of expression vector will be influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector in the cells.

Vectors also can contain additional nucleotide sequences operably linked to the ligated nucleic acid molecule, such as, for example, an epitope tag such as for localization, e.g. a hexa-his tag (SEQ ID NO: 46) or a myc tag, hemagglutinin tag or a tag for purification, for example, a GST fusion, and a sequence for directing protein secretion and/or membrane association.

Expression of the antibodies or antigen-binding fragments thereof can be controlled by any promoter/enhancer known in the art. Suitable bacterial promoters are well known in the art and described herein below. Other suitable promoters for mammalian cells, yeast cells and insect cells are well known in the art and some are exemplified below. Selection of the promoter used to direct expression of a heterologous nucleic acid depends on the particular application and is within the level of skill of the skilled artisan. Promoters which can be used include but are not limited to eukaryotic expression vectors containing the SV40 early promoter (Bernoist and Chambon, *Nature* 290:304-310(1981)), the promoter contained in the 3' long terminal repeat of Rous sarcoma virus (Yamamoto et al., *Cell* 22:787-797(1980)), the herpes thymidine kinase promoter (Wagner et al., *Proc. Natl. Acad. Sci. USA* 75: 1441-1445 (1981)), the regulatory sequences of the metallothionein gene (Brinster et al., *Nature* 296:39-42 (1982)); prokaryotic expression vectors such as the (3-lactamase promoter (Jay et al., *Proc. Natl. Acad. Sci. USA* 75:5543 (1981)) or the tac promoter (DeBoer et al., *Proc. Natl. Acad. Sci. USA* 50:21-25(1983)); see also "Useful Proteins from Recombinant Bacteria": in Scientific American 242:79-94 (1980)); plant expression vectors containing the nopaline synthetase promoter (Herrera-Estrella et al., *Nature* 505:209-213(1984)) or the cauliflower mosaic virus 35S RNA promoter (Gardner et al., *Nucleic Acids Res.* 9:2871(1981)), and the promoter of the photosynthetic enzyme ribulose bisphosphate carboxylase (Herrera-Estrella et al., *Nature* 510: 1 15-120(1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 55:639-646 (1984); Ornitz et al., *Cold Spring Harbor Symp. Quant. Biol.* 50:399-409 (1986); *MacDonald, Hepatology* 7:425-515 (1987)); insulin gene control region which is active in pancreatic beta cells (Hanahan et al., *Nature* 515: 115-122 (1985)), immunoglobulin gene control region which is active in lymphoid cells (Grosschedl et al., *Cell* 55:647-658 (1984); Adams et al., *Nature* 515:533-538 (1985); Alexander et al., *Mol. Cell Biol.* 7: 1436-1444 (1987)), mouse mammary tumor virus control region which is active in testicular, breast, lymphoid and mast cells (Leder et al., *Cell* 15:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-403 (1985)); Hammer et al., *Science* 255:53-58 (1987)), alpha-1 antitrypsin gene control region which is active in liver (Kelsey et al., *Genes and Devel.* 7:161-171 (1987)), beta globin gene control region which is active in myeloid cells (Magram et al., *Nature* 515:338-340 (1985)); Kollias et al., *Cell* 5:89-94 (1986)), myelin basic protein gene control region which is active in oligodendrocyte cells of the brain (Readhead et al., *Cell* 15:703-712 (1987)), myosin light chain-2 gene control region which is active in skeletal muscle (Shani, *Nature* 514:283-286 (1985)), and gonadotrophic releasing hormone gene control region which is active in gonadotrophs of the hypothalamus (Mason et al., *Science* 254: 1372-1378 (1986)).

In addition to the promoter, the expression vector typically contains a transcription unit or expression cassette that contains all the additional elements required for the expression of the antibody, or portion thereof, in host cells. A typical expression cassette contains a promoter operably linked to the nucleic acid sequence encoding the antibody chain and signals required for efficient polyadenylation of the transcript, ribosome binding sites and translation termination. Additional elements of the cassette can include enhancers. In addition, the cassette typically contains a transcription termination region downstream of the structural gene to provide for efficient termination. The termination region can be obtained from the same gene as the promoter sequence or can be obtained from different genes.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a germline antibody chain under the direction of the polyhedron promoter or other strong baculovirus promoter.

Any methods known to those of skill in the art for the insertion of DNA fragments into a vector can be used to construct expression vectors containing a nucleic acid encoding any of the polypeptides provided herein. These methods can include in vitro recombinant DNA and synthetic techniques and in vivo recombinants (genetic recombination). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized nucleic acids encoding restriction endonuclease recognition sequences.

Exemplary plasmid vectors useful to produce the polypeptides provided herein contain a strong promoter, such as the HCMV immediate early enhancer/promoter or the MHC class I promoter, an intron to enhance processing of the transcript, such as the HCMV immediate early gene intron A, and a polyadenylation (poly A) signal, such as the late SV40 polyA signal.

Genetic modification of engineered immune cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the tumor antigen-targeted CAR and the SIRPα polypeptide can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide tumor antigen-targeted CAR and the SIRPα polypeptide expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. *Mol. Cell. Biol.* 5:431-437 (1985)); PA317 (Miller, et al. *Mol. Cell. Biol.* 6:2895-2902 (1986)); and CRIP (Danos, et al. *Proc. Natl. Acad. Sci. USA* 85:6460-6464 (1988)). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. *Blood* 80: 1418-1422(1992), or culturing with viral supernatant alone or concentrated vector stocks with or without appropriate growth factors and polycations, e.g., by the method of Xu, et al. *Exp. Hemat.* 22:223-230 (1994); and Hughes, et al. *J. Clin. Invest.* 89: 1817 (1992).

Transducing viral vectors can be used to express a co-stimulatory ligand and/or secretes a cytokine (e.g., 4-1BBL and/or IL-12) in an engineered immune cell. Preferably, the chosen vector exhibits high efficiency of infection and stable integration and expression (see, e.g., Cayouette et al., *Human Gene Therapy* 8:423-430 (1997); Kido et al., *Current Eye Research* 15:833-844 (1996); Bloomer et al., *Journal of Virology* 71:6641-6649, 1997; Naldini et al., *Science* 272:263 267 (1996); and Miyoshi et al., *Proc. Natl. Acad. Sci. U.S.A.* 94: 10319, (1997)). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* 15-14, (1990); *Friedman, Science* 244: 1275-1281 (1989); Eglitis et al., *BioTechniques* 6:608-614, (1988); Tolstoshev et al., *Current Opinion in Biotechnology* 1:55-61(1990); Sharp, *The Lancet* 337: 1277-1278 (1991); Cornetta et al., *Nucleic Acid Research and Molecular Biology* 36:311-322 (1987); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med* 323:370 (1990); Anderson et al., U.S. Pat. No. 5,399,346).

In certain non-limiting embodiments, the vector expressing a presently disclosed tumor antigen-targeted CAR is a retroviral vector, e.g., an oncoretroviral vector.

Non-viral approaches can also be employed for the expression of a protein in cell. For example, a nucleic acid molecule can be introduced into a cell by administering the nucleic acid in the presence of lipofection (Feigner et al., *Proc. Nat'l. Acad. Sci. U.S.A.* 84:7413, (1987); Ono et al., *Neuroscience Letters* 17:259 (1990); Brigham et al., *Am. J. Med. Sci.* 298:278, (1989); Staubinger et al., *Methods in Enzymology* 101:512 (1983)), asialoorosomucoid-polylysine conjugation (Wu et al., *Journal of Biological Chemistry* 263 14621 (1988); Wu et al., *Journal of Biological Chemistry* 264: 16985 (1989)), or by micro-injection under surgical conditions (Wolff et al., *Science* 247: 1465 (1990)). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Polypeptides and Analogs and Polynucleotides

Also included in the presently disclosed subject matter are extracellular antigen-binding domains that specifically binds to a tumor antigen (e.g., human tumor antigen) (e.g., an scFv (e.g., a human scFv), a Fab, or a $(Fab)_2$), CD3ζ, CD8, CD28, etc. polypeptides or fragments thereof, and polynucleotides encoding thereof that are modified in ways that enhance their anti-tumor activity when expressed in an engineered immune cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%), about 98%, about 99% or more identity or homology with all or part of a naturally-occurring amino, acid sequence of the presently disclosed subject matter. The length of sequence comparison is at least about 5, about 10, about 15, about 20, about 25, about 50, about 75, about 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethyl sulfate or by site-specific mutagenesis as described in Sambrook, Fritsch and Maniatis, Molecular Cloning: A Laboratory Manual (2nd ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least about 5, about 10, about 13, or about 15 amino acids. In some embodiments, a fragment is at least about 20 contiguous amino acids, at least about 30 contiguous amino acids, or at least about 50 contiguous amino acids. In some embodiments, a fragment is at least about 60 to about 80, about 100, about 200, about 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the antineoplastic activity of the original polypeptide when expressed in an engineered immune cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to an antigen (e.g., a an antigen expressed by normal healthy cells, an extracellular antigen, or a tumor antigen (e.g., human tumor antigen)) (e.g., an scFv (e.g., a human scFv), a Fab, or a $(Fab)_2$), CD3, CD8, CD28) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

Administration

Engineered immune cells expressing the tumor antigen-targeted CAR and a SIRPα polypeptide of the presently disclosed subject matter can be provided systemically or directly to a subject for treating or preventing a neoplasia. In certain embodiments, engineered immune cells are directly injected into an organ of interest (e.g., an organ affected by a neoplasia). Alternatively, or additionally, the engineered immune cells are provided indirectly to the organ of interest, for example, by administration into the circulatory system (e.g., the tumor vasculature) or into the solid tumor. Expansion and differentiation agents can be provided prior to, during or after administration of cells and compositions to increase production of T cells in vitro or in vivo.

Engineered immune cells of the presently disclosed subject matter can be administered in any physiologically acceptable vehicle, systemically or regionally, normally intravascularly, intraperitoneally, intrathecally, or intrapleurally, although they may also be introduced into bone or other convenient site where the cells may find an appropriate site for regeneration and differentiation (e.g., thymus). In certain embodiments, at least $1\times10^5$ cells can be administered, eventually reaching $1\times10^{10}$ or more. In certain embodiments, at least $1\times10^6$ cells can be administered. A cell population comprising engineered immune cells can comprise a purified population of cells. Those skilled in the art can readily determine the percentage of engineered immune cells in a cell population using various well-known methods, such as fluorescence activated cell sorting (FACS). The ranges of purity in cell populations comprising engineered immune cells can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The engineered immune cells can be introduced by injection, catheter, or the like. If desired, factors can also be included, including, but not limited to, interleukins, e.g., IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

In certain embodiments, compositions of the presently disclosed subject matter comprise pharmaceutical compositions comprising engineered immune cells expressing a tumor antigen-targeted CAR and a SIRPα polypeptide with a pharmaceutically acceptable carrier. Administration can be autologous or non-autologous. For example, engineered immune cells expressing a tumor antigen-targeted CAR and a SIRPα polypeptide and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising engineered immune cells expressing a tumor antigen-targeted CAR), it can be formulated in a unit dosage injectable form (solution, suspension, emulsion).

Formulations

Engineered immune cells expressing a tumor antigen-targeted CAR and SIRPα polypeptide and compositions comprising thereof can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter, e.g., a composition comprising engineered immune cells, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the engineered immune cells of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the engineered immune cells as described in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the engineered immune cells of the presently disclosed subject matter is the quantity of cells necessary to achieve an optimal effect. The quantity of cells to be administered will vary for the subject being treated. In certain embodiments, from about $10^2$ to about $10^{12}$, from about $10^3$ to about $10^{11}$, from about $10^4$ to about $10^{10}$, from about $10^5$ to about $10^9$, or from about $10^6$ to about $10^8$ engineered immune cells of the presently disclosed subject matter are administered to a subject. More effective cells may be administered in even smaller numbers. In some embodiments, at least about $1\times10^8$, about $2\times10^8$, about $3\times10^8$, about $4\times10^8$, about $5\times10^8$, about $1\times10^9$, about $5\times10^9$, about $1\times10^{10}$, about $5\times10^{10}$, about $1\times10^{11}$, about $5\times10^{11}$, about $1\times10^{12}$ or more engineered immune cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art. Generally, antibodies are administered at doses that are nontoxic or tolerable to the patient.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation Methods for Therapy For treatment, the amount of the engineered immune cells provided herein administered is an amount effective in producing the desired effect, for example, treatment of a cancer or one or more symptoms of a cancer. An effective amount can be provided in one or a series of administrations of the engineered immune cells provided herein. An effective amount can be provided in a bolus or by continuous perfusion. For adoptive immunotherapy using antigen-specific T cells, cell doses in the range of about $10^6$ to about $10^{10}$ are typically infused. Co-expression of the SIRPα polypeptide as disclosed herein, may permit lower doses of the engineered immune cells to be administered, e.g., about $10^4$ to about $10^8$. Upon administration of the engineered immune cells into the subject, the engineered immune cells are induced that are specifically directed against one tumor antigen. "Induction" of T cells can include inactivation of antigen-specific T cells such as by deletion or anergy. Inactivation is particularly useful to establish or reestablish tolerance such as in autoimmune disorders. The engineered immune cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the engineered immune cells and the compositions comprising thereof are intravenously administered to the subject in need. Methods for administering cells for adoptive cell therapies, including, for example, donor lymphocyte infusion and CAR T cell therapies, and regimens for administration are known in the art and can be employed for administration of the engineered immune cells provided herein.

The presently disclosed subject matter provides various methods of using the engineered immune cells (e.g., T cells) provided herein, expressing a tumor antigen-targeted receptor (e.g., a CAR) and a SIRPα polypeptide. For example, the presently disclosed subject matter provides methods of reducing tumor burden in a subject. In one non-limiting example, the method of reducing tumor burden comprises administering an effective amount of the presently disclosed engineered immune cells to the subject and administering a suitable antibody targeted to the tumor, thereby inducing tumor cell death in the subject. In some embodiments, the engineered immune cells and the antibody are administered simultaneously. In some embodiments, the engineered immune cells and the antibody are administered at different times. For example, in some embodiments, the engineered immune cells are administered and then the antibody is administered. In some embodiments, the antibody is administered 1 hour, 2 hours, 3 hours, 4 hours, 5 hours, 6 hours, 7 hours, 8 hours, 9 hours, 10 hours, 11 hours, 12 hours, 18 hours, 24 hours, 30 hours, 26 hours, 48 hours or weeks (e.g., 1 week, 2 weeks, 3 weeks, or 4 weeks) to months (e.g., one month, two months, three months, four months, five months, six months, seven months, eight months, nine months, ten months, eleven months, or 12 months) after the administration of the engineered immune cells. Without wishing to be bound by theory, this is because the cells persist in the patient for many months and the antibody can persist for several days to weeks. In some embodiments, the antibody is administered and then the engineered immune cells are administered. In some embodiments, the antibody is administered 1 hour, 2 hours, 3 hours, 4 hours, 5 hours, 6 hours, 7 hours, 8 hours, 9 hours, 10 hours, 11 hours, 12 hours, 18 hours, 24 hours, 30 hours, 26 hours, 48 hours or days (e.g., 1 day, 2 days, 3 days, 4 days, 5 days, 6 days, or 7 days) or weeks (e.g., 1 week, 2 weeks, 3 weeks, or 4 weeks) before the administration of the engineered immune cells.

The methods provided herein allow for modular use of a wide range of CAR and tumor-reactive antibody combinations depending on the desired application. The tumor-reactive antibodies can synergize with the enhanced macrophage-mediated ADCP of cancer cells and/or with direct immune-based cytotoxic effects of the engineered immune cells, e.g., orexigenic CAR T cells. In some embodiments, the CAR and the tumor-reactive antibody target distinct tumor antigens. Without wishing to be bound by theory, this will decrease the risk of antigen-negative relapse by increasing the likelihood of killing multiple tumor populations to yield a more complete antitumor response. The engineered immune cells described herein can be employed in combination with a wide variety of tumor-reactive antibodies. Tumor-reactive antibodies are known in art. Exemplary tumor-reactive antibodies include, but are not limited to, antibodies targeted to Her2, EGFR, PSMA, CD20, CD33, CD38, or WT1. In some embodiments, the tumor-reactive antibody is trastuzumab, cetuximab, ESK1, rituximab, daratumumab, or lintuzumab. In some embodiments, CAR targets MUC16 and the tumor-reactive monoclonal antibody specifically binds to EGFR or Her2. In some embodiments, the CAR targets MUC16 and the tumor-reactive monoclonal antibody specifically binds to EGFR or Her2. In some embodiments, the CAR targets mesothelin and the tumor-reactive monoclonal antibody specifically binds to EGFR. In some embodiments, the CAR targets WT1 and the tumor-reactive monoclonal antibody specifically binds to CD33. In some embodiments, the CAR targets PSCA and the tumor-reactive monoclonal antibody specifically binds to PSMA. In some embodiments, the CAR targets BCMA and the tumor-reactive monoclonal antibody specifically binds to CD38.

The presently disclosed engineered immune cells either alone or in combination with an antibody targeted to the tumor can reduce the number of tumor cells, reduce tumor size, and/or eradicate the tumor in the subject. In certain embodiments, the method of reducing tumor burden comprises administering an effective amount of engineered immune cells to the subject, thereby inducing tumor cell death in the subject. Non-limiting examples of suitable tumors include adrenal cancers, bladder cancers, blood cancers, bone cancers, brain cancers, breast cancers including triple negative breast cancer, carcinoma, cervical cancers, colon cancers, colorectal cancers, corpus uterine cancers, ear, nose and throat (ENT) cancers, endometrial cancers, esophageal cancers, gastrointestinal cancers including gastric cancer, head and neck cancers, Hodgkin's disease, intestinal cancers, kidney cancers, larynx cancers, acute and chronic leukemias including acute myeloid leukemia, liver cancers, lymph node cancers, lymphomas, lung cancers including non-small cell lung cancer, melanomas, mesothelioma, myelomas including multiple myeloma, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof. In some embodiments, the cancer is a relapsed or refractory cancer. In some embodiments, the cancer is resistant to one or more cancer therapies, e.g., one or more chemotherapeutic drugs.

The presently disclosed subject matter also provides methods of increasing or lengthening survival of a subject having a neoplasia (e.g., a tumor). In one non-limiting example, the method of increasing or lengthening survival of a subject having neoplasia (e.g., a tumor) comprises administering an effective amount of the presently disclosed engineered immune cell to the subject, thereby increasing or lengthening survival of the subject. The presently disclosed subject matter further provides methods for treating or preventing a neoplasia (e.g., a tumor) in a subject, comprising administering the presently disclosed engineered immune cells to the subject.

Cancers whose growth may be inhibited using the engineered immune cells of the presently disclosed subject matter comprise cancers typically responsive to immunotherapy. Non-limiting examples of cancers for treatment include multiple myeloma, neuroblastoma, glioma, acute myeloid leukemia, breast cancer, colon cancer, esophageal cancer, gastric cancer, non-small cell lung cancer, ovarian cancer, pancreatic cancer, prostate cancer, thyroid cancer, small cell lung cancer, and NK cell lymphoma. In certain embodiments, the cancer is multiple myeloma. In certain embodiments, the cancer is triple negative breast cancer or ovarian cancer. In some embodiments, the cancer is prostate cancer. In some embodiments, the cancer is acute myeloid leukemia. In some embodiments, the cancer is ovarian cancer, non-small cell lung cancer, esophageal cancer, gastric cancer, colorectal cancer, or triple negative breast cancer.

Additionally, the presently disclosed subject matter provides methods of increasing immune-activating cytokine production in response to a cancer cell in a subject. In one non-limiting example, the method comprises administering the presently disclosed engineered immune cell to the subject. The immune-activating cytokine can be granulocyte macrophage colony stimulating factor (GM-CSF), IFNα, IFN-β, IFN-γ, TNF-α, IL-2, IL-3, IL-6, IL-1 1, IL-7, IL-12, IL-15, IL-21, interferon regulatory factor 7 (IRF7), and combinations thereof. In certain embodiments, the engineered immune cells including a tumor antigen-specific CAR of the presently disclosed subject matter increase the production of GM-CSF, IFN-γ, and/or TNF-α.

Suitable human subjects for therapy typically comprise two treatment groups that can be distinguished by clinical criteria. Subjects with "advanced disease" or "high tumor burden" are those who bear a clinically measurable tumor (e.g., multiple myeloma). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., multiple myeloma).

A second group of suitable subjects is known in the art as the "adjuvant group." These are individuals who have had a history of neoplasia (e.g., multiple myeloma), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor (e.g., multiple myeloma) has invaded neighboring tissues, or who show involvement of lymph nodes. Another group has a genetic predisposition to neoplasia (e.g., multiple myeloma) but has not yet evidenced clinical signs of neoplasia (e.g., multiple myeloma). For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

The subjects can have an advanced form of disease (e.g., multiple myeloma), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the tumor antigen-targeted CAR-expressing engineered immune cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvFID. Modification of the engineered immune cells can include engineering a suicide gene into the tumor antigen-targeted CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the C-terminus of the intracellular domain of the tumor antigen-targeted CAR. The suicide gene can be included within the vector comprising nucleic acids encoding the presently disclosed tumor antigen-targeted CARs. The incorporation of a suicide gene into the a presently disclosed tumor antigen-targeted CAR gives an added level of safety with the ability to eliminate the majority of CAR T cells within a very short time period. A presently disclosed engineered immune cell (e.g., a T cell) incorporated with a suicide gene can be pre-emptively eliminated at a given time point post CAR T cell infusion, or eradicated at the earliest signs of toxicity.

Articles of Manufacture and Kits

The presently disclosed subject matter provides kits for the treatment or prevention of a neoplasia (e.g., solid tumor). In certain embodiments, the kit comprises a therapeutic or prophylactic composition containing an effective amount of an engineered immune cell comprising a tumor antigen-targeted receptor (e.g., a CAR) and SIRPα polypeptide in unit dosage form. In particular embodiments, the cells further expresses at least one co-stimulatory ligand. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the engineered immune cell can be provided together with instructions for administering the engineered immune cell to a subject having or at risk of developing a neoplasia (e.g., solid tumor). The instructions will generally include information about the use of the composition for the treatment or prevention of a neoplasia (e.g., solid tumor). In other embodiments, the instructions include at least one of the following: description of the therapeutic agent; dosage schedule and administration for treatment or prevention of a neoplasia (e.g., solid tumor) or symptoms thereof, precautions; warnings; indications; counter-indications; overdose information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1. CV1 is Secreted in an Active Form by Engineered Human Cells

To determine the feasibility of genetically encoding CV1 into CAR T cells for local secretion, whether CV1 could be encoded into a human cell and then secreted in an active form was first tested. HEK293T cells were used as a first model. The HEK293T cells were transduced with the gene for CV1, which was expressed, and secreted, as determined by PCR and western blot. Second, the effectiveness of the secreted cellular construct in vivo was tested.

Figure 2A:
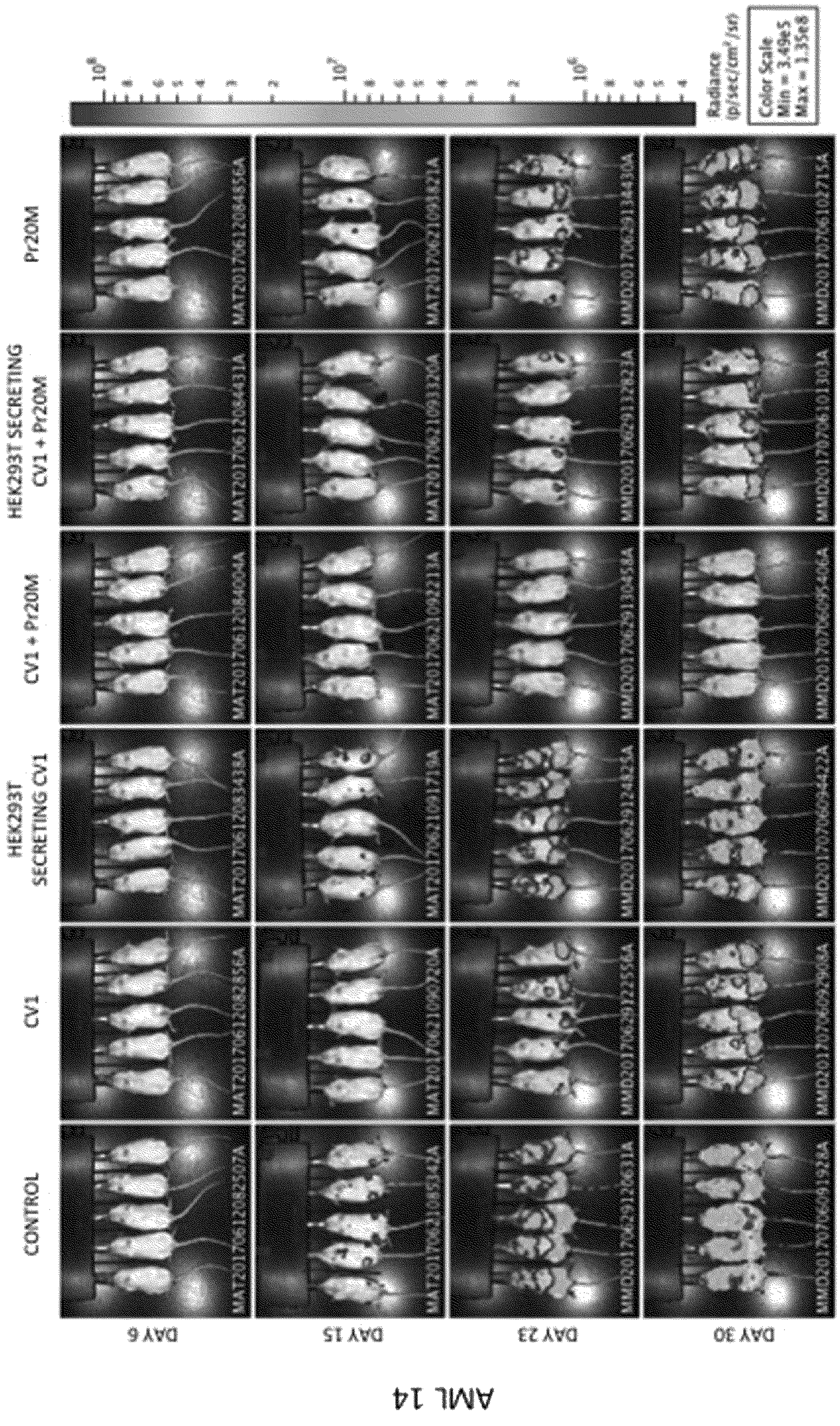
FIGS. 2A and 2B show that combination therapy with HEK-secreted CV1 and Pr20M has synergistic effects. Mice were engrafted via tail vein injection with 3 million cells/mouse of AML 14 transduced to express Luciferase-GFP and were randomized such that each group had equal mean engraftment and treated beginning day 6. The 6 treatment groups were: 1) Tumor only, 2) daily 100 μg CV1 IP alone, 3) single dose IP of HEK293T secreting CV1 alone, 4) daily 100 μg CV1 IP+BIW 50 μg Pr20M antibody IV, 5) single dose IP of HEK293T secreting CV1+50 μg BIW Pr20M antibody, 6) 50 μg BIW Pr20M antibody alone. Mice were injected with HEK293T secreting CV1 at 10 million cells/mouse on Day 6.
Figure 2B:
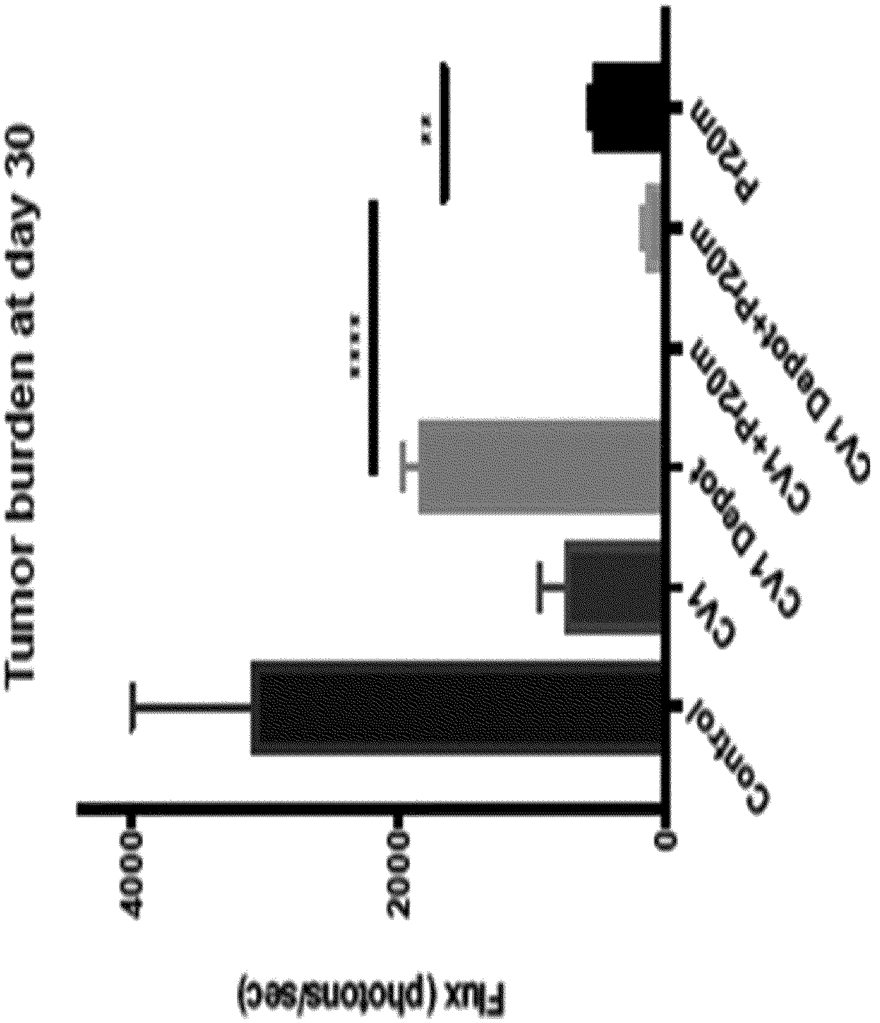

Mice were engrafted via tail vein injection with 3 million cells/mouse of AML 14 transduced to express Luciferase-GFP and were randomized such that each group had equal mean engraftment and treated beginning day 6. The 6 treatment groups were: 1) Tumor only, 2) daily 100 μg CV1 intraperitoneally (IP) alone, 3) single dose IP of HEK293T secreting CV1 alone, 4) daily 100 μg CV1 IP+BIW 50 μg Pr20M antibody IV, 5) single dose IP of HEK293T secreting CV1+50 μg BIW Pr20M antibody, 6) 50 μg BIW Pr20M antibody alone. Mice were injected with HEK293T secreting CV1 at 10 million cells/mouse on Day 6. FIG. 2A shows raw bioluminescent images on a standardized scale taken on Days 6, 15, 23, and 30. Tumor burden was quantified on Day 30 and FIG. 2B shows that HEK-secreted CV1 is functional and can potentiate mAb therapy.

Thus, remarkably, in mice, one injection of the CV1 secreting human cells IP was effective at activating macrophages to better kill human AML14 leukemia cells with an antibody (Pr20M) directed to those cells (FIG. 2) and combination therapy with HEK-secreted CV1 and Pr20M showed synergistic effects. Therefore, the proof of concept for in vivo use of a cellular CV1-secreting depot approach was validated.

Example 2. Construction of OrexiCAR T Cells Expressing a Chimeric Antigen Receptor in Combination with a Secretable CV1 Protein This Example describes the construction of a cell that expresses a CAR (e.g., with an antigen-binding domain specific for MUC16, WT1, or mesothelin). CAR T cells reactive with MUC16, WT1, mesothelin have been described (Brentjens et al., *Sci Transl Med* 5(177):177ra38 (2013); Pegram et al., *Leukemia* 29(2):415-22 (2015); Rafiq et al., *Leukemia* 31(8):1788-1797 (2017); Zeltsman et al., *Transl Res.* 187:1-10 (2017); Adusumilli et al., *Sci Transl Med* 6(261):261ra151 (2014); Koneru et al., *J Transl Med* 13:102 (2015); Chekmasova et al., *Clin Cancer Res.* 16(14):3594-606 (2010)). Following transduction, CAR expression is verified by flow cytometry, staining for the scFv incorporated into the CAR T cell, and western blot. To generate the CV1-secreting OrexiCAR variants of these CAR T cells, CV1 is cloned and inserted downstream of the CD3-ζ chain, separated by a self-cleaving P2A peptide sequence which will generate an independent CV1 protein. The CAR-CV1 OrexiCAR construct is then transferred into human T cells using standard retroviral transduction methods. Specific T cell cytotoxicity is measured using a standard chromium release assay against a panel of antigen positive or negative tumor cells. Specific cytokine secretion is measured by collecting supernatant from 24 hr co-cultures of OrexiCAR T cells and tumor cells, using Luminex technology. The ability of the CD3-4-1BB CAR to stimulate T cell proliferation is analyzed by co-culturing transduced T cells with antigen+ or − tumor cells and monitoring T cell expansion with flow cytometry using enumeration beads. T cells transduced to express a CAR targeted to an irrelevant antigen will be used as a control. Whether there is additive or synergistic killing with an antibody action plus the CAR T cytotoxicity vs the CAR T alone and with human macrophages or soluble CV1 is also tested.

Once each of the OrexiCAR T cell formats is produced, several OrexiCAR T cells of each OrexiCAR T cell format are produced from different donors and their activity against cell lines, both positive and negative, fresh cancer cells, and normal PBMCs, is tested using previously published methods (Brentjens et al., *Sci Transl Med* 5(177):177ra38 (2013); Pegram et al., *Leukemia* 29(2):415-22 (2015); Rafiq et al., *Leukemia* 31(8):1788-1797 (2017); Zeltsman et al., *Transl Res.* 187:1-10 (2017); Adusumilli et al., *Sci Transl Med* 6(261):261ra151 (2014); Koneru et al., *J Transl Med* 13:102 (2015); Chekmasova et al., *Clin Cancer Res.* 16(14):3594-606 (2010)). The CAR is employed for targeting the cancer cells. The OrexiCAR T cell format also secretes the CV1 to provide a larger killing radius of unengaged and antigen-negative cancers and activates both macrophage phagocytosis alone and ADCP (FIG. 1).

Example 3. Efficacy of OrexiCAR T Cells in Mice in Combination with Antibody Therapy The ability of OrexiCAR T cells (e.g., OrexiCAR T cells expressing CARs with an antigen-binding domain specific for MUC16, WT1, or mesothelin) to eradicate tumors in vivo is assessed using preclinical xenogeneic murine models in accordance with IACUC protocols. SCID-Beige or NSG mice are inoculated with tumor cells modified to express luciferase. Mice are subsequently treated with a systemic infusion of OrexiCAR or control CAR cells. The antibodies are matched for the CAR target and include, e.g., human mAbs to Her2, CD33, EGFR, and WT1, all of which are available and active in models; negative control antibodies are used as well. Dose response to numbers of CARs and antibodies is determined to find the optimal number of cells to infuse and the concentration of antibody. Macrophages in the mice are sufficient (Mathias et al., *Leukemia* 31(10): 2254-2257 (2017)). Disease progression is monitored both clinically and with bioluminescent imaging. Persistence of OrexiCAR T cells is determined via flow cytometry. OrexiCAR function over time is determined by detection of cytokines in the serum of treated mice using Luminex technology. Antibody and CV1 levels in the serum, target and off target normal tissues are measured by ELISA.

Healthy and xenografted mice injected with the OrexiCARs are followed daily and scored for 5 clinical signs of toxicity (per IACUC protocols) and weekly for weight gain or loss. Peripheral blood cell counts are assessed in selected mice and bone marrow, spleen, kidney and liver pathology are analyzed at sacrifice. Rules for sacrificing moribund mice are in place in the IACUC protocols.

The OrexiCAR T cells are effective at activating macrophages to better kill cancer cells with an antibody directed to those cells (e.g., human mAbs to EGFR, Her2 and WT1).

Example 4. Construction of OrexiCAR T Cells Expressing a CD19 or MUC16 Chimeric Antigen Receptor and CV1

Mammalian optimized anti-CD19 and 4H11 (anti-MUC16) scFv sequences were used to generate CARs targeting CD19 and MUC16, respectively. The endoplasm reticulum (ER) signal sequence from CD8 was inserted upstream of the CAR's variable heavy and light chains for cell surface expression of the CAR. The 4-1BB costimulatory domain was utilized since it has been shown to increase CAR T cell persistence (Long et al., *Nat Med.* 21:581-590 (2015) and Brentjens et al., *Clin Cancer Res.* 13:5426-5435 (2007)). The CD3ζ signaling chain was cloned downstream of the costimulatory domain and all these components were inserted into the SFG retroviral vector to form a second generation CAR. The CV1 gene with an HA epitope tag was cloned immediately downstream of the CAR, separated by a P2A self-cleavage site to produce two independent proteins, the CAR and CV1 (FIG. 3).

Figure 4A:
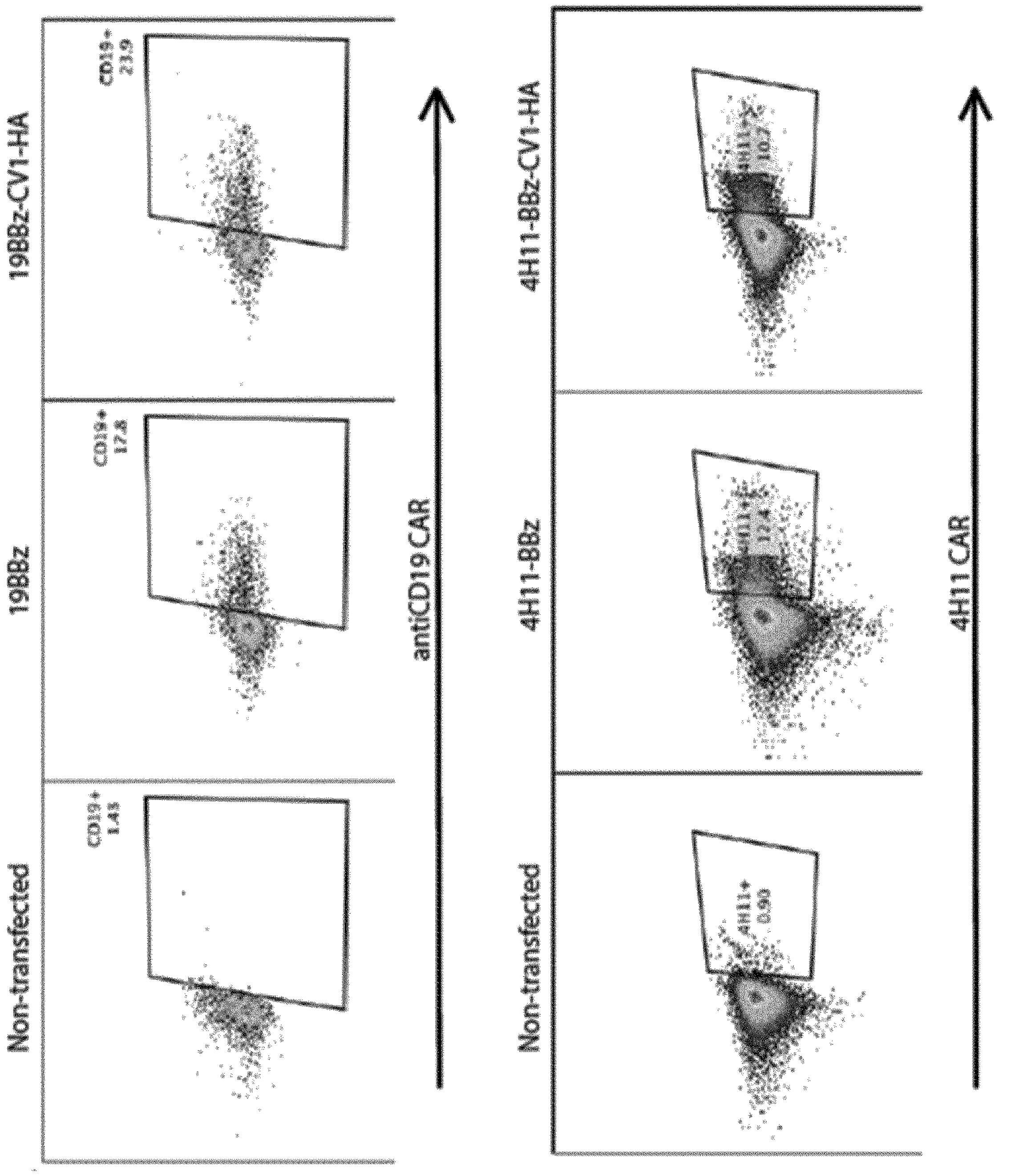
FIGS. 4A and 4B show, respectively, the expression of CAR and CV1 verified in HEK293 cells by flow cytometry and western blot. HEK293T cells were transfected with 4 g of the control CD19 and 4H11 CAR vectors or the OrexiCAR constructs described in FIG. 3. The cells show surface expression of the anti-CD19 and -MUC16 (4H11) scFv as verified by flow cytometry (FIG. 4A) and cell lysate and supernatant expression of CV1 as measured via western blot for the HA epitope tag (FIG. 4B).
Figure 4B:
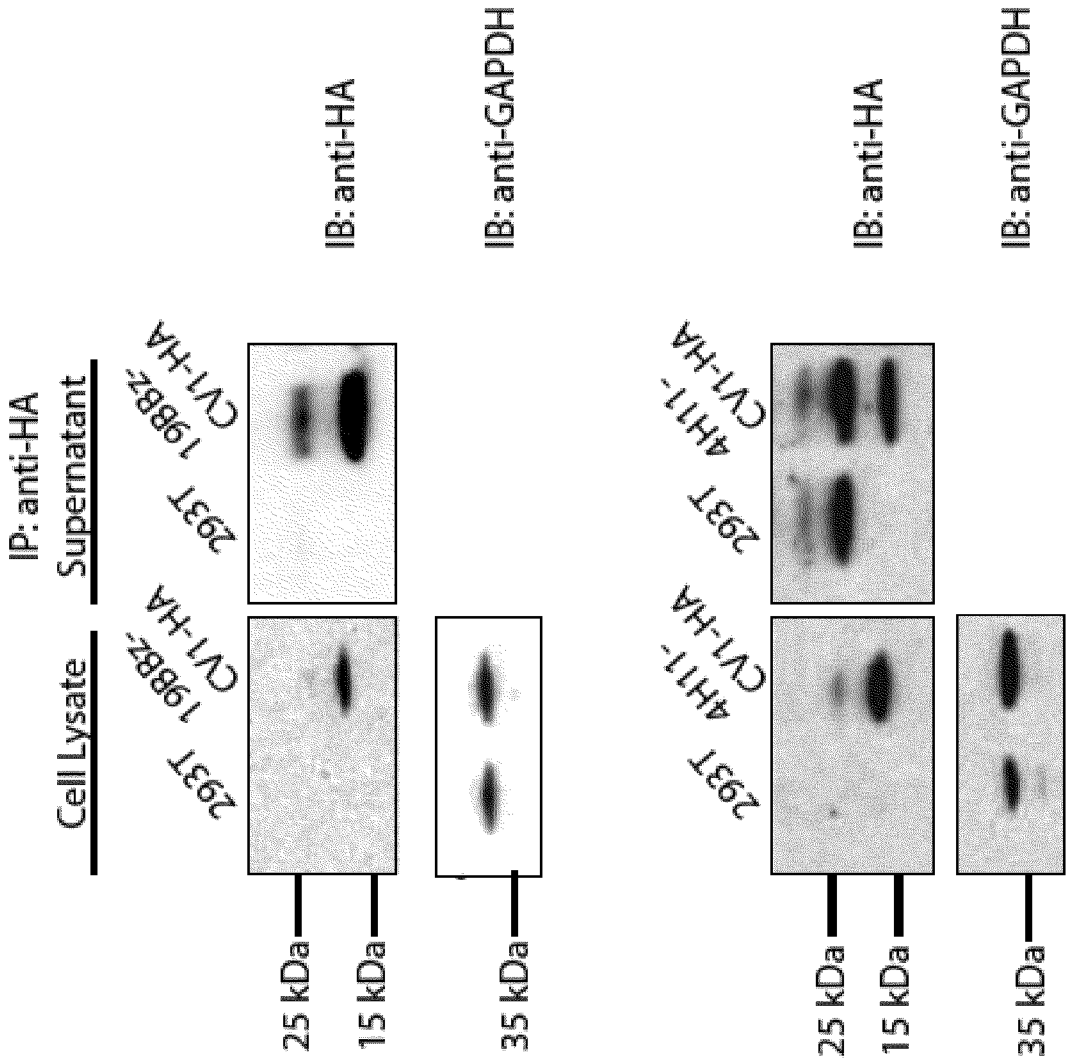

Both the CD19- and MUC16-targeted CARs were generated and verified for both the CAR and CV1 expression (FIG. 4). Transfected HEK293 Ts show the anti-CD19 and 4H11 scFvs on the cell surface by flow cytometry (FIG. 4A). CV1 was found in the cell lysate and secreted by HEK293T cells transfected with these vectors (FIG. 4B).

Figure 5A:
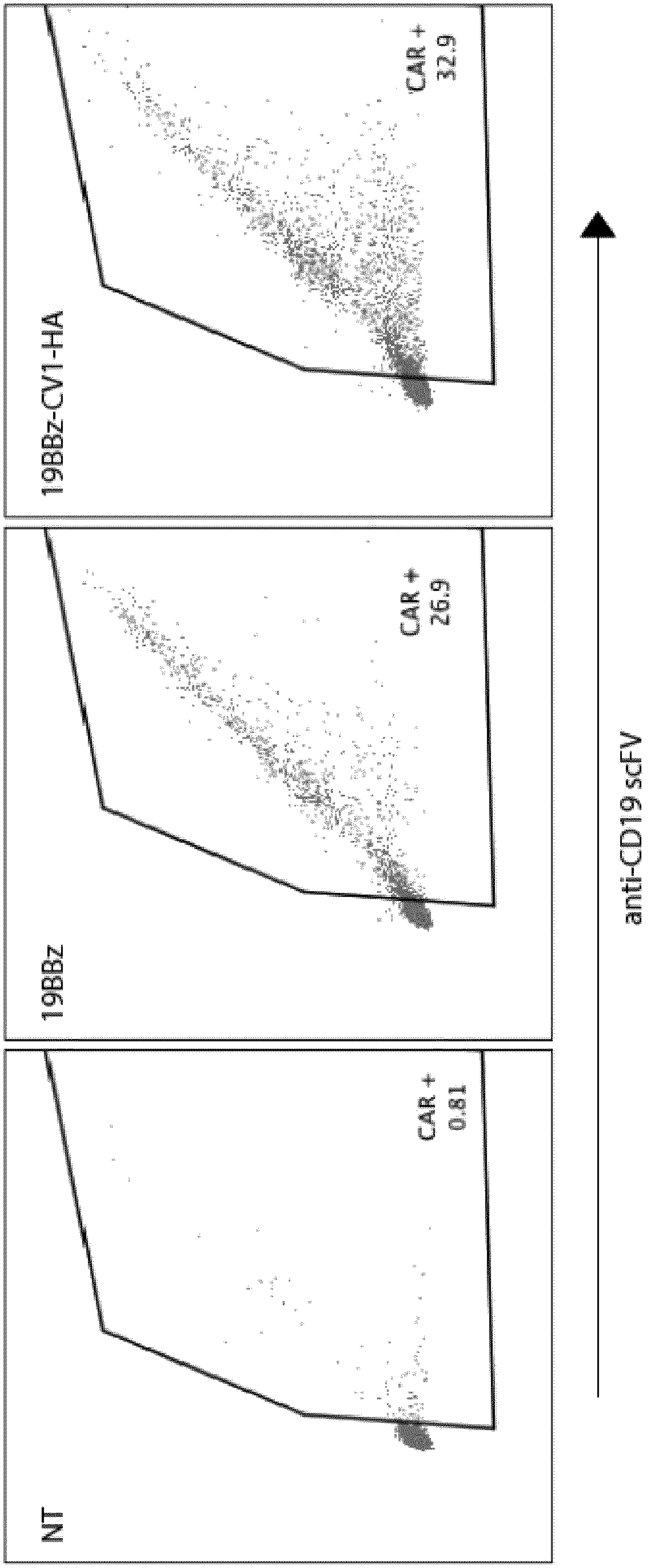
FIGS. 5A and 5B show, respectively, the expression of CAR and CV1 verified in primary human T cells transduced with WT and OrexiCAR vectors. Primary human T cells were isolated using Ficoll density gradient and were stimulated with PHA and IL2. T cells were transduced using virus produced form 293-Galv9 cells on Retronectin-coated plates. OrexiCAR transduced T cells show surface expression of the CAR by flow cytometry (FIG. 5A) and expression of CV1 in the cell supernatant by western blot (FIG. 5B).
Figure 6A:
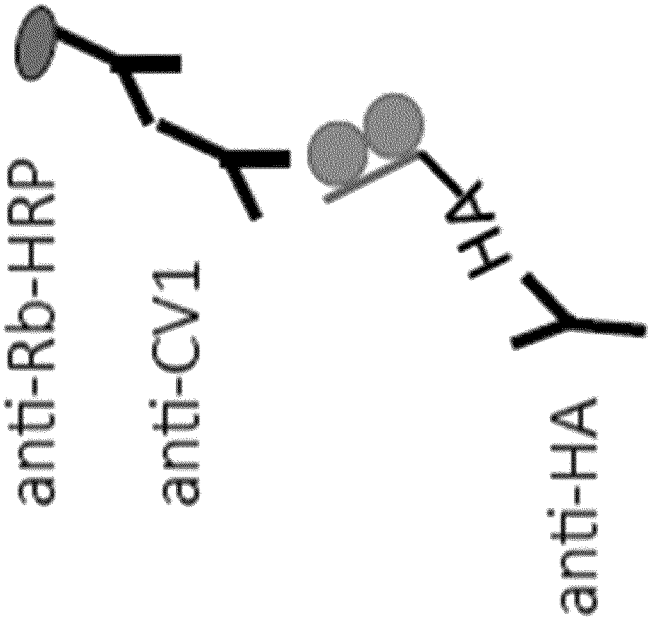
FIGS. 6A-6D show that antigen stimulation of OrexiCAR T cells leads to increased CV1 secretion. Primary human T cells were isolated and transduced with either WT or OrexiCAR vectors. Transduced T cells were subsequently co-cultured with antigen-negative or -positive cells at an E:T of 1:1. Supernatant was collected daily over a three day period and assayed for CV1 expression by a sandwich ELISA.
Figure 5B:
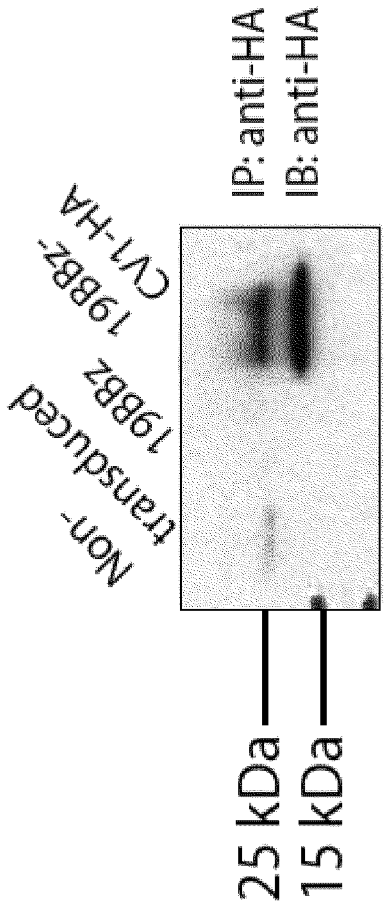

In addition, primary human T cells were transduced with the CD19 OrexiCAR vector. Primary human T cells were stimulated with PHA and IL2 and transduced using retrovirus produced from 293-Galv9 cells. Transduction efficiency was assessed via flow cytometry staining using anti-idiotype antibodies available in-house for anti-CD19. CV1 expression and secretion was verified by immunoblot for the HA epitope tag. CV1 concentrations were quantified using a sandwich enzyme linked immunosorbent assay (ELISA) with a manufactured CV1 antibody and HA antibody (FIG. 6A). The transduced primary human T cells show anti-CD19 scFv surface expression by flow cytometry and CV1 secretion by western blot (FIGS. 5A and 5B).

Figure 6B:
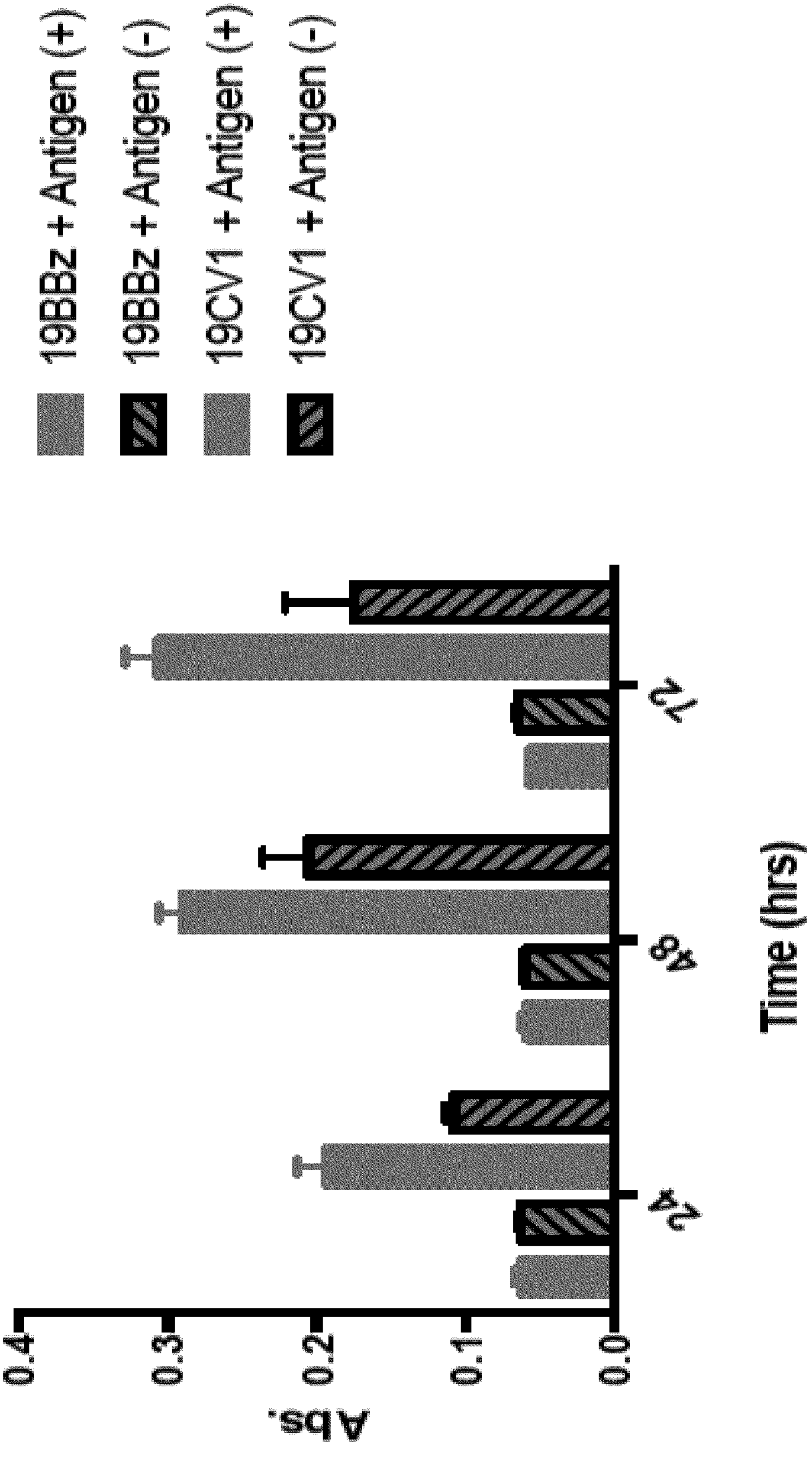
Figure 6C:
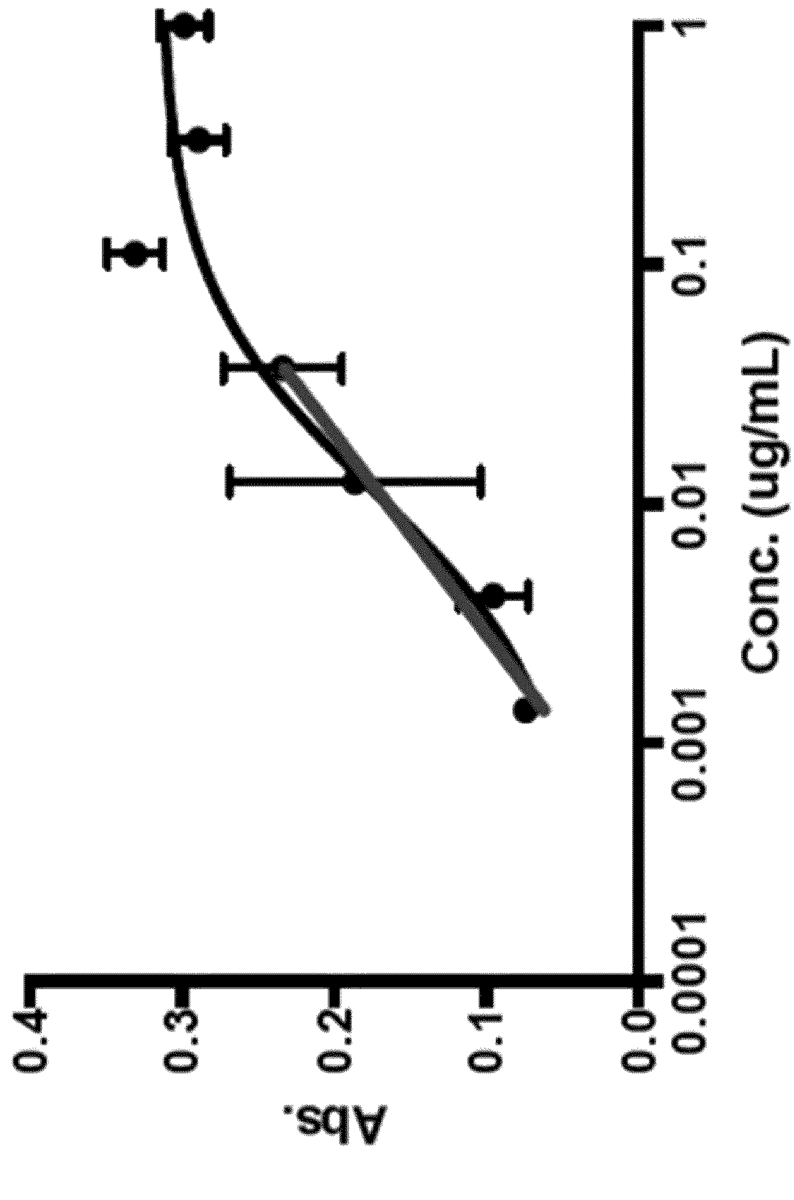
Figure 6D:
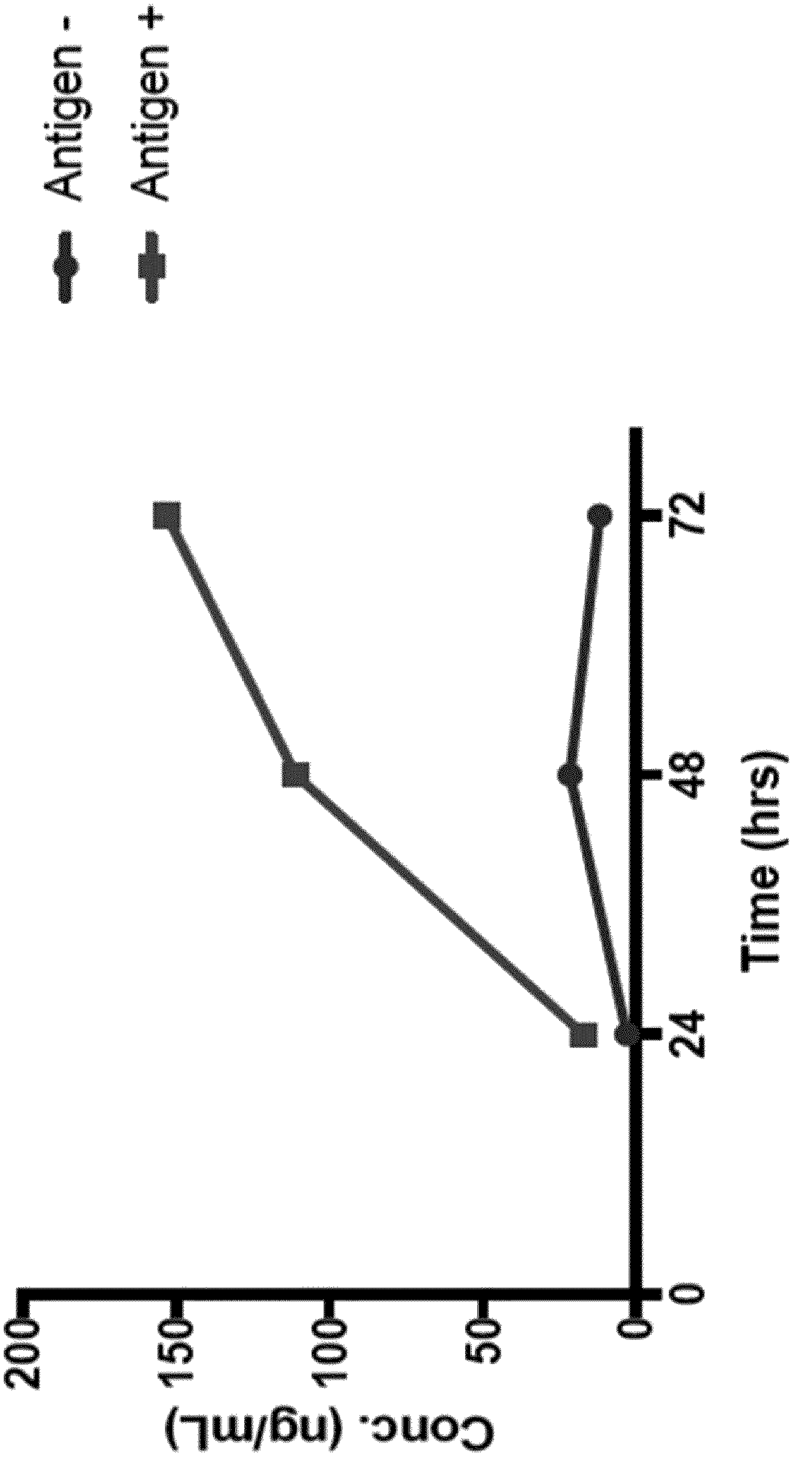

FIGS. 6A-6D show that antigen stimulation of OrexiCAR T cells leads to increased CV1 secretion. Primary human T cells were isolated and transduced with either WT or CD19 OrexiCAR vectors. Transduced T cells were subsequently co-cultured with antigen-negative or -positive cells at an E:T of 1:1. Supernatant was collected daily over a three day period and assayed for CV1 expression by a sandwich ELISA. FIG. 6A shows the schematic for the sandwich ELISA. Secreted CV1 was quantified by absorbance at 450 nm using TMB substrate and sulfuric acid to quench the reaction and the results are shown in FIG. 6B. Concentration of CV1 was analyzed by interpolation of a standard curve, made using recombinant CV1-HA. The results are shown in FIG. 6C. FIG. 6D shows that antigen stimulation of the CAR leads to a 10-fold increase in OrexiCAR-secreted CV1.

Example 5. Validation of OrexiCAR Functionality In Vitro

Transduced OrexiCAR T cells (e.g., OrexiCAR T cells expressing CARs with an antigen-binding domain specific for CD19, MUC16, WT1, or mesothelin) are compared to non-CV1 secreting (WT) CAR T cells to assess activation and cytolytic ability. T cells (non-transduced, CAR, and OrexiCAR) will be co-cultured with antigen-negative and -positive cells. T cell proliferation is quantified by cell counting using trypan blue exclusion assay. T cell activation is assessed by staining for CD69, an early lymphoid activation marker, and by cytokine secretion (Simms and Ellis, *Clin Daign Lab Immunol.* 3:301-304 (1996)). Luminex technology is used to assess cytokines secretion including interferon gamma (INFγ) and interleukin 2 (IL2). Cytolytic ability is measured using a luciferase based assay, where CARs are co-cultured with Luc+ target cells and cell lysis is measured as a function of luciferase activity (Fu et al., *PLoS One* 5:3-8 (2010)).

To assess the pro-phagocytic ability of OrexiCARs, the THP-1 monocyte cell line is differentiated into macrophages by stimulation with PMA for use in a flow-based phagocytosis assay. Differentiated macrophages and GFP+ target cells are co-cultured at an E:T of 1:2 (Weiskopf et al., *Science* 341:1-13 (2014)). Supernatant from stimulated OrexiCARs, or control CAR T cells, is added to the co-culture along with varying antibody concentrations (e.g., anti-CD20 antibody, anti-Her2 antibody, anti-CD33 antibody, or anti-EGFR antibody for CD19 OrexiCAR, MUC16 OrexiCAR, WT1 OrexiCAR, or mesothelin OrexiCAR respectively). Phagocytosis will be measured by the percent of GFP+ macrophages, indicating engulfment of target cells.

CV1 secretion does not hinder the CAR T cells cytolytic capability. Secreted CV1 is functionally active, as demonstrated in vivo in a proof-of concept model, using HEK293 Ts secreting CV1 in an AML mouse model (FIG. 2). In vitro, OrexiCAR-secreted CV1 increases phagocytosis, detected as an increase in GFP+ macrophages, in combination with antibodies targeted to cancer cells (e.g., anti-CD20 antibody, anti-Her2 antibody, anti-CD33 antibody, or anti-EGFR antibody for CD19 OrexiCAR, MUC16 OrexiCAR, WT1 OrexiCAR, or mesothelin OrexiCAR respectively).

Example 6. CD19 OrexiCAR T Cells Retain Cytotoxic Function In Vitro

Figure 7:
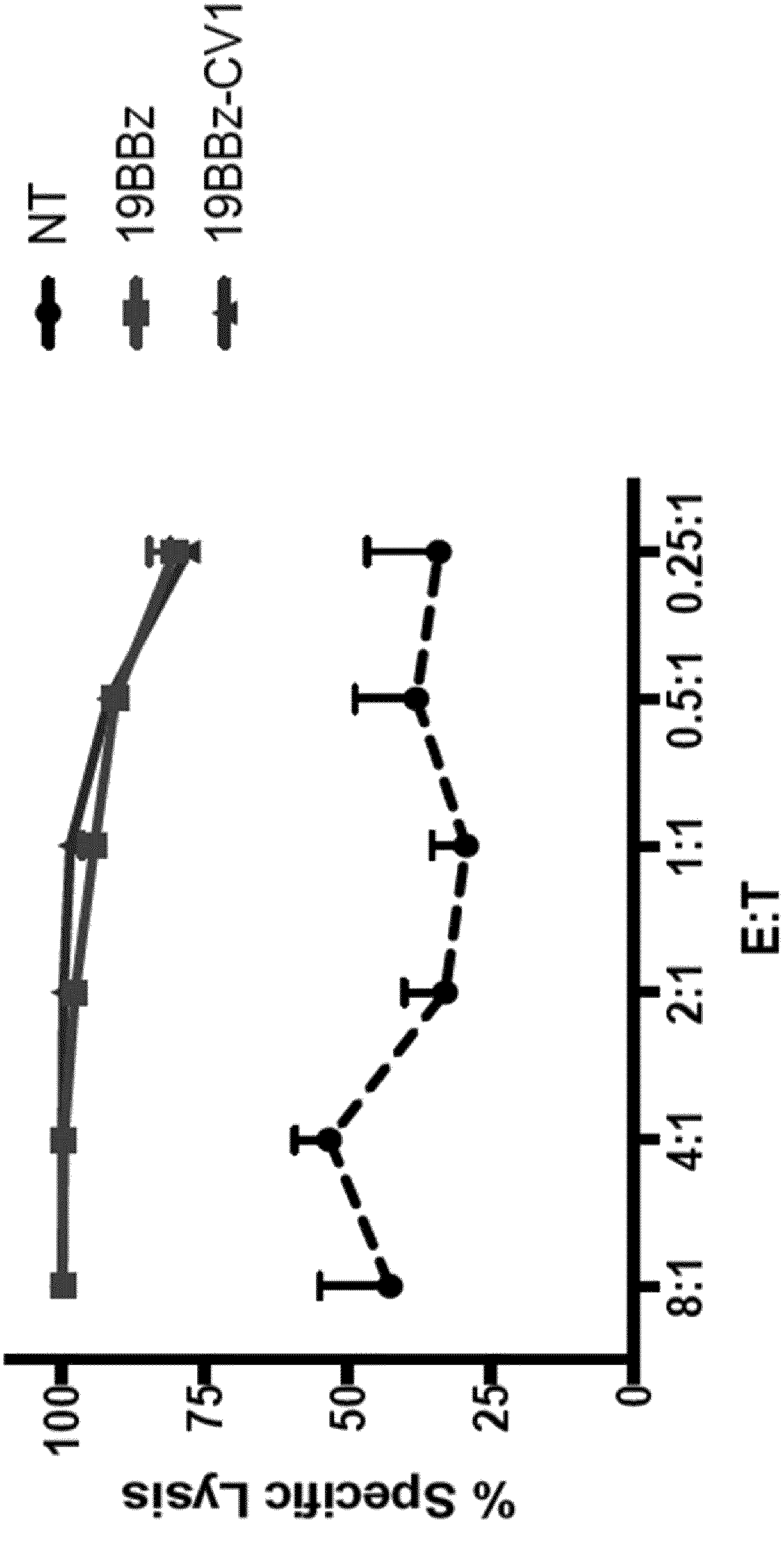
FIG. 7 shows that OrexiCAR T cells retain cytotoxic function in vitro. Primary human T cells were isolated and transduced with the WT CAR vector (19BBz) or OrexiCAR vector (19BBz-CV1). Transduced and non-transduced (NT) T cells were co-cultured with luciferase expressing CD19+ target cells at varying E:T ratios. After 24 hrs, specific lysis was quantified as a measure of luminescence and was normalized to untreated target cells. OrexiCAR T cells showed equivalent levels of specific lysis as WT CARs, suggesting CV1 secretion does not hinder CAR-mediated cytolysis.

Primary human T cells were isolated and transduced with the WT CAR vector (19BBz) or OrexiCAR vector (19BBz-CV1). Transduced and non-transduced (NT) T cells were co-cultured with luciferase expressing CD19+ target cells at varying E:T ratios. After 24 hrs, specific lysis was quantified as a measure of luminescence and was normalized to untreated target cells. OrexiCAR T cells showed equivalent levels of specific lysis as WT CARs, suggesting CV1 secretion does not hinder CAR-mediated cytolysis (FIG. 7).

Example 7. Anti-Tumor Effects of OrexiCAR T Cells and mAb Combination In Vivo NSG mice were engrafted IV with tumor cells engineered to express firefly luciferase. Raji B cell lymphoma was used as the established tumor model. The SIRPα allele in NSG mice binds to the human CD47, allowing for the use of CV1 in xenograft models (Weiskopf et al., *Science* 341:1-13 (2014); Mathias et al., *Leukemia* 31(10):2254-2257 (2017); Chao et al., *Cell* 142:699-713 (2010); Yamauchi et al., *Blood* 121:1316-1325 (2013)).

Tumor growth was quantified by bioluminescent imaging (BLI). Primary human T cells were transduced with CD19 OrexiCAR and control CD19 CAR vectors using methods described above. All CAR T cells were given with and without rituximab administration. After tumor engraftment in IP cavity, 1 million T cells were administered with a single injected dose IP and rituximab was administered at 200 μg thrice weekly (TIW) for 5 doses.

Figure 8:
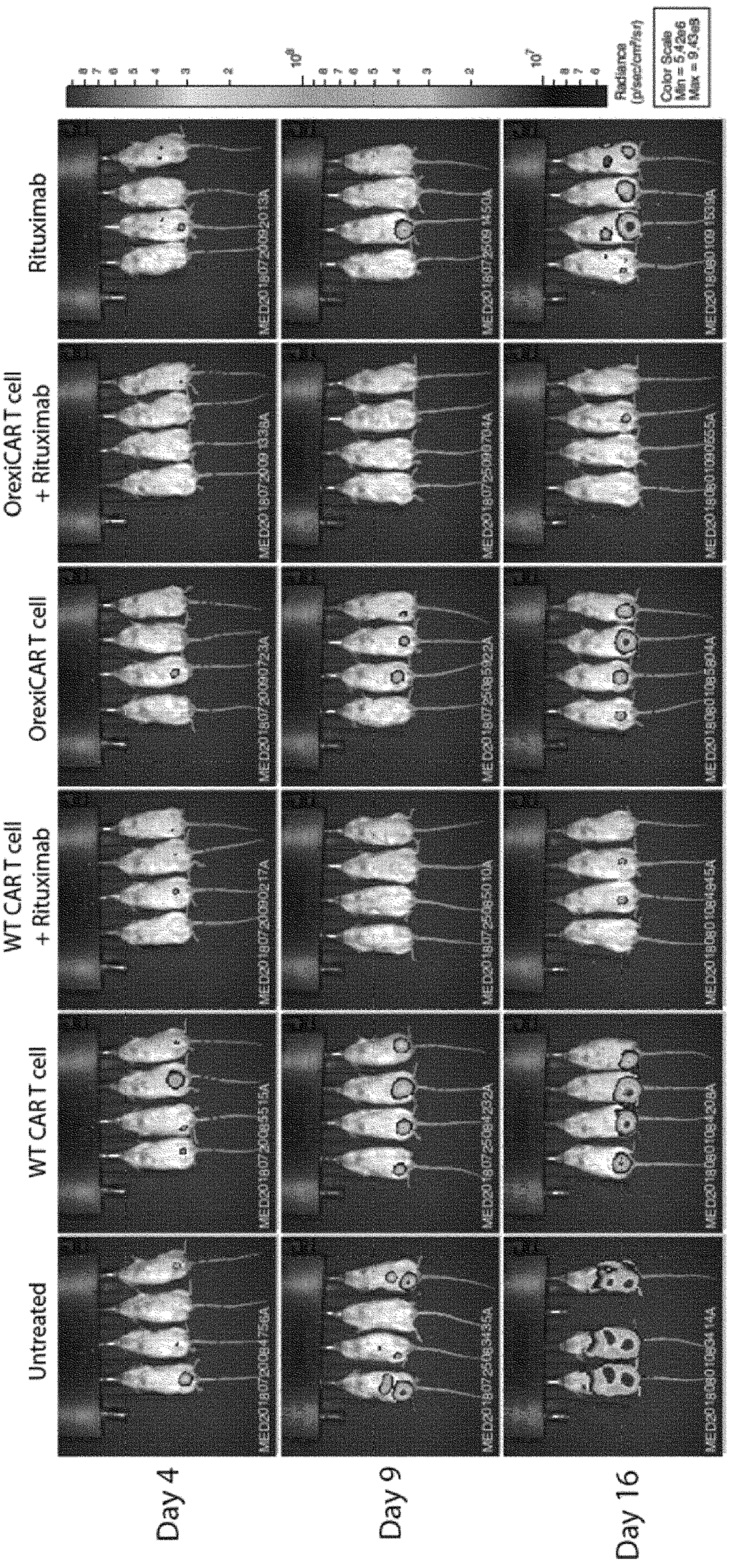
FIG. 8 shows raw bioluminescent images on a standardized scale taken on Days 4, 9, and 16 post tumor engraftment. The 6 treatment groups, with 4 mice in each treatment group, were: 1) tumor only, 2) single dose IP of CD19 CAR T cells (WT CAR T cells), 3) single dose IP of CD19 CAR T cells+100 μg TIW rituximab for 5 doses, 4) single dose IP of CD19 OrexiCAR T cells, 5) single dose IP of CD19 CAR T cells+100 μg TIW rituximab for 5 doses, and 6) 100 μg TIW rituximab for 5 doses.
Figure 9:
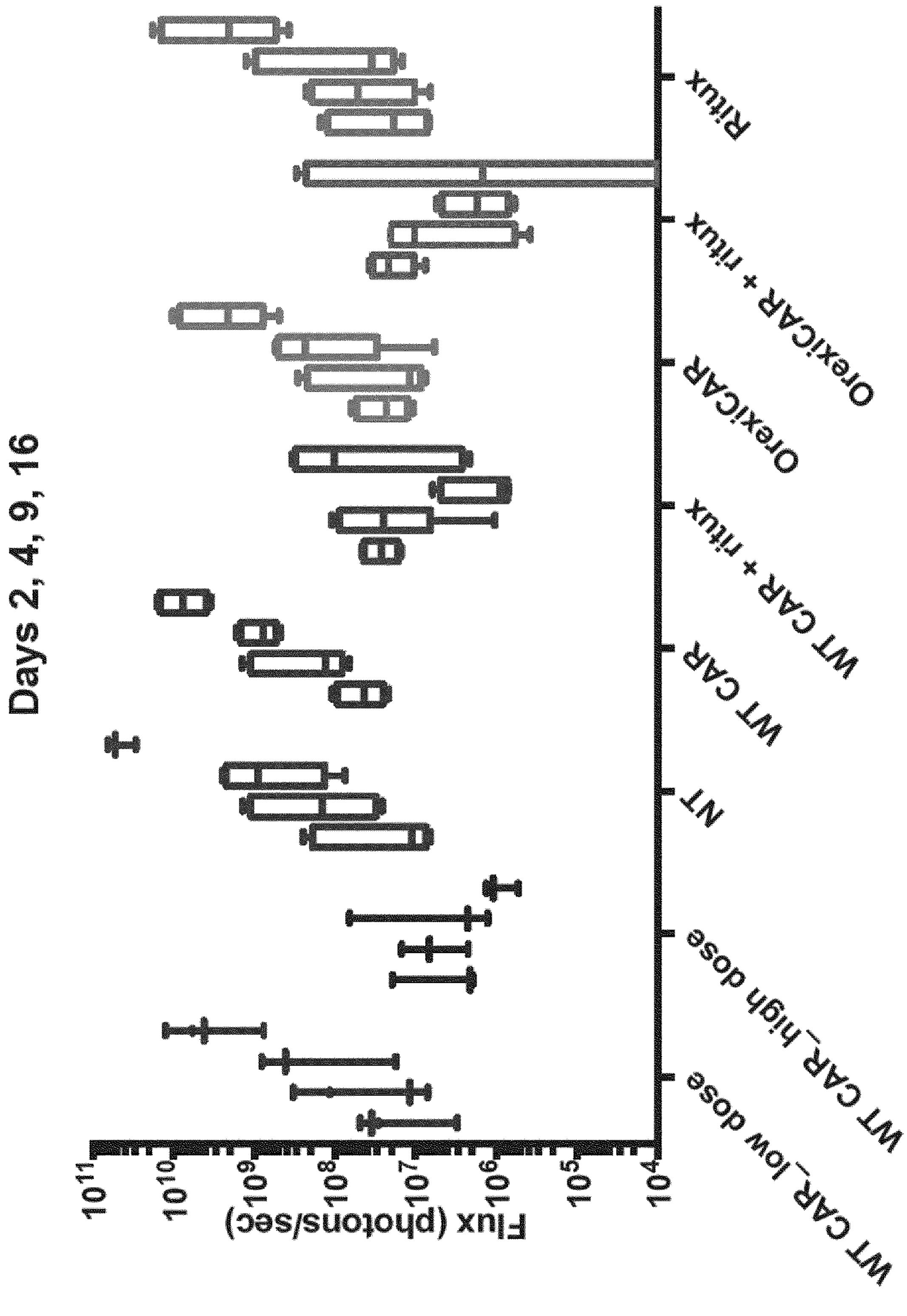
FIG. 9 shows the quantification of the photon flux from the luciferase tagged tumor cells in the 6 treatment groups from FIG. 8. The photon flux for high and low doses of CD19 CAR T cells are also shown.
Figure 10:
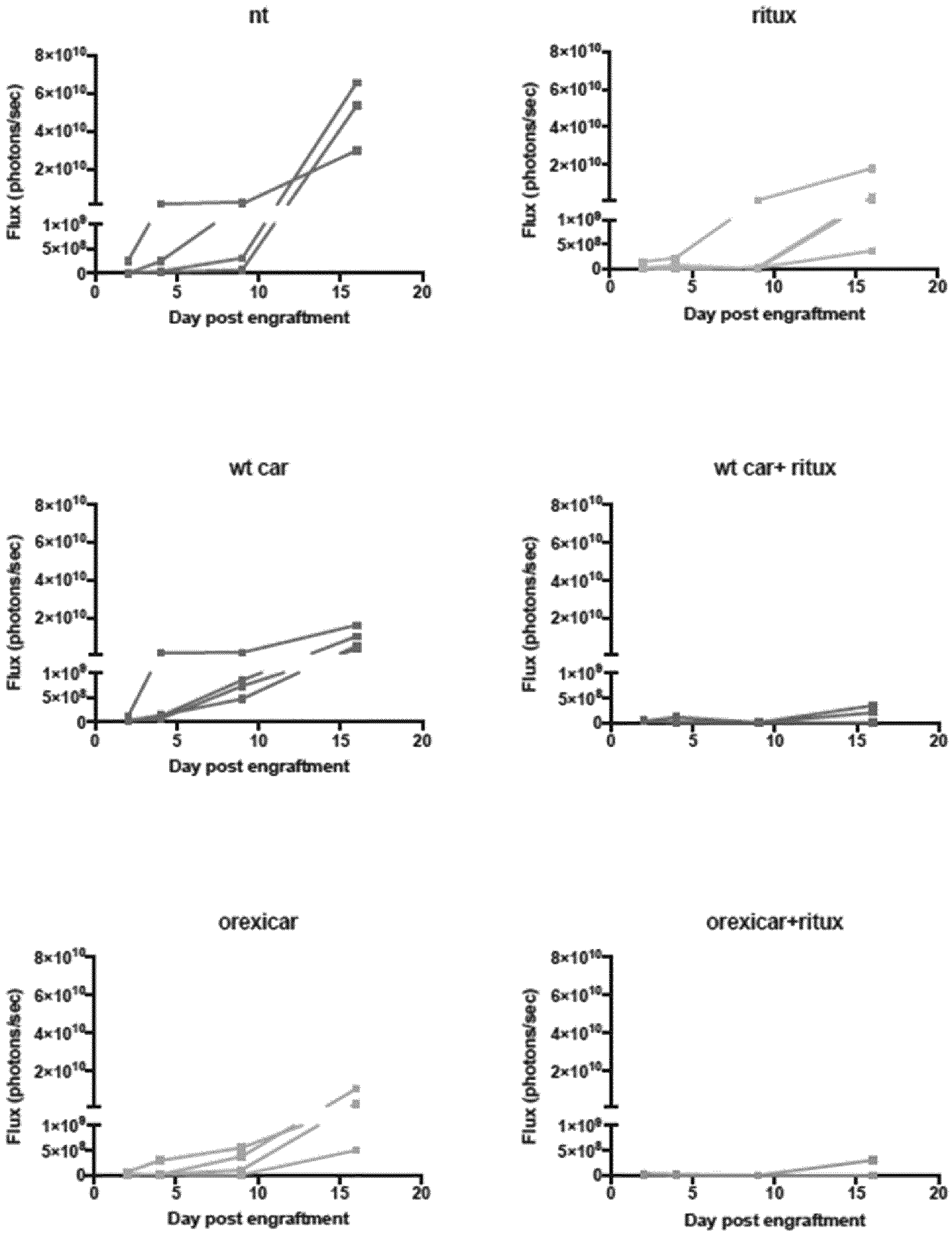
FIG. 10 shows the quantification of the photon flux from the luciferase tagged tumor cells on Days 2, 4, 9, and 16 post tumor engraftment for each of the individual mice in the 6 treatment groups from FIG. 8.
Figure 11A:
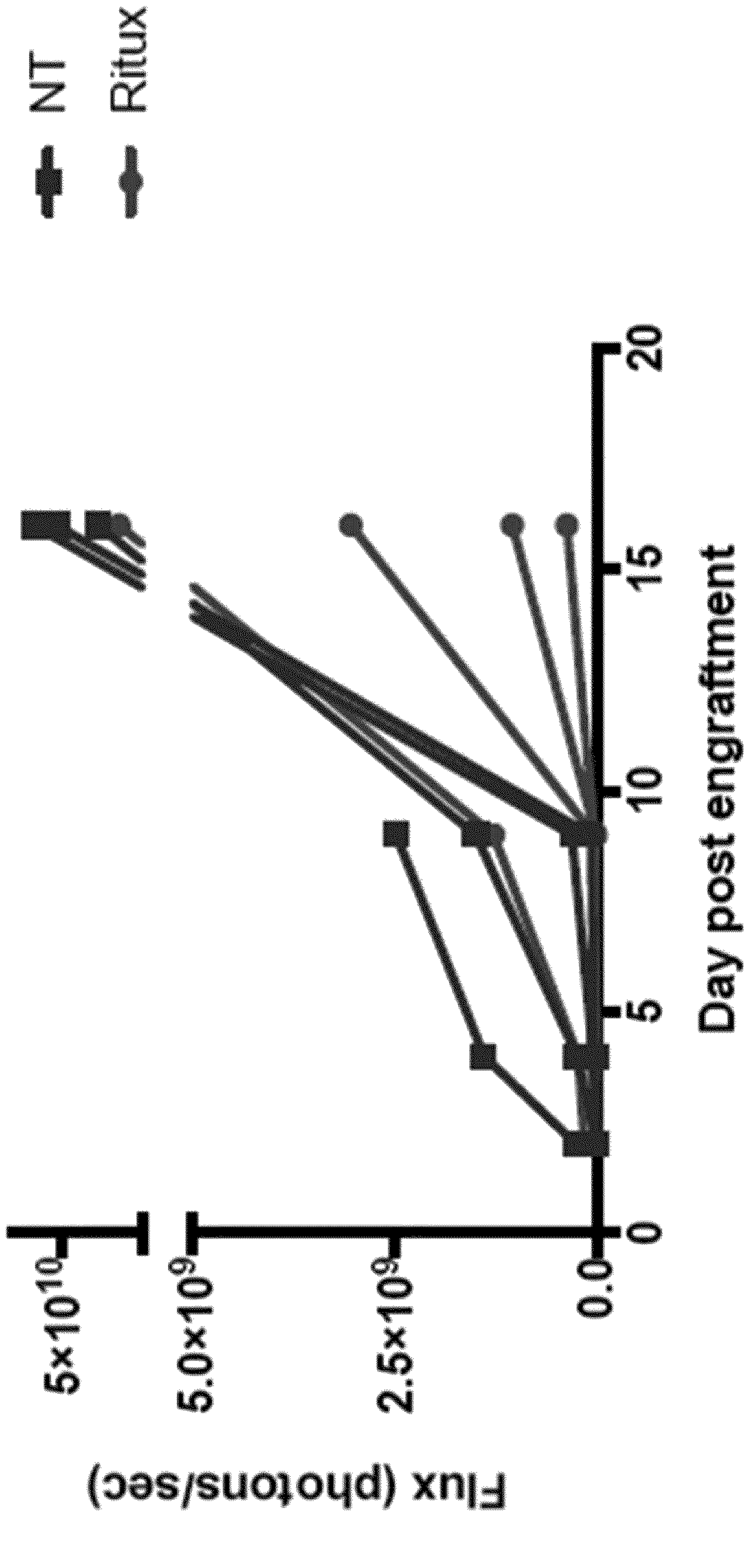
FIGS. 11A-11C show a comparison of the photon flux from the luciferase tagged tumor cells between selected treatment groups from FIG. 8.
Figure 11B:
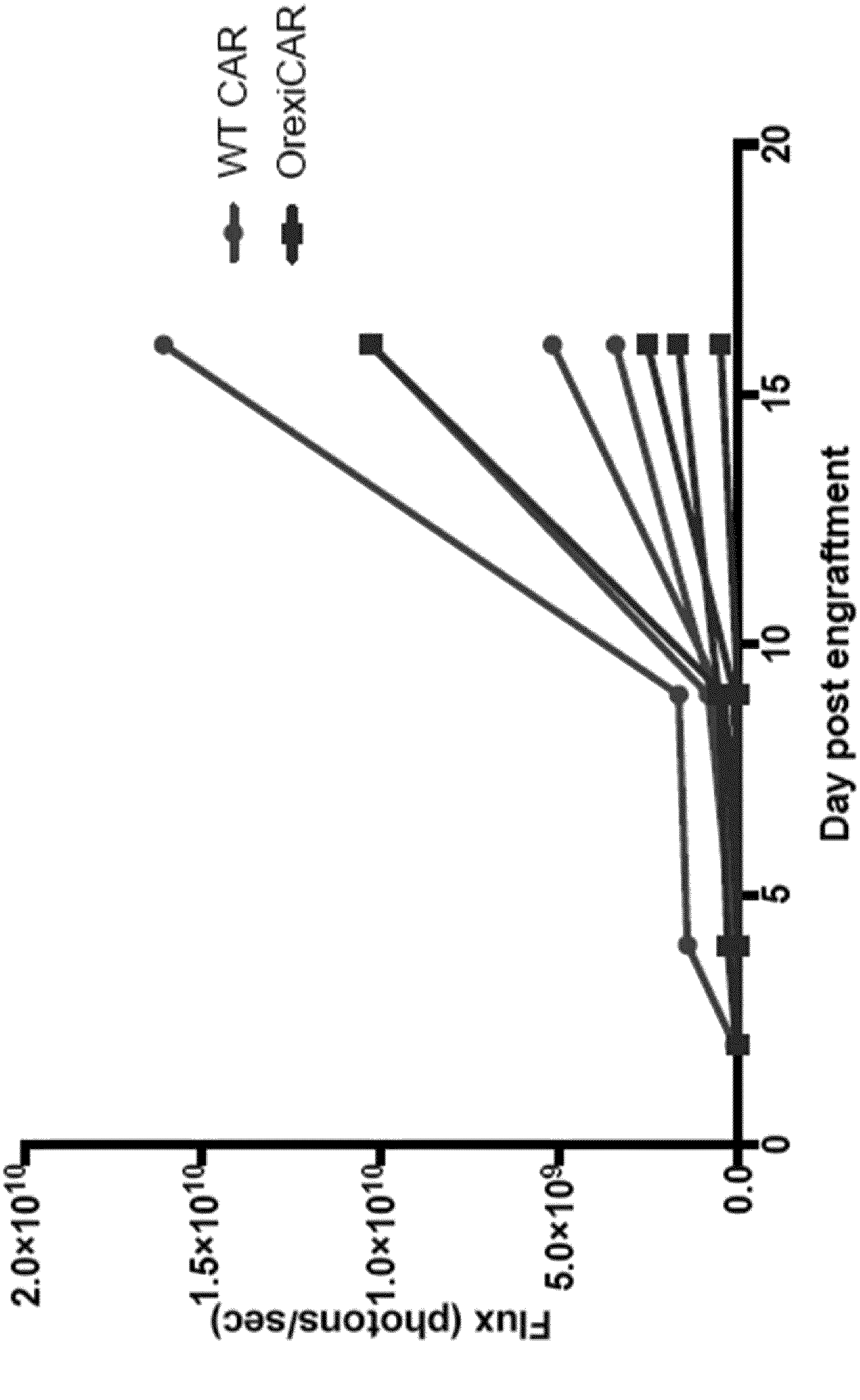
Figure 11C:
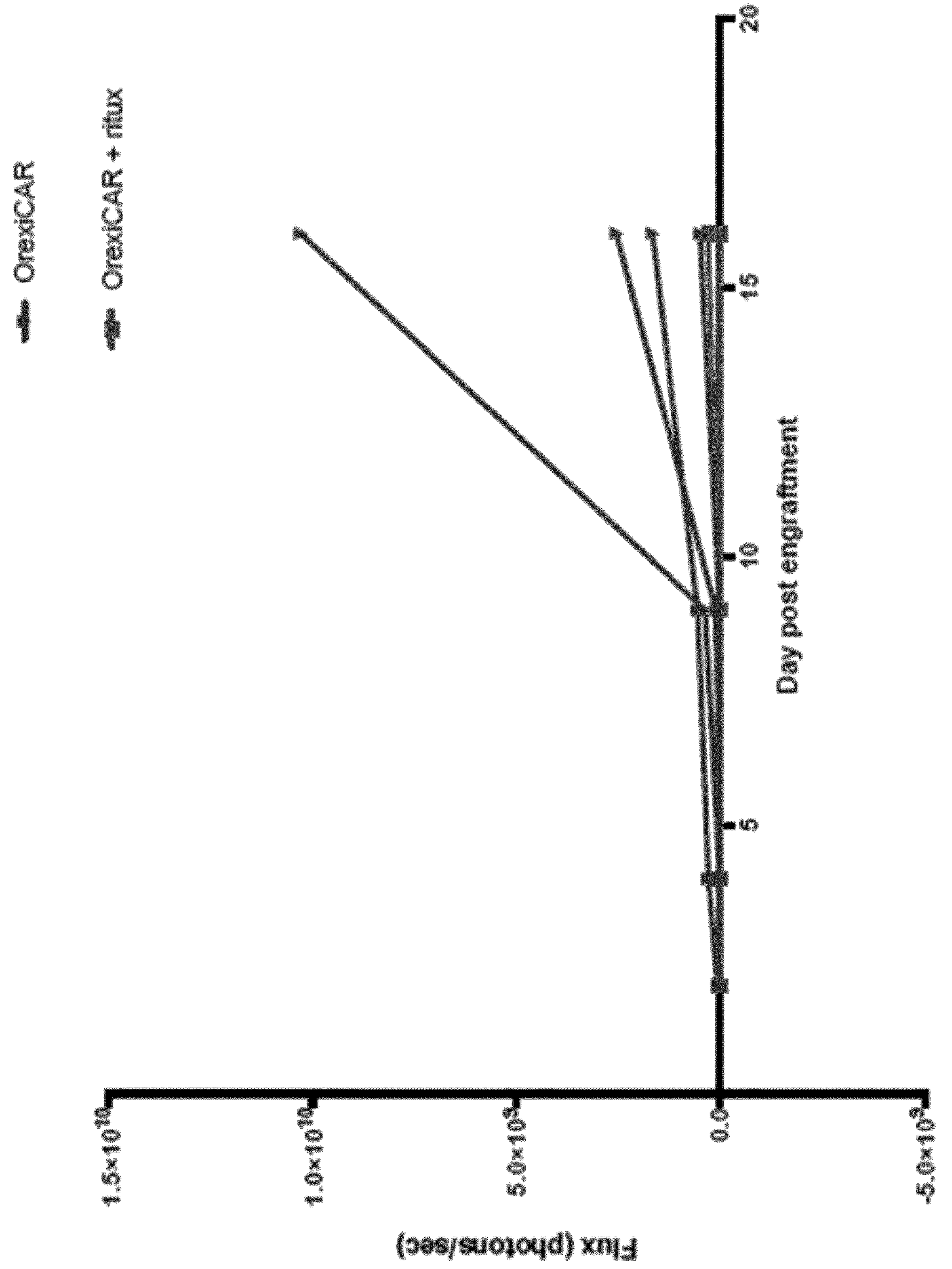
Figure 12:
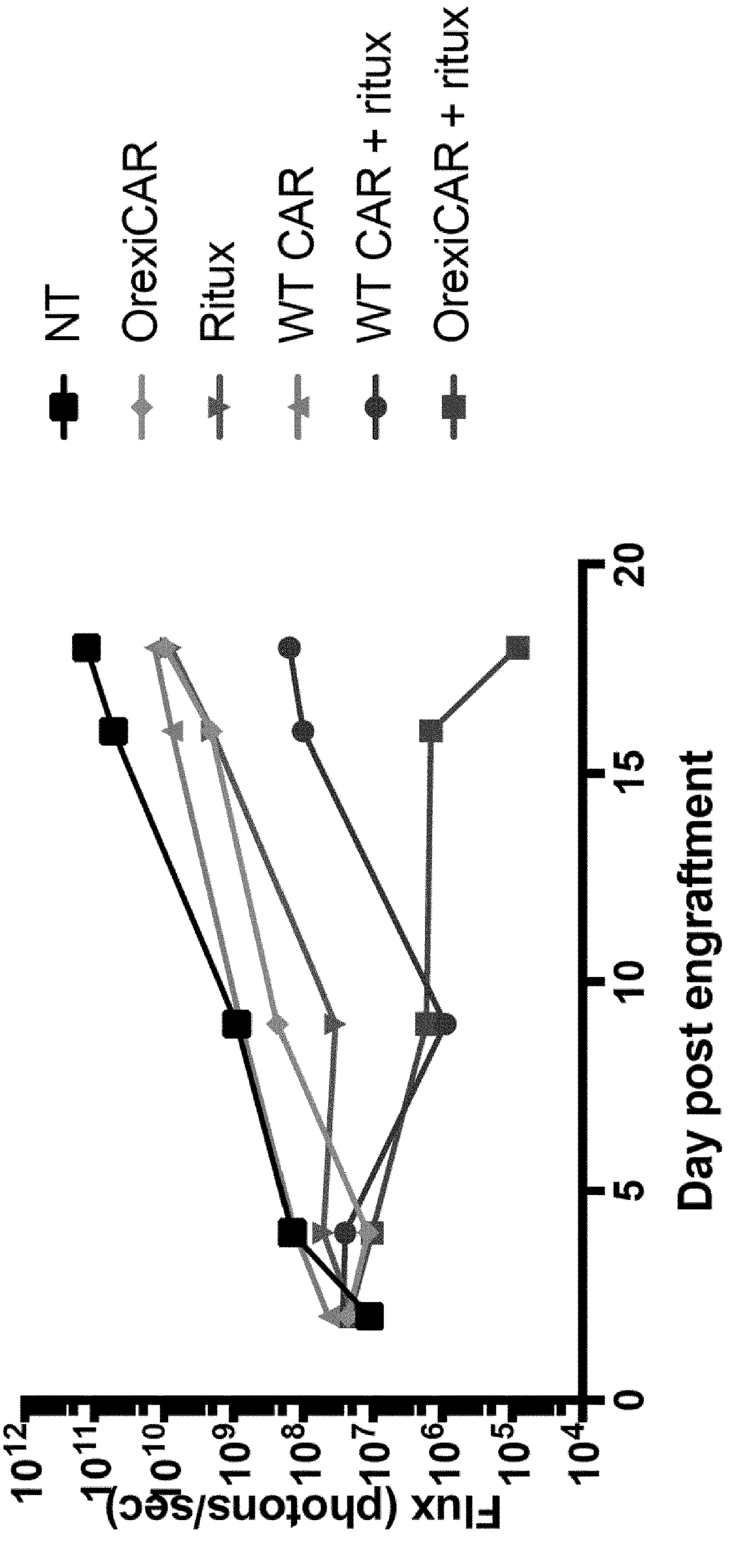
FIG. 12 shows the photon flux over time in mice with luciferase tagged lymphoma treated with CD19 OrexiCAR T cells alone or in combination with thrice weekly injections of rituximab, CD19 CAR T cells (WT CAR) alone or in combination thrice weekly injections of rituximab, rituximab alone, or in control non-transduced mice. Data are median of 4 mice.

The 6 treatment groups, with 4 mice in each treatment group, were: 1) tumor only, 2) single dose IP of CD19 CAR T cells (WT CAR T cells), 3) single dose IP of CD19 CAR T cells+200 μg TIW rituximab for 5 doses, 4) single dose IP of CD19 OrexiCAR T cells, 5) single dose IP of CD19 CAR T cells+200 μg TIW rituximab for 5 doses, and 6) 200 μg TIW rituximab for 5 doses. FIG. 8 shows raw bioluminescent images on a standardized scale taken on Days 4, 9, and 16. Tumor burden was quantified by measuring photon flux on Days 2, 4, 9, and 16 in each treatment group (FIGS. 9 and 10). A comparison between selected treatment groups is shown in FIG. 11. Rituximab had a benefit compared to untreated mice (FIG. 11A), CD19 OrexiCAR alone performed better than a standard CD19 CAR alone (FIG. 11B), and OrexiCAR plus rituximab worked better than a regular CAR plus rituximab (FIG. 11C). FIG. 12 shows the median data for the 4 mice in each treatment group. The data shows a marked benefit for CD19 OrexiCAR plus rituximab compared to standard wild type CD19 CAR plus rituximab. The combination also showed an improvement over either CAR alone or rituximab alone.

Figure 13:
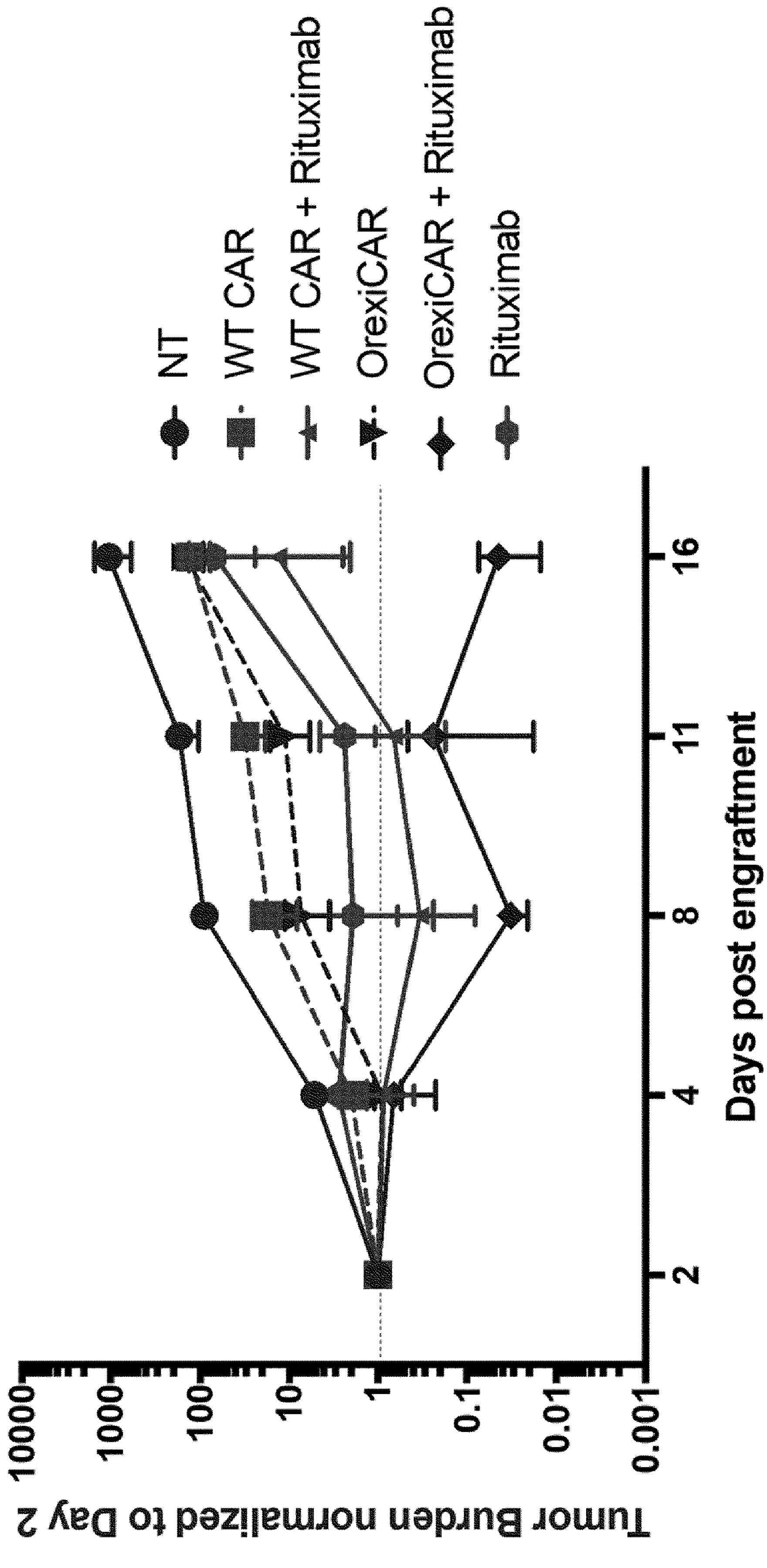
FIG. 13 shows the tumor burden over time in mice treated with CD19 OrexiCAR T cells alone or in combination with thrice weekly injections of rituximab, CD19 CAR T cells (WT CAR) alone or in combination thrice weekly injections of rituximab, rituximab alone, or in control non-transduced mice. The tumor burden was normalized to the burden on Day 2.

Another study was conducted with a reduced CAR T cell infusion number and rituximab dose. The 6 treatment groups were: 1) tumor only, 2) single dose IP of 500,000 CD19 CAR T cells (WT CAR T cells), 3) single dose IP of 500,000 CD19 CAR T cells+100 μg TIW rituximab for 5 doses, 4) single dose IP of 500,000 CD19 OrexiCAR T cells, 5) single dose IP of 500,000 CD19 CAR T cells+100 μg TIW rituximab for 5 doses, and 6) 100 μg TIW rituximab for 5 doses. Tumor burden was measured and FIG. 13 shows the tumor burden normalized to the tumor burden on Day 2. The data shows that CD19 OrexiCAR plus rituximab shows a 100-fold improvement over standard wild type CD19 CAR plus rituximab (FIG. 13). The combination also showed 100-fold improvement over either CAR alone or rituximab alone. Additionally, the tumors continued to shrink once treatment was stopped around Day 10 in the CD19 OrexiCAR plus rituximab group while the tumor burden started increasing in the other treatment groups.

Treatment efficacy is further determined clinically and by tumor growth. CAR T cell persistence is monitored by flow cytometry and RT-PCR of collected blood samples and endpoint bone marrow. Cytokine secretion by CAR T cells is assessed by Luminex technology against a panel of human specific cytokines including IFNg and IL2. CV1 concentration is monitored and quantified by ELISA.

Example 8. Ability of OrexiCAR Therapy to Prevent Antigen-Negative Relapse

Figure 14:
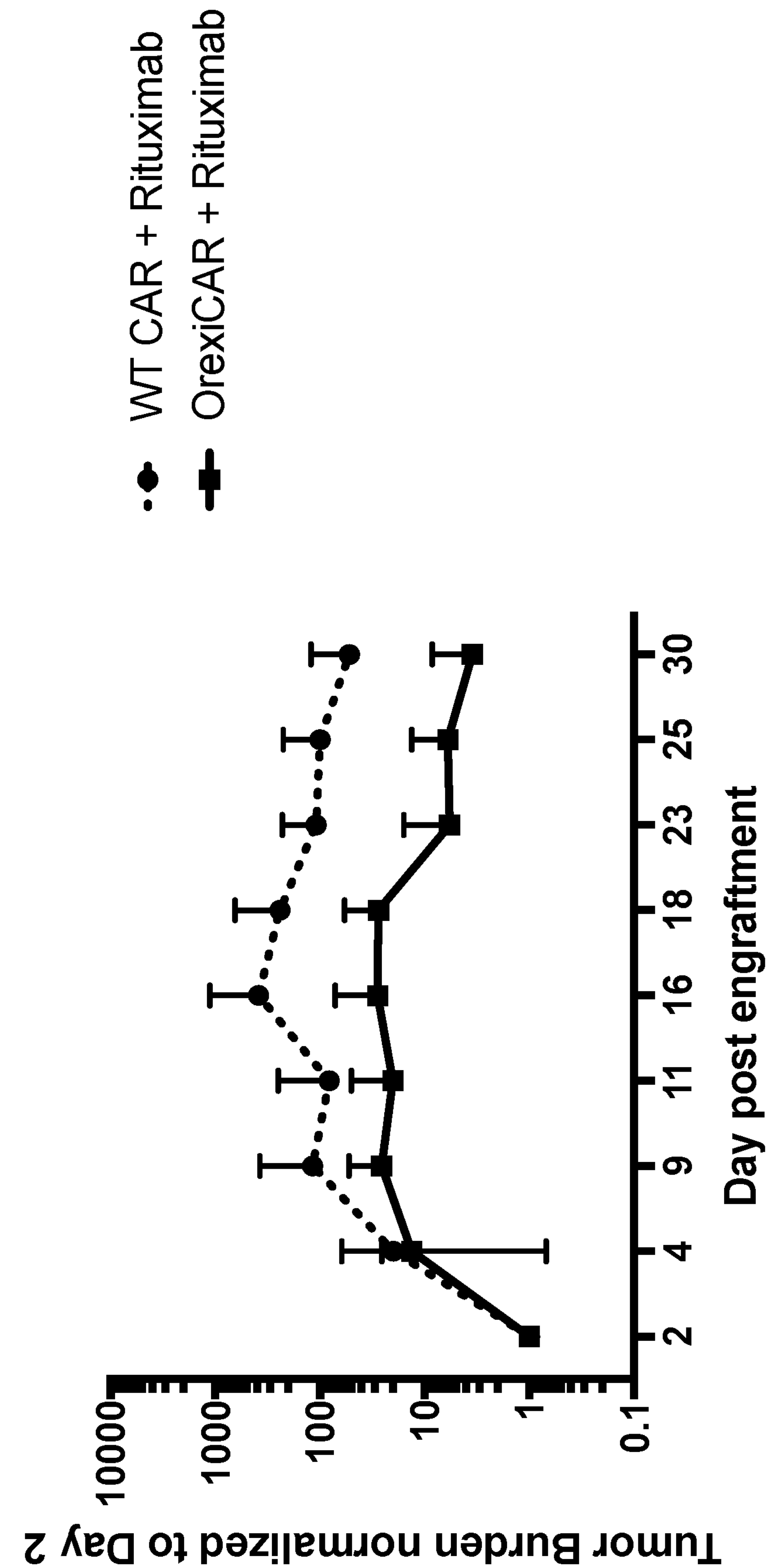
FIG. 14 shows the tumor burden over time in NSG mice engrafted with a mixed tumor model where 25% were wild type Raji lymphoma cells (CD20+/CD19+) and 75% were Raji-CD19 KO-Luciferase (CD20+/CD19−) and treated with CD19 OrexiCAR T cells or CD19 CAR T cells (WT CAR) in combination with thrice weekly injections of rituximab. Mean tumor burden normalized to Day 2 with error bars indicating standard deviation is plotted (n=5 per group). The scale is a logarithmic scale.

To model antigen-negative relapse and to address whether OrexiCAR T cell therapy can kill a heterogeneous tumor in which some cells do not have the CAR target on them, NSG mice were engrafted with a mixed tumor model where 25% were wild type Raji lymphoma cells (CD20+/CD19+) and 75% were Raji-CD19 KO-Luciferase (CD20+/CD19−). This allows monitoring tumor growth of only the CD19-negative tumor cells, which are not targets of the CAR. $5\times10^5$ total cells were engrafted in the IP cavity on Day 0. Mice were imaged and randomized on Day 2 and subsequently given $1\times10^6$ CAR T cells (either WT CAR or OrexiCAR, both to CD19). Beginning on Day 4, mice were treated TIW with 100 μg of Rituximab to CD20). Mean tumor burden was normalized to Day 2 with error bars indicating standard deviation is plotted (n=5 per group) (FIG. 14). OrexiCAR T cell combination therapy more effectively treats an antigen negative tumor than wild type (WT) CAR T cell with combination therapy. The OrexiCAR reduced the tumor by about 20-fold vs the wild type CAR T cell.

In another study, CD19 is genetically knocked out of Raji cells (Raji-CD19−/−) using the CRISPR-Cas9 system and engrafted into NSG mice at a ratio of 3:1 (Raji: Raji-CD19−/−) (Zah et al., *Cancer Immunol Res.* 4:498-508 (2016)). Tumor growth is quantified by BLI as both CD19+ and CD19-Raji cell types will be positive for luciferase and GFP. T cells are transduced with OrexiCAR and control vectors using methods described above. Control vectors include CAR alone, CV1 alone, and irrelevant CARs with and without BIW rituximab administration. After tumor engraftment, T cells are administered using previously described doses (Ruella et al., *J Clin Invest.* 126:3814-3826 (2016); Brentjens et al., *Nat Med.* 9:548-553 (2003)). Treatment efficacy is determined clinically and by tumor growth. CAR T cell persistence is monitored by flow cytometry and RT-PCR of collected blood samples and endpoint bone marrow. Cytokine secretion by CAR T cells is assessed by Luminex technology against a panel of human specific cytokines including IFNg and IL2. CV1 concentration is monitored and quantified by ELISA. To test if OrexiCAR T cells can prevent antigen-negative relapse, mice are sacrificed at various time points to collect tumors from bone marrow. The tumors are strained into a single cell suspension, sorted for GFP expression and then labeled with an anti-CD19 antibody, which are detected by flow cytometry. CD19-negative tumor cells are quantified and compared between OrexiCAR and WT CAR treated groups.

WT CAR treated tumors show increasing percentage of CD19-tumor cells, whereas OrexiCAR+rituximab treated groups do not. OrexiCAR treated tumors deplete tumors equally of CD19+ and CD19− cells, thereby preventing relapse of antigen-negative cells.

Example 9. Anti-Tumor Effect of OrexiCAR Therapy in an Immunosuppressive Tumor Model C57BL6 mice are injected IP with tumor cells engineered to express firefly luciferase. ID8 murine ovarian cancer cells engineered to express the MUC16 ectodomain and mouse Erbb2 (ID8-MUC16ecto-mErbb2) serve as an immunosuppressive solid tumor model. ID8-muc16ecto forms a highly immunosuppressive tumor microenvironment in C57BL6 mice and this tumor is not well controlled by WT 4H11 CAR T cells.51 Importantly, CV1 can bind to mouse CD47, allowing for the use of a syngeneic system (Weiskopf et al., *Science* 341:1-13 (2014)). Tumor growth is quantified by BLI. Mouse T cells are harvested from the spleens of healthy C57BL6 mice and transduced with OrexiCAR and control vectors (described in Example 7) using previously described protocols (Lee et al., *Methods Mol Biol.* 506:83-96 (2009)). T cells and mAbs (anti-mErbb2) are administered IV using doses and schedules described in Example 8. Treatment efficacy is determined clinically and by tumor growth. CAR T cell persistence is monitored by flow cytometry and RT-PCR of collected blood samples and endpoint bone marrow. Luminex technology is used to assess secretion of mouse specific cytokines mIFNg and mIL2. CV1 concentration is monitored and quantified by ELISA.

OrexiCAR+mAb therapy better eradicates an immunosuppressive solid tumor compared to WT CARs as measured by increased overall survival and reduction in tumor size via BLI.

Example 10. Pharmacokinetics of OrexiCAR T Cells and Secreted CV1

Pharmacokinetics of OrexiCAR T cells and CV1 are assessed in the models described in Example 7. Transduced OrexiCAR and control T cells are injected into mice via tail vein at varying doses. Blood is drawn weekly from mice to assess T cell proliferation and persistence and CV1 concentration. T cell expansion is analyzed by flow cytometry and RT-PCR in antigen-positive and -negative tumor models. CV1 concentration is quantified by ELISA in the same models.

CV1 concentration, by ELISA, is proportional to OrexiCAR expansion in the blood, quantified by flow cytometry and RT PCR.

Example 11. Cellular Mechanism of OrexiCAR Therapy

To understand the role of dendritic cells and macrophages in CV1 therapy, Eμ-ALL01 B cell leukemia cell line engineered to express luciferase is injected via tail vein into immunocompetent mice. This cell line is responsive to treatment by mCD19 CAR T cells (Paszkiewicz et al., *J Clin Invest.* 126:1-11 (2016); Davila et al., *PLoS One* 8:1-14 (2013)). WT CAR T cells targeted to mCD19 are titrated to a suboptimal dose in order to observe any additional anti-tumor effect from the CV1/mAb arm of this therapy. Treatment groups include WT mCD19-CARs+/−anti-mCD20, OrexiCARs+/−anti-mCD20, OrexiCARACD3zeta+/−anti-mCD20, daily IP injection of CV1+/−anti-mCD20, and anti-mCD20 alone. OrexiCARΔCD3zeta removes the CD3zeta chain from the CAR and allows for tumor targeting without killing mediated by the CAR T cell. This is used to assess T cell secreted CV1. Syngeneic CAR T cells are transduced using protocols described in Example 9. T cells and mAbs (anti-mCD20) are administered IV using doses and schedules optimized in Examples 7-10. Treatment efficacy is assessed as described in Examples 7-10. To understand the cellular mechanism of OrexiCAR therapy mice are depleted of dendritic cells and the effect on treatment efficacy is studied.

To deplete DCs, CD11c-DTR mice are engrafted and treated. CD11c-DTR mice are treated with diphtheria toxin (DT) to deplete dendritic cells. Depletion of CD11C+ dendritic cells abrogates priming of CD8+ T cells, the proposed mechanism of anti-CD47 therapy (Jung et al., *Immunity* 17:211-220 (2002)). A group of untreated, tumor bearing mice is treated with DT to control for toxicities related to its administration. Efficacy is compared between DT treated and non-treated groups of CD11c-DTR mice, measured using BLI.

Depletion of DCs abrogates the anti-tumor effect of CV1 therapy and subsequently dampens the anti-tumor effect of OrexiCAR therapy as measured by increased tumor size and decrease in mouse survival.

Embodiment 1: An engineered immune cell comprising: (a) a SIRPα polypeptide that binds to human CD47 and/or a nucleic acid encoding the SIRPα polypeptide; and (b) a receptor that binds to a target antigen and/or nucleic acid encoding the receptor.

Embodiment 2: The engineered immune cell of embodiment 1, wherein the receptor is a T cell receptor.

Embodiment 3: The engineered immune cell of embodiment 1, wherein the receptor is a native cell receptor.

Embodiment 4: The engineered immune cell of embodiment 1, wherein the receptor is a non-native cell receptor.

Embodiment 5: The engineered immune cell of embodiment 4, wherein the non-native cell receptor is a truncated receptor, a genetically altered receptor, a TCR mimic receptor, or antibody, or a ligand capable of interacting with a target cell.

Embodiment 6: The engineered immune cell of embodiment 1, wherein the receptor is a chimeric antigen receptor.

Embodiment 7: The engineered immune cell of any of embodiments 1-6, wherein the SIRPα polypeptide has at least 80%, 85%, 90%, 95%, 96%, 97%, 98%, or 99% sequence identity to SEQ ID NO: 33, and optionally lacks the transmembrane domain.

Embodiment 8: The engineered immune cell of any of embodiments 1-6, wherein the SIRPα polypeptide has at least 80%, 85%, 90%, 95%, 96%, 97%, 98%, or 99% sequence identity to SEQ ID NO: 34.

Embodiment 9: The engineered immune cell of any of embodiments 1-8, wherein the SIRPα polypeptide is secreted.

Embodiment 10: The engineered immune cell of any of embodiments 1-8, wherein the SIRPα polypeptide is membrane-bound.

Embodiment 11: The engineered immune cell of any one of embodiments 1-10, wherein the nucleic acid encoding the SIRPα polypeptide comprises a leader sequence for secretion of the soluble SIRPα polypeptide.

Embodiment 12: The engineered immune cell of any of embodiments 1-11, wherein the nucleic acid encoding the SIRPα polypeptide is operably linked to a promoter.

Embodiment 13: The engineered immune cell of embodiment 12, wherein the promoter is a constitutive promoter.

Embodiment 14: The engineered immune cell of embodiment 12, wherein the promoter is a conditional promoter.

Embodiment 15: The engineered immune cell of embodiment 14, wherein the conditional promoter is inducible by binding of the receptor to the target antigen.

Embodiment 16: The engineered immune cell of any of embodiments 1-15, wherein the target antigen is a tumor antigen.

Embodiment 17: The engineered immune cell of any of embodiments 1-15, wherein the target antigen is an antigen expressed by a normal healthy cell.

Embodiment 18: The engineered immune cell of any of embodiments 1-15, wherein the target antigen is an extracellular antigen.

Embodiment 19: The engineered immune cell of embodiment 6, wherein the chimeric antigen receptor comprises (i) an extracellular antigen binding domain; (ii) a transmembrane domain; and (iii) an intracellular domain.

Embodiment 20: The engineered immune cell of embodiment 19, wherein the extracellular antigen binding domain binds to the target antigen.

Embodiment 21: The engineered immune cell of embodiment 19, wherein the extracellular antigen binding domain binds to a tumor antigen.

Embodiment 22: The engineered immune cell of embodiment 21, wherein the tumor antigen is selected from among MUC16, mesothelin, CD19, WT1, PSCA, and BCMA.

Embodiment 23: The engineered immune cell of any of embodiments 19-22, wherein the extracellular antigen binding domain comprises a single chain variable fragment (scFv).

Embodiment 24: The engineered immune cell of any of embodiments 19-23, wherein the extracellular antigen binding domain comprises a human scFv.

Embodiment 25: The engineered immune cell of any of embodiments 19-24, wherein the extracellular antigen binding domain comprises a CD19 scFv of SEQ ID NO: 3 or SEQ ID NO: 4.

Embodiment 26: The engineered immune cell of any of embodiments 19-24, wherein the extracellular antigen binding domain comprises a CD19 scFv having at least 80%, 85%, 90%, 95%, 96%, 97%, 98%, or 99% sequence identity to SEQ ID NO: 3 or SEQ ID NO: 4.

Embodiment 27: The engineered immune cell of any of embodiments 19-24, wherein the extracellular antigen binding domain comprises a MUC16 scFv of SEQ ID NO: 41 or SEQ ID NO: 44.

Embodiment 28: The engineered immune cell of any of embodiments 19-24, wherein the extracellular antigen binding domain comprises a MUC16 scFv having at least 80%, 85%, 90%, 95%, 96%, 97%, 98%, or 99% sequence identity to SEQ ID NO: 41 or SEQ ID NO: 44.

Embodiment 29: The engineered immune cell of any of embodiments 19-28, wherein the extracellular antigen binding domain comprises a signal peptide that is covalently joined to the N-terminus of the extracellular antigen binding domain.

Embodiment 30: The engineered immune cell of any of embodiments 19-29, wherein the transmembrane domain comprises a CD8 transmembrane domain.

Embodiment 31: The engineered immune cell of any of embodiments 19-30, wherein the intracellular domain comprises one or more costimulatory domains.

Embodiment 32: The engineered immune cell of embodiment 31, wherein the one or more costimulatory domains are selected from a CD28 costimulatory domain, a CD3ζ-chain, a 4-1BBL costimulatory domain, or any combination thereof.

Embodiment 33: The engineered immune cell of any of embodiments 1-32, wherein the engineered immune cell is a white blood cell.

Embodiment 34: The engineered immune cell of embodiment 33, wherein the white blood cell is a T cell, a B cell, neutrophil, or a natural killer (NK) cell.

Embodiment 35: The engineered immune cell of embodiment 34, wherein the T cell is a CD4+ T cell or a CD8+ T cell.

Embodiment 36: The engineered immune cell of any of embodiments 1-35, wherein the engineered immune cell is a tumor infiltrating lymphocyte.

Embodiment 37: The engineered immune cell of any of embodiments 1-36, wherein the engineered immune cell is derived from an autologous donor or an allogenic donor.

Embodiment 38: A polypeptide comprising a SIRPα polypeptide and a chimeric antigen receptor.

Embodiment 39: The polypeptide of embodiment 38, further comprising a self-cleaving peptide located between the SIRPα polypeptide and the chimeric antigen receptor.

Embodiment 40: The polypeptide of embodiment 39, wherein the self-cleaving peptide is a P2A self-cleaving peptide.

Embodiment 41: The polypeptide of any of embodiments 38-40, wherein the SIRPα polypeptide comprises a leader sequence for secretion of the soluble SIRPα polypeptide.

Embodiment 42: The polypeptide of any of embodiments 38-41, wherein the chimeric antigen receptor comprises (i) an extracellular antigen binding domain; (ii) a transmembrane domain; and (iii) an intracellular domain.

Embodiment 43: The polypeptide of embodiment 42, wherein the antigen binding domain binds to a tumor antigen.

Embodiment 44: The polypeptide of embodiment 43, wherein the tumor antigen is selected from among from among MUC16, mesothelin, CD19, WT1, PSCA, and BCMA.

Embodiment 45: The polypeptide of any of embodiments 42-44, wherein the antigen binding domain comprises a single chain variable fragment (scFv).

Embodiment 46: The polypeptide of any of embodiments 42-45, wherein the extracellular antigen binding domain comprises a CD19 scFv of SEQ ID NO: 3 or SEQ ID NO: 4.

Embodiment 47: The polypeptide of any of embodiments 42-45, wherein the extracellular antigen binding domain comprises a CD19 scFv having at least 80%, 85%, 90%, 95%, 96%, 97%, 98%, or 99% sequence identity to SEQ ID NO: 3 or SEQ ID NO: 4.

Embodiment 48: The polypeptide of any of embodiments 42-45, wherein the extracellular antigen binding domain comprises a MUC16 scFv of SEQ ID NO: 41 or SEQ ID NO: 44.

Embodiment 49: The polypeptide of any of embodiments 42-45, wherein the extracellular antigen binding domain comprises a MUC16 scFv having at least 80%, 85%, 90%, 95%, 96%, 97%, 98%, or 99% sequence identity to SEQ ID NO: 41 or SEQ ID NO: 44.

Embodiment 50: The polypeptide of any of embodiments 42-49, wherein the transmembrane domain comprises a CD8 transmembrane domain.

Embodiment 51: The polypeptide of any of embodiments 42-50, wherein the intracellular domain comprises one or more costimulatory domains.

Embodiment 52: The polypeptide of embodiment 51, wherein the one or more costimulatory domains are selected from a CD28 costimulatory domain, a CD3ζ-chain, a 4-1BBL costimulatory domain, or any combination thereof.

Embodiment 53: A nucleic acid encoding the polypeptide of any of embodiments 38-52.

Embodiment 54: A nucleic acid encoding a SIRPα polypeptide and a chimeric antigen receptor, wherein the chimeric antigen receptor comprises (i) an extracellular antigen binding domain; (ii) a transmembrane domain; and (iii) an intracellular domain.

Embodiment 55: The nucleic acid of embodiment 54, wherein the nucleic acid further comprises a polynucleotide region encoding a self-cleaving peptide.

Embodiment 56: The nucleic acid of embodiment 55, wherein the self-cleaving peptide is a P2A self-cleaving peptide.

Embodiment 57: The nucleic acid of any one of embodiments 54-56, wherein the self-cleaving peptide is located between the SIRPα polypeptide and the chimeric antigen receptor.

Embodiment 58: The nucleic acid of any one of embodiments 53-57, wherein the nucleic acid is operably linked to a promoter.

Embodiment 59: The nucleic acid of embodiment 58, wherein the promoter is a constitutive promoter.

Embodiment 60: The nucleic acid of embodiment 58, wherein the promoter is a conditional promoter.

Embodiment 61: The nucleic acid of embodiment 60, wherein the conditional promoter is inducible by the CAR binding to an antigen.

Embodiment 62: A vector comprising the nucleic acid of any of embodiments 53-61.

Embodiment 63: The vector of embodiment 62, wherein the vector is a viral vector or a plasmid.

Embodiment 64: The vector of embodiment 62, wherein the vector is a retroviral vector.

Embodiment 65: A host cell comprising the nucleic acid of any of embodiments 53-61 or the vector of any of embodiments 62-64.

Embodiment 66: A method for treating cancer in a subject in need thereof comprising administering an effective amount of the engineered immune cells of any of embodiments 1-37.

Embodiment 67: The method of embodiment 66, further comprising administering to the subject a monoclonal antibody.

Embodiment 68: A method for treating of inhibiting tumor growth or metastasis in a subject comprising contacting a tumor cell with an effective amount of the engineered immune cells of any of embodiments 1-37.

Embodiment 69: The method of embodiment 68, further comprising administering to the subject a monoclonal antibody.

Embodiment 70: The method of embodiment 67 or 69, wherein the monoclonal antibody is rituximab.

Embodiment 71: The method of any of embodiments 67, 69, or 70, wherein the monoclonal antibody is administered prior to, simultaneously with, or subsequent to administration of the engineered immune cells.

Embodiment 72: The method of any of embodiments 67, 69, or 70-71, wherein the monoclonal antibody is administered 3 months or more after the administration of the engineered immune cells.

Embodiment 73: The method of any of embodiments 67, 69, or 70-71, wherein the monoclonal antibody is administered up to 10 days before the administration of the engineered immune cells.

Embodiment 74: The method of any of embodiments 66-73, wherein: (i) the target antigen bound by the receptor is MUC16 and the monoclonal antibody specifically binds to EGFR or Her2; (ii) the target antigen bound by the receptor is mesothelin and the monoclonal antibody specifically binds to EGFR; (iii) the target antigen bound by the receptor is WT1 and the monoclonal antibody specifically binds to CD33; (iv) the target antigen bound by the receptor is PSCA and the monoclonal antibody specifically binds to PSMA; or (v) the target antigen bound by the receptor is BCMA and the monoclonal antibody specifically binds to CD38.

Embodiment 75: The method of any of embodiments 66-74, wherein the engineered immune cells are administered intravenously, intraperitoneally, subcutaneously, intramuscularly, or intratumorally.

Embodiment 76: The method of any of embodiments 66-75, wherein the cancer or tumor is a carcinoma, sarcoma, a melanoma, or a hematopoietic cancer.

Embodiment 77: The method of any of embodiments 66-76, wherein the cancer or tumor is selected from among adrenal cancers, bladder cancers, blood cancers, bone cancers, brain cancers, breast cancers, carcinoma, cervical cancers, colon cancers, colorectal cancers, corpus uterine cancers, ear, nose and throat (ENT) cancers, endometrial cancers, esophageal cancers, gastrointestinal cancers, head and neck cancers, Hodgkin's disease, intestinal cancers, kidney cancers, larynx cancers, leukemias, liver cancers, lymph node cancers, lymphomas, lung cancers, melanomas, mesothelioma, myelomas, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof.

Embodiment 78: The method of any of embodiments 66-77, further comprising administering an additional cancer therapy.

Embodiment 79: The method of embodiment 78, wherein the additional cancer therapy is selected from among chemotherapy, radiation therapy, immunotherapy, monoclonal antibodies, anti-cancer nucleic acids or proteins, anti-cancer viruses or microorganisms, and any combinations thereof.

Embodiment 80: The method of any one of embodiments 66-79, further comprising administering a cytokine to the subject.

Embodiment 81: The method of embodiment 80, wherein the cytokine is administered prior to, during, or subsequent to administration of the one or more engineered immune cells.

Embodiment 82: The method of embodiment 80 or 81, wherein the cytokine is selected from a group consisting of interferon α, interferon 3, interferon 7, complement C5a, IL-2, TNFalpha, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2.

Embodiment 83: A method for preparing immune cells for cancer therapy, comprising isolating immune cells from a donor subject, transducing the immune cells with (a) the nucleic acid of any of embodiments 53-61 or (b) the vector of any of embodiments 62-64.

Embodiment 84: A method of treatment comprising isolating immune cells from a donor subject, transducing the immune cells with (a) the nucleic acid of any of embodiments 53-61 or (b) the vector of any of embodiments 62-64, and administering the transduced immune cells to a recipient subject.

Embodiment 85: The method of embodiment 83 or 84, wherein the donor subject and the recipient subject are the same.

Embodiment 86: The method of embodiment 83 or 84, wherein the donor subject and the recipient subject are different.

Embodiment 87: The method of any of embodiments 83-86, wherein the immune cells isolated from the donor subject comprise one or more white blood cells.

Embodiment 88: The method of embodiment 87, wherein the one or more white blood cells is a T cell, a B cell, or a natural killer (NK) cell.

Embodiment 89: The method of embodiment 88, wherein the T cell is a CD4+ T cell or a CD8+ T cell.

Embodiment 90: The method of any of embodiments 83-89, wherein the immune cells isolated from the donor subject comprise tumor infiltrating lymphocytes.

Embodiment 91: Use of the engineered immune cells of any of embodiments 1-37 for treating a cancer.

Embodiment 92: Use of the engineered immune cells of any of embodiments 1-37 in the preparation of a medicament for the treatment of a cancer.

Embodiment 93: A method for treating of inhibiting tumor growth or metastasis in a subject comprising contacting a tumor cell with an effective amount of the engineered immune cells of any of embodiments 1-37, wherein the engineered immune cells target a first antigen, in combination with an antibody directed to a second antigen, whereby the combination prevents escape of the CAR target antigen-negative cells.

What is claimed is:

1. An engineered immune cell comprising:

(a) a truncated Signal Regulatory Protein Alpha (SIRPα) polypeptide having the amino acid sequence of SEQ ID NO: 34 or SEQ ID NO: 35, wherein the truncated SIRPα polypeptide binds to human CD47, lacks a transmembrane domain, is not fused to an immunoglobulin Fc domain, and is secreted, and/or a nucleic acid encoding the truncated SIRPα polypeptide; and (b) a receptor polypeptide that binds to a target antigen and/or nucleic acid encoding the receptor polypeptide, wherein the receptor polypeptide is expressed at the cell surface of the T cell, and wherein the engineered immune cell is an engineered T cell.

2. The engineered immune cell of claim 1, wherein the receptor polypeptide is a T cell receptor polypeptide, or a chimeric antigen receptor polypeptide.

3. The engineered immune cell of claim 2, wherein the chimeric antigen receptor polypeptide comprises (i) an extracellular antigen binding domain, optionally wherein the extracellular antigen binding domain binds to the target antigen, or comprises a single chain variable fragment (scFv) or a human scFv;

(ii) a transmembrane domain, optionally comprising a CD8 transmembrane domain; and (iii) an intracellular domain, optionally comprising one or more costimulatory domains, selected from the group consisting of a CD28 costimulatory domain, a CD32-chain, a 4-1BBL costimulatory domain, and any combination thereof.

4. The engineered immune cell of claim 3, wherein the extracellular antigen binding domain comprises:

a CD19 scFv having at least 80%, 85%, 90%, 95%, 96%, 97%, 98%, or 99% sequence identity to SEQ ID NO: 3 or SEQ ID NO: 4 or a CD19 scFv of SEQ ID NO: 3 or SEQ ID NO: 4;

a MUC16 scFv having at least 80%, 85%, 90%, 95%, 96%, 97%, 98%, or 99% sequence identity to SEQ ID NO: 41 or SEQ ID NO: 44 or a MUC16 scFv of SEQ ID NO: 41 or SEQ ID NO: 44.

5. The engineered immune cell of claim 1, wherein the engineered T cell is a CD4+ T cell or a CD8+ T cell.

6. A method for treating of inhibiting tumor growth or metastasis in a subject comprising contacting a tumor cell with an effective amount of the engineered immune cell of claim 1, wherein the engineered immune cells target a first antigen, in combination with an antibody directed to a second antigen, whereby the combination prevents escape of the CAR target antigen-negative cells.

* * * * *